United States Patent
Kasdan

(10) Patent No.: US 10,527,538 B2
(45) Date of Patent: Jan. 7, 2020

(54) SYSTEM AND APPARATUS FOR BLIND DECONVOLUTION OF FLOW CYTOMETER PARTICLE EMISSION

(71) Applicant: ACCELLIX LTD., Jerusalem (IL)

(72) Inventor: Harvey Lee Kasdan, Jerusalem (IL)

(73) Assignee: ACCELLIX LTD., Jerusalem (IL)

( * ) Notice: Subject to any disclaimer, the term of this patent is extended or adjusted under 35 U.S.C. 154(b) by 0 days.

(21) Appl. No.: 15/576,826

(22) PCT Filed: May 23, 2016

(86) PCT No.: PCT/IL2016/000010
§ 371 (c)(1),
(2) Date: Nov. 26, 2017

(87) PCT Pub. No.: WO2016/189522
PCT Pub. Date: Dec. 1, 2016

(65) Prior Publication Data
US 2018/0306698 A1    Oct. 25, 2018

Related U.S. Application Data

(60) Provisional application No. 62/167,524, filed on May 28, 2015.

(51) Int. Cl.
*G01N 15/14* (2006.01)
*G01N 15/10* (2006.01)

(52) U.S. Cl.
CPC ..... *G01N 15/1459* (2013.01); *G01N 15/1429* (2013.01); *G01N 2015/1006* (2013.01)

(58) Field of Classification Search
CPC ........... G01N 15/1459; G01N 15/1429; G01N 2015/1006
See application file for complete search history.

(56) References Cited

U.S. PATENT DOCUMENTS

| | | |
|---|---|---|
| 5,909,278 A | 6/1999 | Deka et al. |
| 7,060,992 B1 | 6/2006 | Barney et al. |

(Continued)

FOREIGN PATENT DOCUMENTS

| | | |
|---|---|---|
| WO | 2011128893 | 10/2011 |
| WO | 2014097286 | 6/2014 |

(Continued)

OTHER PUBLICATIONS

Norgren R. M. et al. "Restoration of Profiles from Slit-Scan Flow Cytometry" (1982) IEEE Transactions on Biomedical Engineering, vol. bme-29, No. 2, pp. 101-106 (Feb. 1982) DOI: 10.1109/TBME.1982.325015 Feb. 28, 1982.

(Continued)

*Primary Examiner* — Hugh Maupin
(74) *Attorney, Agent, or Firm* — Mark S. Cohen; Pearl Cohen; Zedek Latzer Baratz LLP

(57) ABSTRACT

Determining total particle emission of a flow cytometer particle by passing laser excitation energy into a generally perpendicular flow cytometer channel element through which a particle passes, the particle adapted to be irradiated and to emit a fluorescent emission responsive to the laser excitation energy, where the fluorescent emission results from a geometrical convolution of a geometrical form of the laser excitation energy and a geometric characteristic of a fluorescent emission of the particle, detecting any of the fluorescent emission, outputting an analog electrical emission, providing multiple time samples of the analog electrical emission, and processing the multiple time samples to calculate a total fluorescent emission of said particle, by determining the extent of said geometric convolution and fitting said time samples to a function of a same extent.

24 Claims, 28 Drawing Sheets

(56) References Cited

U.S. PATENT DOCUMENTS

| | | | |
|---|---|---|---|
| 7,842,512 B2 | 11/2010 | Blatchley et al. | |
| 2002/0122167 A1* | 9/2002 | Riley | G01N 15/1012 |
| | | | 356/28.5 |
| 2005/0009060 A1 | 1/2005 | Beernink et al. | |
| 2007/0057211 A1 | 3/2007 | Bahlman et al. | |
| 2011/0057119 A1 | 3/2011 | Connally | |
| 2011/0235030 A1* | 9/2011 | Champseix | G01N 15/1209 |
| | | | 356/243.2 |
| 2015/0053546 A1* | 2/2015 | Hart | A23L 3/28 |
| | | | 204/158.2 |
| 2016/0326489 A1* | 11/2016 | Durack | C12N 5/0612 |

FOREIGN PATENT DOCUMENTS

| | | |
|---|---|---|
| WO | 2014097287 | 6/2014 |
| WO | 2014143333 | 9/2014 |

OTHER PUBLICATIONS

Gray J. W. et al. "Slit-Scan Flow Cytometryy of Mammalian Chromosomes" (1979) The Journal of Histochemistry and Cytochemistry, vol. 27. No. 1. pp. 441-444 (Jan. 1979) DOI: 10.1177/27.1.374608. Jan. 31, 1979.

Eyal S. et al. "Velocity-independent microfluidic flow cytometry" (2002) Electrophoresis, vol. 23, No. 16, pp. 2653-2657 (published on-line: Aug. 20, 2002) DOI:10.1002/ 1522-2683 (200208)23:16<2653::AID-ELPS2653>3.0. CO;2-H Apr. 20, 2002.

Ayers et al. "Iterative blind deconvolution method and its applications" Optics letters. Jul. 1, 1988;13(7):547-9.

Biggs et al. "Acceleration of iterative image restoration algorithms" Applied optics. Mar. 10, 1997;36(8).1766-75.

Fahmy et al. "A new fast iterative blind deconvolution algorithm" Journal of Signal and Information Processing. Feb. 28, 2012;3(01):98.

Fish et al. "Blind deconvolution by means of the Richardson-Lucy algorithm" JOSA A. Jan. 1, 1995;12(1):58-65.

Holmes et al. "Acceleration of maximum-likelihood image restoration for fluorescence microscopy and other noncoherent imagery" JOSA A. Jun. 1, 1991;8(6):893-907.

Ulmer W. "Inverse problem of linear combinations of Gaussian convolution kernels (deconvolution) and some applications to proton/photon dosimetry and image processing" Inverse Problems. Jun. 4, 2010;26(8):085002.

Ulmer W. "Convolution/deconvolution of generalized Gaussian kernels with applications to proton/photon physics and electron capture of charged particles" In Journal of Physics: Conference Series 2013 (vol. 410, No. 1, p. 012122). IOP Publishing.

Bushnell Tim (2016). 12 Flow Cytometry Terms and Definitions Most Scientists Get Wrong. Retrieved online from https://expertcytometry.com/12-flow-cytometry-terms-and-definitions-most-scientists-get-wrong/. Entry posted May 4, 2016. Expert Cytometry.

Bushnell Tim (2016). What Is a Flow Cytometry Laser and How Flow Cytometry Optics Function. Retrieved from internet at: https://expertcytometry.com/what-is-a-flow-cytometry-laser-how-flow-cytomtery-optics-function/. Entry posted May 4, 2016. Expert Cytometry.

European Search Report dated Feb. 13, 2019 for corresponding European Patent Application No. EP16799468.0, filed May 23, 2016.

Grogan, W. M., Collins, J. M., & Collins, J. (1990). Guide to flow cytometry methods. CRC Press. Extract 15.8 Slit-Scan Systems.

Introduction to Flow Cytometry: A Learning Guide (2002). Retrieved from internet at: https://www.bu.edu/flow-cytometry/files/2010/10/BD-Flow-Cytom-Learning-Guide.pdf. Becton, Dickinson and Company, 1-52.

Nolan, J. P., Condello, D., Duggan, E., Naivar, M., & Novo, D. (2013). Visible and near infrared fluorescence spectral flow cytometry. Cytometry Part A, 83(3), 253-264.

Optics of a Flow Cytometer. Retrieved from internet at: https://www.thermofisher.com/il/en/home/life-science/cell-analysis/cell-analysis-learning-center/molecular-probes-school-of-fluorescence/flow-cytometry-basics/flow-cytometry-fundamentals/optics-flow-cytometer.html. Thermo Fisher Scientific.

Rowley Tom (2012). Flow Cytometry—A Survey and the Basics. Retrieved from internet at: https://www.labome.com/method/Flow-Cytometry-A-Survey-and-the-Basics.html. Labome.

The Fourier Transform (What you need to know) (2007). The School of Physics and Astronomy, The University of Edinburgh, pp. 1-31. Retrieved on-line: https://www2.ph.ed.ac.uk/~wjh/teaching/Fourier/documents/booklet.pdf.

* cited by examiner

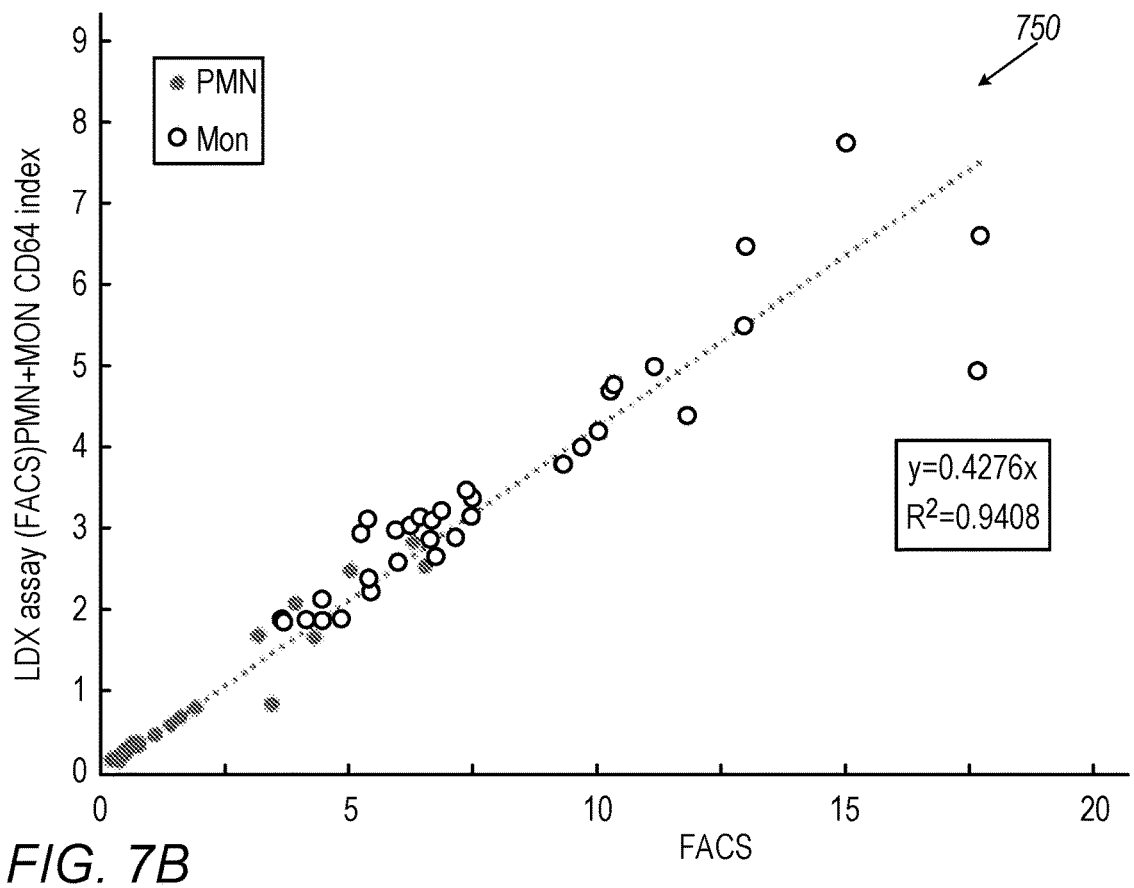
FIG. 7B
FIG. 8A
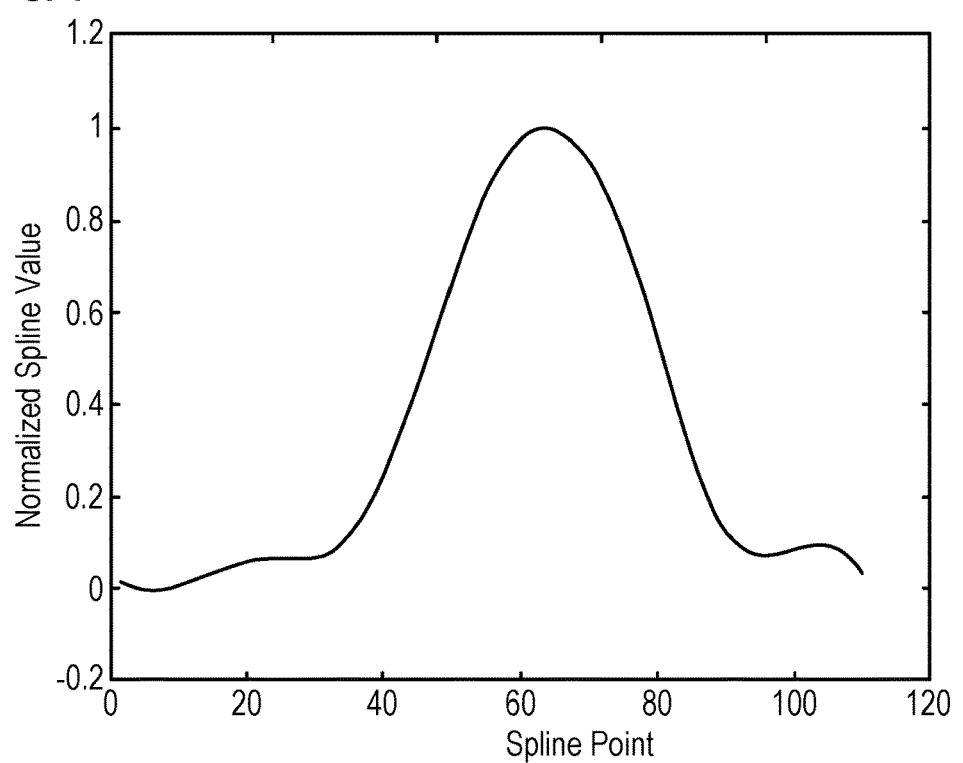

SYSTEM AND APPARATUS FOR BLIND DECONVOLUTION OF FLOW CYTOMETER PARTICLE EMISSION

CROSS-REFERENCE TO RELATED APPLICATIONS

This application is a U.S. National Phase Application under 35 U.S.C. 371 of International Application No. PCT/IL2016/000110, which has an international filing date of May 23, 2016, and which claims the priority benefit of U.S. Provisional Patent Application No. 62/167,524, filed May 28, 2015, the description of which is hereby incorporated by reference.

COMPUTER PROGRAM LISTING STATEMENT

The instant application contains a Computer Program Listing Appendix which has been submitted electronically in ASCII format and is hereby incorporated by reference in its entirety. Said ASCII copy, created on Oct. 17, 2019, is named P-583297-US-COMPUTER-PROGRAM-LISTING-APPENDIX-17OCT19.txt and is 40 KB in size.

FIELD OF THE INVENTION

The present invention relates generally to signal deconvolution methods, and more specifically to methods and apparatus for deconvolution of signals from a flow cytometer.

BACKGROUND OF THE INVENTION

Flow cytometry technology is used in the diagnosis of health disorders, especially blood cancers. Typically, cells from a blood sample are suspended in a stream of carrier fluid and passed one by one through a narrow channel in an apparatus, while impinging a laser on them and detecting at least one output in an electronic detection apparatus. Flow cytometers are expensive, labor intensive and cumbersome. They are only normally only available at large institutions. Moreover, the electronic detection apparatus is not always able to quantify the outputs. Many flow cytometry tests provide inaccurate results and sometimes false positive results. Additionally, the analysis of outputs by the electronic detection apparatus often includes significant noise and background disturbance.

Some attempts have been made to provide desk-top portable, automatic flow cytometer systems. WO 2011128893 discloses a device, system and method for rapid determination of a medical condition. WO 2011128893 provides a system including a disposable cartridge adapted to receive a volume of a body fluid, the cartridge comprising a plurality of sections, at least one of the sections adapted to react at least one reactant with the bodily fluid to form a pretreated sample; and an optics unit comprising at least one excitation illumination adapted to convey radiation to the pre-treated sample, at least one multi-spectral emission detector and at least one of a photon counter and an integrator, wherein the at least one excitation illumination and the at least one multi-spectral emission detector are disposed on the same side of the cartridge; and wherein the optics unit is adapted to detect a plurality of spectrally distinct signals generated by interaction of the radiation and the pre-treated sample in the cartridge, thereby determining said medical condition.

US20070057211 discloses multifocal imaging systems and methods. The multifocal multiphoton imaging system has a signal to noise ratio (SNR) that is reduced by over an order of magnitude at imaging depth equal to twice the mean free path scattering length of the specimen. An MMM system, is based on an area detector, such as a multianode photomultiplier tube (MAPMT), which is optimized for high-speed tissue imaging. The specimen is raster-scanned with an array of excitation light beams. The emission photons from the array of excitation foci are collected simultaneously by a MAPMT and the signals from each anode are detected using high sensitivity, low noise single photon counting circuits. An image is formed by the temporal encoding of the integrated signal with a raster scanning pattern.

A deconvolution procedure taking account of the spatial distribution and the raster temporal encoding of collected photons can be used to improve decay coefficient. We demonstrate MAPMT-based MMM can provide significantly better contrast than CCD-based existing systems. This includes a deconvolution procedure taking account of the spatial distribution and the images by a deconvoluting pixel values with a scattering correction function.

US2005009060A provides systems for multiplexed multitarget screening of cell populations having one or more wild type or mutated ligand targets and measuring cell responses to ligands using high throughput screening techniques, including flow cytometry (FCM). The method includes the steps of: 1) developing cell populations to be screened; 2) staining cell populations using one or more fluorochromes to yield a distinct excitation/emission signature for each cell population; 3) combining labelled cell populations into a single mixed suspension; 4) analyzing populations to resolve them on the basis of their unique signature; and 5) resolving individual populations and deconvoluting data to extract meaningful information about populations.

U.S. Pat. No. 5,909,278 describes time-resolved fluorescence decay measurements for flowing particles. An apparatus and method for the measurement and analysis of fluorescence for individual cells and particles in flow are described, wherein the rapid measurement capabilities of flow cytometry and the robust measurement and analysis procedures of time-domain fluorescence lifetime spectroscopy are combined. A pulse-modulated cw laser is employed for excitation of the particles. The characteristics and the repetition rate of the excitation pulses can be readily adjusted to accommodate for fluorescence decays having a wide range of lifetimes.

U.S. Pat. No. 7,842,512 discloses a method for photochemical reactor characterization includes an application of using dyed microspheres exposed to UV irradiation under a collimated-beam system. Particle specific fluorescence intensity measurements are conducted using samples form the collimated beam and flow-through reactor results using flow cytometry.

A numerical model may be used to simulate the behavior of the reactor system to provide a particle-tracking algorithm to interrogate the flow and intensity field simulations for purposes of developing a particle specific estimate of the dose delivery. A method for measuring UV dose distribution delivery in photochemical reactors is provided that includes introducing microspheres labeled with a photochemically-active compound in a UV reactor.

The labeled microspheres are harvested downstream of the irradiated zone of a UV reactor and exposed to UV irradiation under a collimated beam of UV irradiation. The method further includes quantifying a UV dose-response behavior, conducting fluorescence intensity measurement on the labeled microspheres from the UV reactor, and developing an estimate of a dose distribution delivered by a UV reactor based on the numerical deconvolution of the sum of the UV dose response behavior and fluorescent intensity of exposed microspheres.

There still remains a need to provide improved flow cytometer output analyses and further to provide apparatus for efficient and accurate output analysis that accurately determines the emission of individual particles in a flow cytometer stream.

SUMMARY OF THE INVENTION

It is an object of some aspects of the present invention to provide improved determination of total particle fluorescent emission by means of deconvolution methods and apparatus for use in flow cytometry.

In some embodiments of the present invention, improved methods and systems are provided for blind deconvolution of flow cytometer particle emissions.

In other embodiments of the present invention, a method and system is described for providing a method for detecting the actual particle emission from a particle excited by a known or to be determined excitation pattern. Typically, the emission from a particle in a flow cytometer is the result of the geometrical convolution of the excitation pattern and the emission characteristics of the particle. Typical emission measurement techniques measure the result of this convolution, but not the actual particle emission.

Further embodiments of the present invention provide deconvolution methods applied to flow cytometry systems such as, but not limited to those disclosed in WO 2011128893, WO2014/097286 and WO2014/097287.

There is thus provided according to an embodiment of the present invention, a system for determining a total particle emission of a flow cytometer particle, the system including;
an apparatus adapted to pass a laser excitation energy into a generally perpendicular flow cytometer channel element through which a particle passes, the particle being adapted to be irradiated by the apparatus and to emit at least one fluorescent emission responsive to the laser excitation energy, wherein the at least one fluorescent emission results from a geometrical convolution of a geometrical form of both;
 i. the laser excitation energy; and
 ii. a geometric characteristic of at least one fluorescent emission of the particle;
 b. an analog emission detector adapted to detect at least some of the at least one fluorescent emission and to output an analog electrical emission;
 c. a digital sampler adapted to provide multiple time samples of the analog electrical emission; and
 d. a processor, adapted to process the multiple time samples and to calculate a total fluorescent emission of said particle, by determining the extent of said geometric convolution and fitting said time samples to a function of a same extent.

Additionally, according to an embodiment of the present invention, the flow cytometer channel element is adapted to pass a plurality of particles through the channel element in single file.

Furthermore, according to an embodiment of the present invention, a location of the multiple time samples of the analog electrical emission is a function of a velocity of the particle.

Moreover, according to an embodiment of the present invention, the digital sampler is adapted to sample the analog electrical emission at fixed time intervals.

Further, according to an embodiment of the present invention, the plurality of particles include particles of different sizes and shapes.

Yet further, according to an embodiment of the present invention, the digital sampler is adapted to sample the analog electrical emission from the plurality of the particles.

Notably, according to an embodiment of the present invention, the flow cytometer channel element is adapted to pass the plurality of particles without a sheath fluid.

Additionally, according to an embodiment of the present invention, a result of the convolution associated with each individual particle of the plurality of the particles is a function of a velocity of each the particle in the channel.

Importantly, according to an embodiment of the present invention, the total fluorescent emission of the particle is obtained from a deconvolution.

Furthermore, according to an embodiment of the present invention, the deconvolution is a ratio of an integral of the geometric convolution with respect to an integral of the laser excitation energy.

Moreover, according to some embodiments of the present invention, the total fluorescent emission of the particle is determined at least in part according to at least one of the group consisting of an average of convolution to an integral of convolution for a known particle size, a maximum of samples to an integral of convolution for a known particle size and a sample sum to an integral of convolution of a known particle size.

Further, according to an embodiment of the present invention, the processor is further adapted to generate models of the geometric convolution as a function of a number of the multiple time samples.

Yet further, according to an embodiment of the present invention, the processor is further adapted to compare the geometric convolution to a normalized model.

Additionally, according to an embodiment of the present invention, the processor is further adapted to determine the extent of the geometric convolution from a measurement of a size of the particle.

Moreover, according to an embodiment of the present invention, the processor is further adapted to determine the extent of the geometric convolution from a measurement of a velocity of the particle.

There is thus provided according to another embodiment of the present invention, a method for determining a total particle emission of a flow cytometer particle, the method including;
 a. impinging a laser excitation energy onto a particle moving generally perpendicularly thereto, to induce the particle to emit at least one fluorescent emission responsive to the laser excitation energy, wherein the at least one fluorescent emission results from a geometrical convolution of a geometrical form of both;
  i. the laser excitation energy; and
  ii. a geometric characteristic of at least one fluorescent emission of the particle;
 b. detecting at least some of the at least one fluorescent emission thereby outputting an analog electrical emission;
 c. providing multiple time samples of the analog electrical emission; and
 d. processing the multiple time samples to calculate a total fluorescent emission of the particle, by determining the extent of the geometric convolution and fitting the time samples to a function of a same extent.

Further, according to an embodiment of the present invention, the impinging step further includes passing a plurality of particles moving generally perpendicularly thereto in a single file.

Additionally, according to an embodiment of the present invention, a location of the multiple time samples of the analog electrical emission is a function of a velocity of the particle.

Furthermore, according to an embodiment of the present invention, the provision step includes sampling the analog electrical emission at fixed time intervals.

Yet further, according to an embodiment of the present invention, the plurality of particles includes particles of different sizes and shapes.

Moreover, according to an embodiment of the present invention, the provision step further includes providing multiple time samples of the analog electrical emission from the plurality of the particles.

Additionally, according to an embodiment of the present invention, the passing the plurality of the particles includes passing the plurality of the particles without a sheath fluid.

Further, according to an embodiment of the present invention, a result of the convolution associated with each individual particle of the plurality of the particles is a function of a velocity of each the particle.

Additionally, according to an embodiment of the present invention, the total fluorescent emission of the particle is obtained from a deconvolution.

Importantly, according to an embodiment of the present invention, the deconvolution is a ratio of an integral of the geometric convolution with respect to an integral of the laser excitation energy.

Additionally, according to some embodiments of the present invention, the total fluorescent emission of the particle is determined at least in part according to at least one of the group consisting of a ratio of an average of convolution to an integral of convolution for a known particle size, a maximum of samples to an integral of convolution for a known particle size and a sample sum to an integral of convolution of a known particle size.

Moreover, according to an embodiment of the present invention, the processing step further includes generating models of the geometric convolution as a function of a number of the multiple time samples.

Additionally, according to an embodiment of the present invention the processing step further includes comparing the geometric convolution to a normalized model.

Further, according to an embodiment of the present invention, the processing step further comprises determining the extent of the geometric convolution from a measurement of a size of the particle.

Yet further, according to an embodiment of the present invention, the processing step further comprises determining the extent of the geometric convolution from a measurement of a velocity of the particle.

The present invention further provides methods and systems for deconvolution of a flow cytometer particle output, the system including an apparatus adapted to pass a laser energy into a generally perpendicular flow cytometer channel element through which a particle passes, the particle being adapted to be irradiated by the apparatus and to emit at least one fluorescent emission responsive to the laser energy, an analog emission detector adapted to detect at least some of the at least one fluorescent emission, a digital sampler adapted to provide multiple time samples of said analog detector output of said emission from an irradiated particle in said flow cytometer element and a processor, adapted to detect the at least one output signal and to blindly deconvolve the at least one output thereby quantifying actual individual particle emission.

If the particle is completely excited by the excitation pattern and sufficient samples are taken, the conventional prior art technique is to choose the maximum output of the convolution result to represent the total particle emission. While this generally provides an estimate of the particle emission it neglects all the rest of the samples that would help to provide a more precise measurement of the particle intensity and does not properly account for non-uniform excitation.

If the particle is not completely excited by the excitation pattern, then any method that does not use all of the samples of the geometrical convolution result will perforce not accurately represent the total particle emission. Naïve addition of all the sample values over-estimates the true particle emission, while normalizing this sum by the total number of samples simply provides an average of the geometrical convolution—not the true particle emission intensity. Further, this normalization of the prior art methods, depends on the number of samples that approaches the true average value only as the number of samples approaches infinity.

In contrast to the prior art limitations described hereinbelow, the present invention provides a method for deconvolution that extracts the true particle emission from the sampled output of the geometrical convolution. The Matlab example shown below simulates the physical geometrical convolution of an excitation pattern with an emission pattern to yield a two-dimensional convolution. Sampling of this two-dimensional pattern in time yields a one dimensional signal. This sampling is equivalent to projecting the two-dimensional convolution output onto one dimension as shown in the simulation below. This one dimensional pattern can be achieved by a one dimensional convolution of the projections of the excitation and emission, also as shown below. Thus, to extract the one-dimensional projection of the particle emission one simply deconvolves the actual particle emission from the convolution result using the known or estimated excitation pattern.

Advantages of this method, unobtainable by currently prior art methodology, and some of its additional properties are the following:
1. Physical mathematical operation inverted by computation;
2. Determines particle size;
3. Works with excitation smaller or larger than particle;
4. Decreasing excitation window increases signal to background ratio:
   a. Signal proportional to particle area; and
   b. Background proportional to excited channel volume;
5. Convolution kernel
   a. Determined independently
   b. Determined from test particles using "blind deconvolution"
6. Similar to image de-blurring.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration of the physical elements of a convolution model, in accordance with an embodiment of the present invention;

FIG. 2 is a simplified schematic illustration of a method for deconvolving the total particle emission from the signals obtained from the physical elements of a convolution model, in accordance with an embodiment of the present invention;

FIG. 3 is a simplified schematic illustration of a variation of a beam width of a Gaussian laser beam, in accordance with an embodiment of the present invention;

FIG. 4 is a plot of a beam width as a function of a distance from a waist for a two micron beam waist, in accordance with an embodiment of the present invention;

FIG. 5 is a plot of a beam width as a function of a distance from a waist for a 2.5 micron beam waist, in accordance with an embodiment of the present invention;

FIG. 6 is a plot of a beam width as a function of a distance from a waist for a three micron beam waist, in accordance with an embodiment of the present invention;

FIG. 7A is a plot of a correlation of a CD64 assay results for PMN (neutrophils) of the present invention versus a Trillium LK-12 assay, in accordance with an embodiment of the present invention;

FIG. 7B is a plot of a correlation of a CD64 assay results for PMN (neutrophils) and Mon (monocytes) of the present invention versus a Trillium LK-12 assay, in accordance with an embodiment of the present invention;

FIG. 8A is a normalized spline plot for Event 1 Waveband2 (11 sample points). Fitted spline uses 10 points per sample point;

FIG. 8B is a normalized spline plot for Event 2 Waveband2 (16 sample points). Fitted spline uses 10 points per sample point;

FIG. 9 is a simplified schematic illustration of a method for deconvolving the total particle emission from the signals obtained from the physical elements of a convolution model, in accordance with an embodiment of the present invention specialized for the two real data events;

Figure 10A:
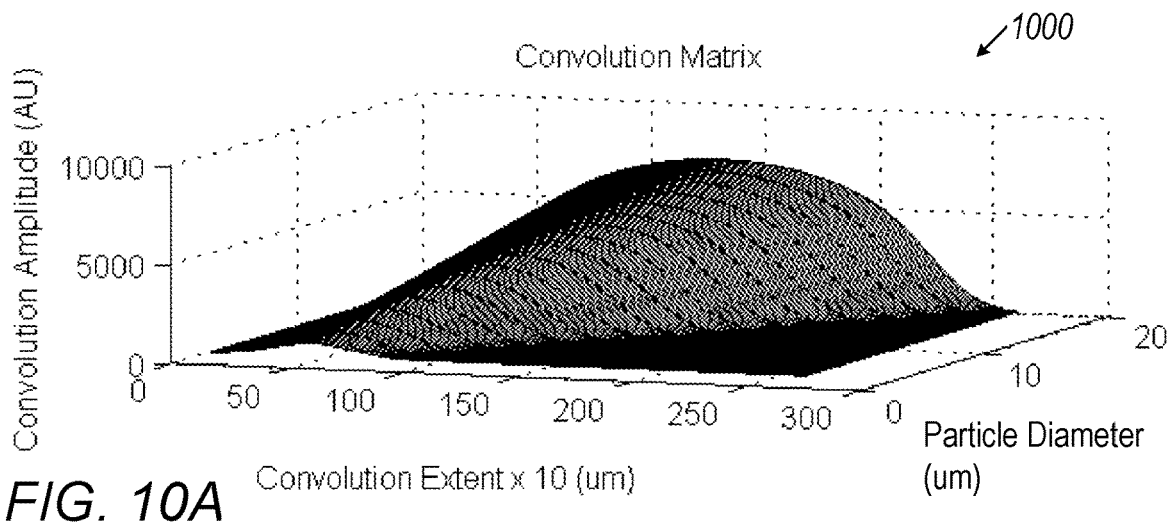
Figure 10B:
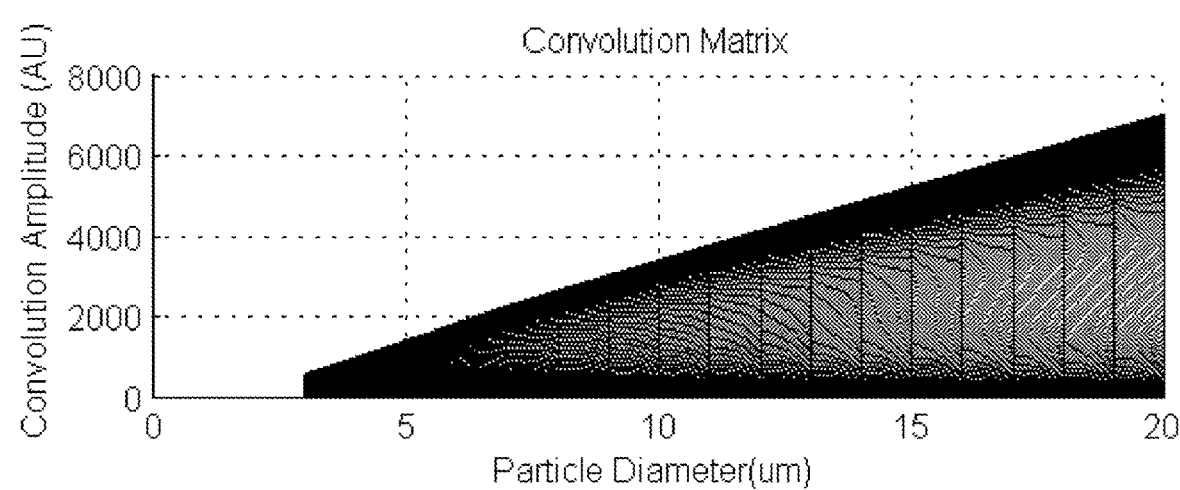
Figure 11A:
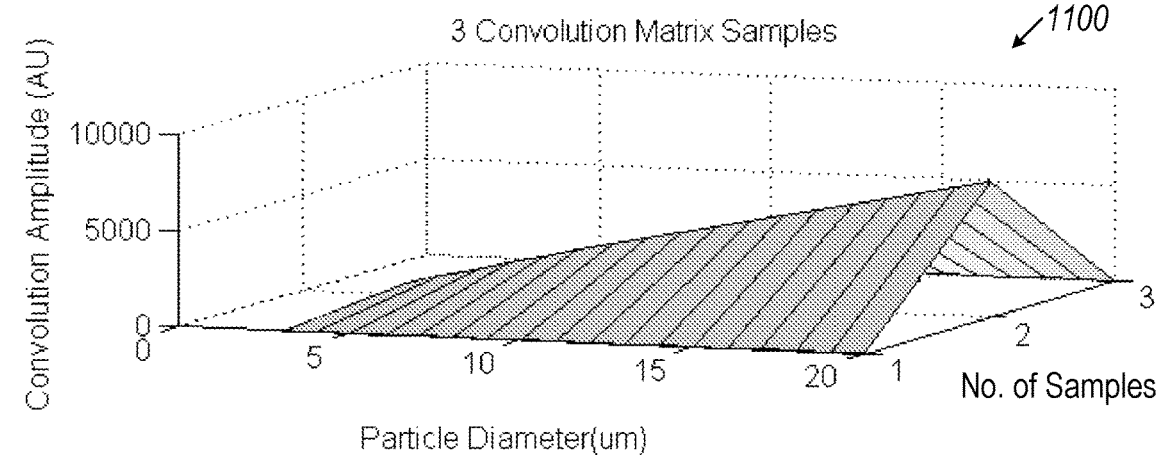
Figure 11B:
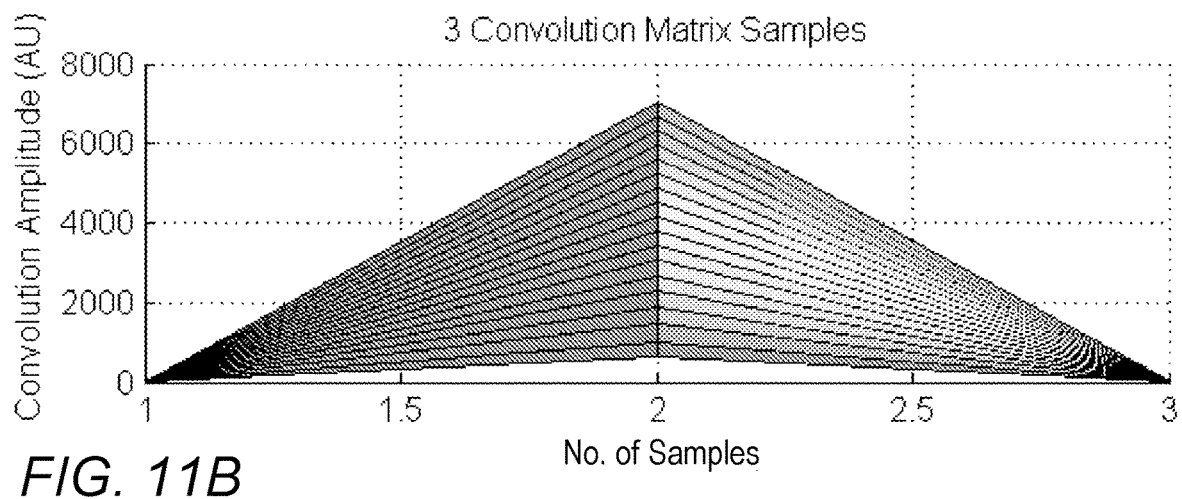
Figure 12A:
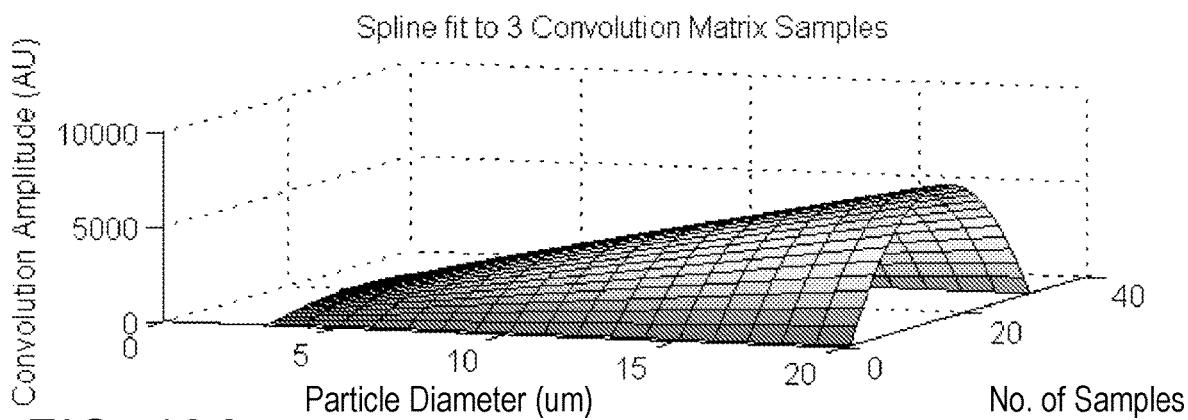
Figure 12B:
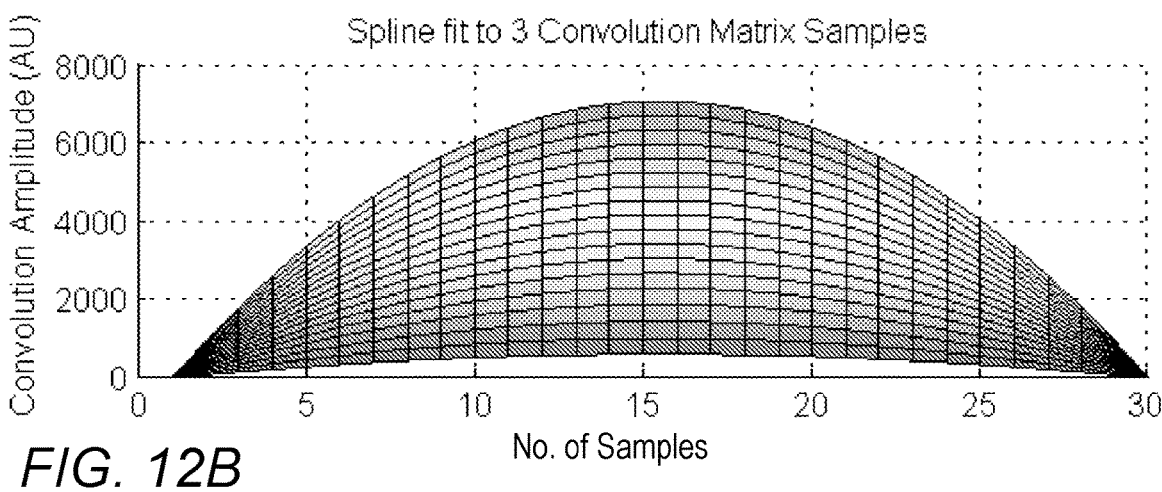
Figure 13A:
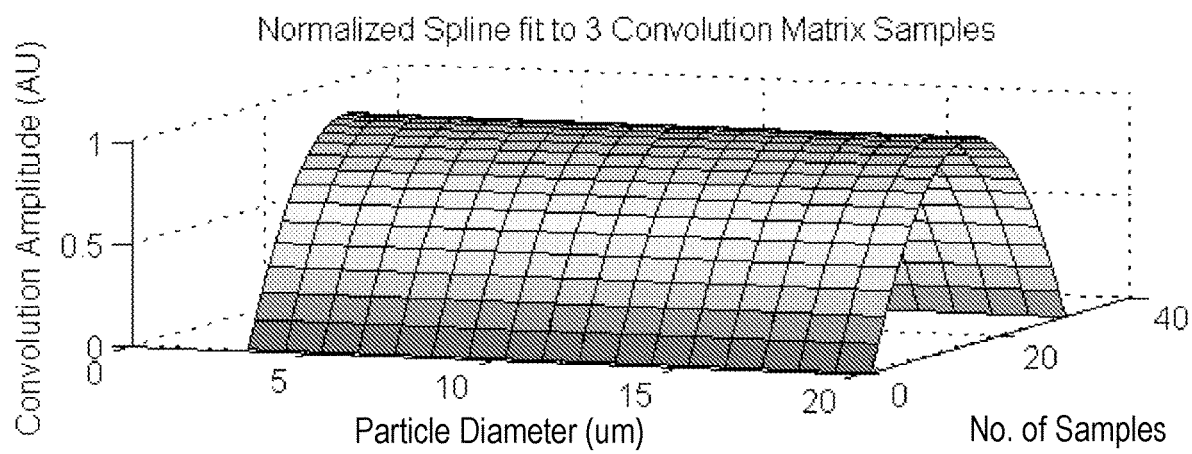
Figure 13B:
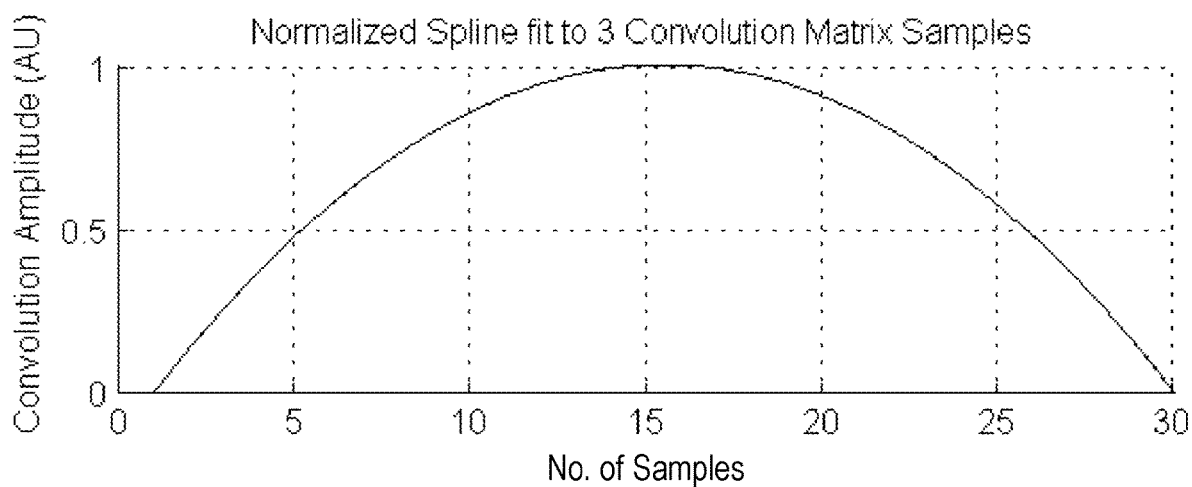
Figure 14A:
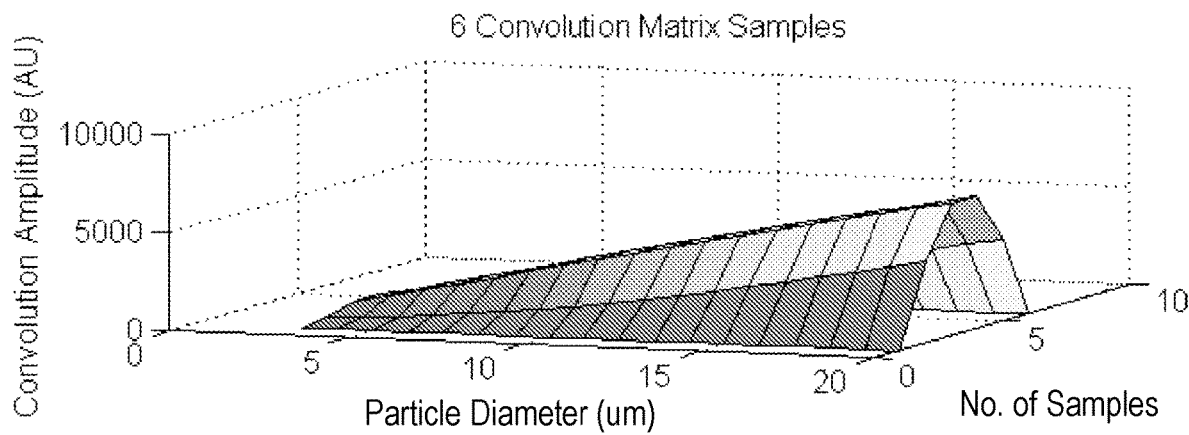
Figure 14B:
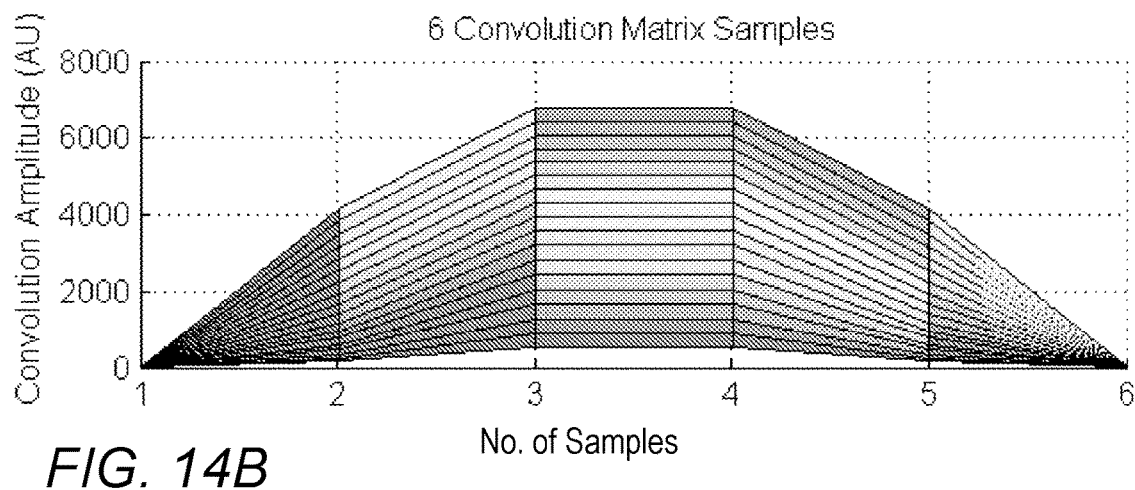
Figure 15A:
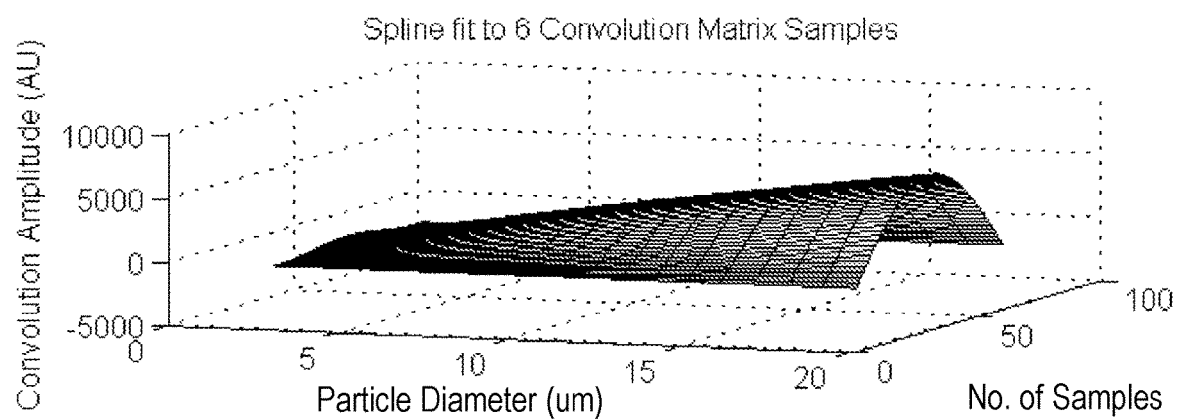
Figure 15B:
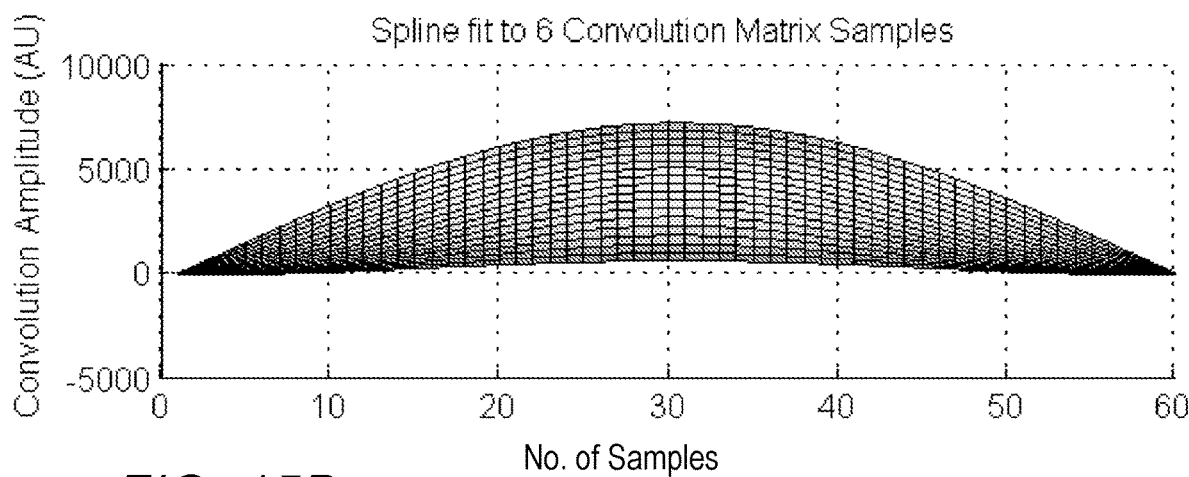

FIG. 10A is a reference convolution matrices plot for fixed excitation and varying particle diameters displayed as side-by-side surface plots showing the variation of amplitude and extent as a function of particle size in accordance with an embodiment of the present invention;

FIG. 10B is a reference convolution matrices plot for fixed excitation and varying particle diameters displayed as side-by-side surface plots showing the variation of amplitude and extent as a function of particle size viewed along the Particle Diameter axis in accordance with an embodiment of the present invention;

FIG. 11A is a plot of 3 samples from reference convolution matrices for fixed excitation and varying particle diameters showing the variation of amplitude and extent as a function of particle size in accordance with an embodiment of the present invention;

FIG. 11B is a plot of 3 Samples from reference convolution matrices for fixed excitation and varying particle diameters showing the variation of amplitude and extent as a function of particle size viewed from the No. of Samples axis in accordance with an embodiment of the present invention;

FIG. 12A is a plot of a spline fit to 3 samples from reference convolution matrices for fixed excitation and varying particle diameters showing the variation of amplitude and extent as a function of particle size in accordance with an embodiment of the present invention;

FIG. 12B is a plot of a spline fit to 3 Samples from Reference Convolution Matrices for fixed excitation and varying particle diameters showing the variation of amplitude and extent as a function of particle size viewed from the No. of Samples axis in accordance with an embodiment of the present invention;

FIG. 13A is a plot of a normalized spline fit to 3 samples from reference convolution matrices for fixed excitation and varying particle diameters showing variation of amplitude and extent as a function of particle size in accordance with an embodiment of the present invention;

FIG. 13B is a plot of a normalized spline fit to 3 samples from reference convolution matrices for fixed excitation and varying particle diameters showing variation of amplitude and extent as a function of particle size viewed from the No. of Samples axis in accordance with an embodiment of the present invention;

FIG. 14A is a plot of 6 samples from reference convolution matrices for fixed excitation and varying particle diameters showing the variation of amplitude and extent as a function of particle size in accordance with an embodiment of the present invention;

FIG. 14B is a plot of 6 samples from reference convolution matrices for fixed excitation and varying particle diameters showing the variation of amplitude and extent as a function of particle size viewed from the No. of Samples axis in accordance with an embodiment of the present invention;

FIG. 15A is a plot of a spline fit to 6 samples from reference convolution matrices for fixed excitation and varying particle diameters showing the variation of amplitude and extent as a function of particle size in accordance with an embodiment of the present invention;

FIG. 15B is a plot of a spline fit to 6 samples from reference convolution matrices for fixed excitation and varying particle diameters showing the variation of amplitude and extent as a function of particle size viewed from the No. of Samples axis.

Figure 16A:
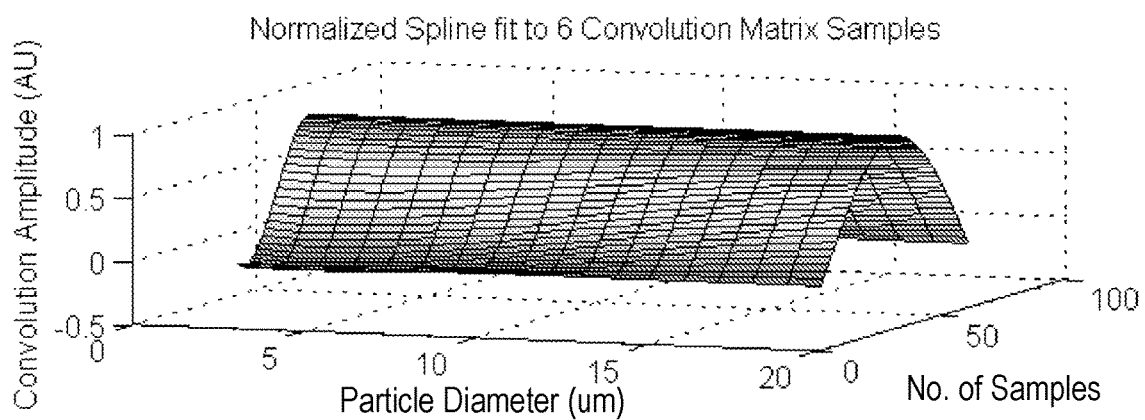
Figure 16B:
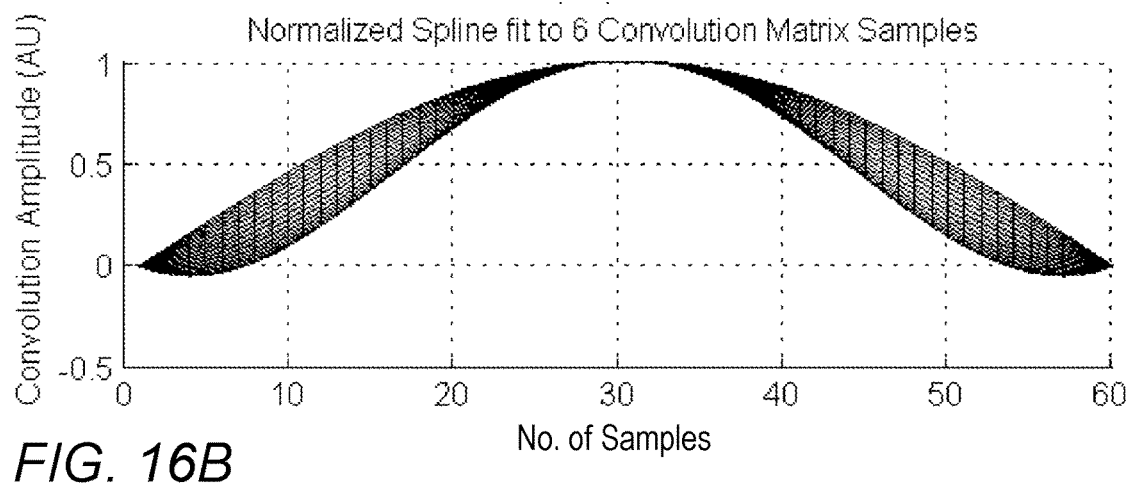
Figure 17A:
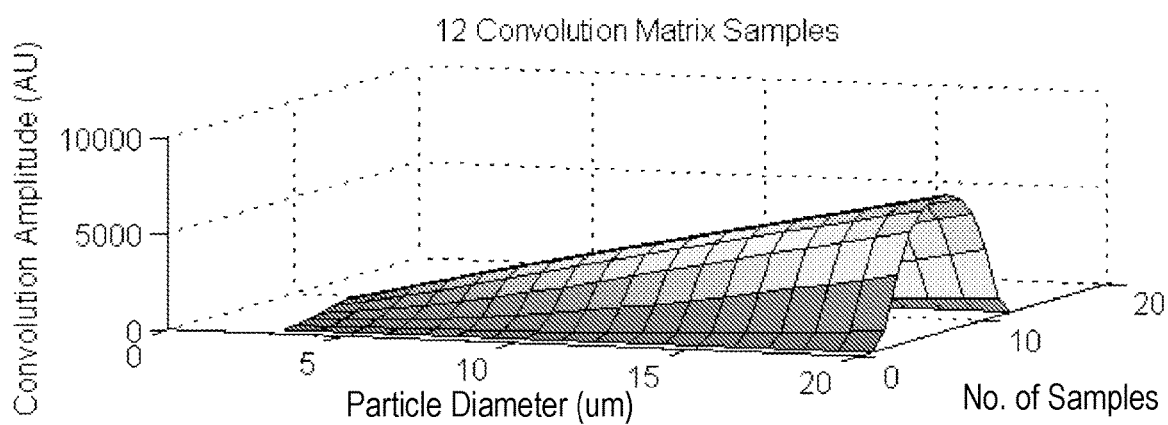
Figure 17B:
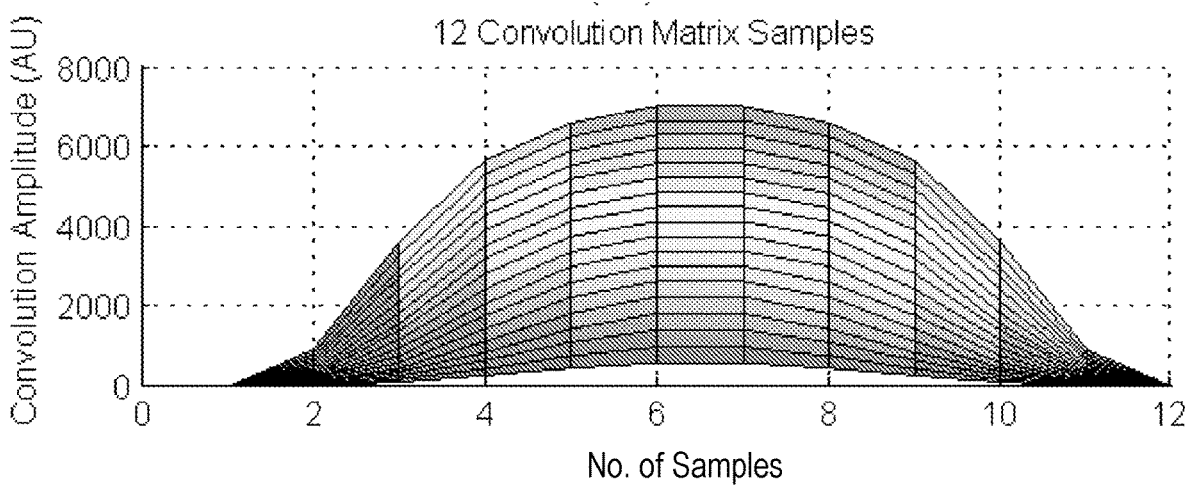
Figure 18A:
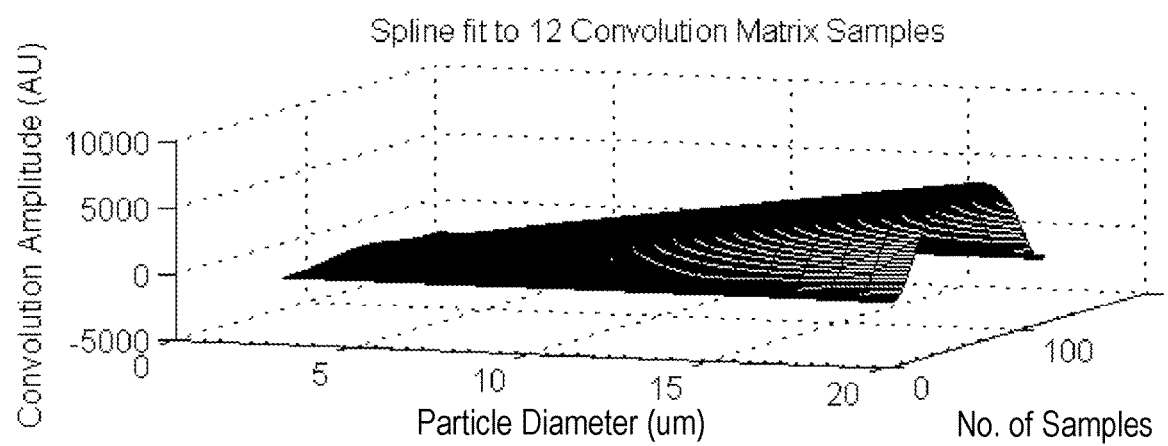
Figure 18B:
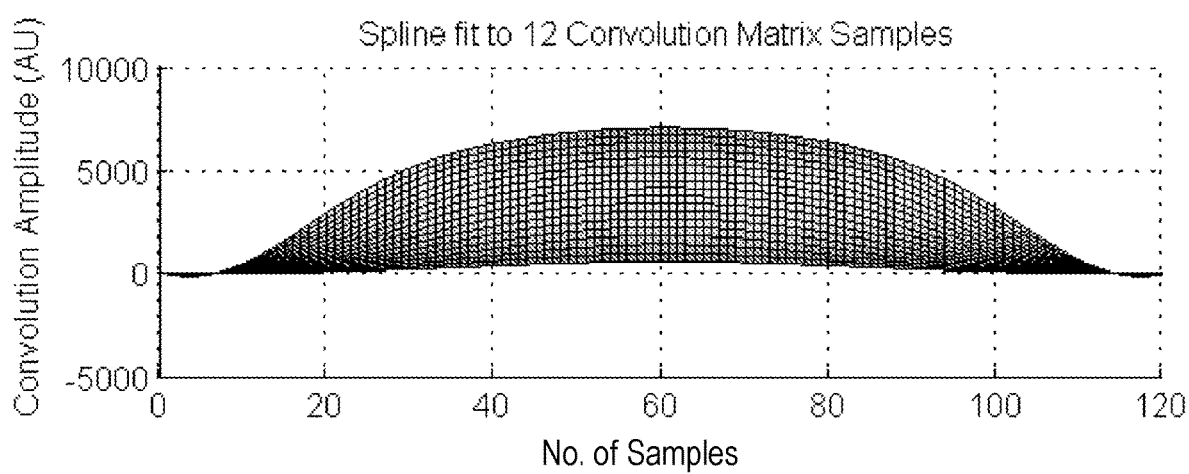
Figure 19A:
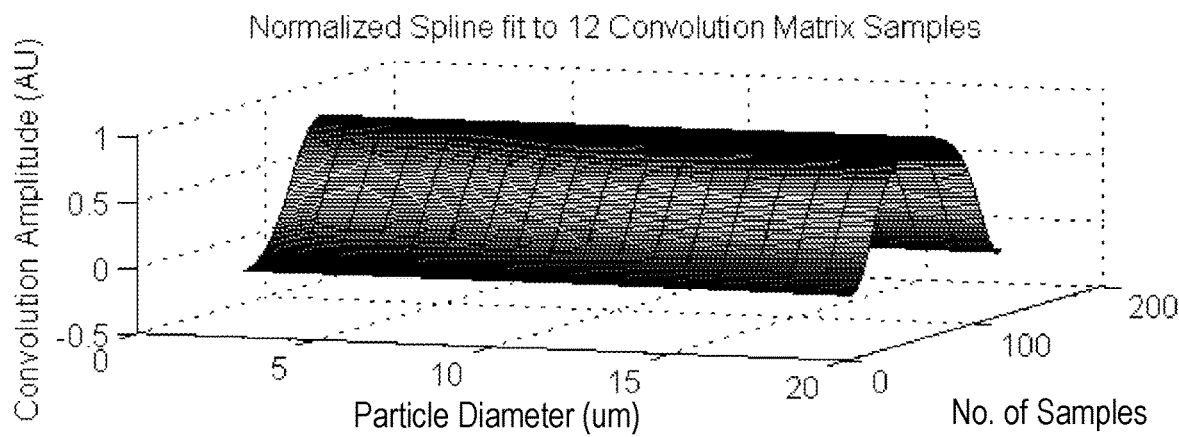
Figure 19B:
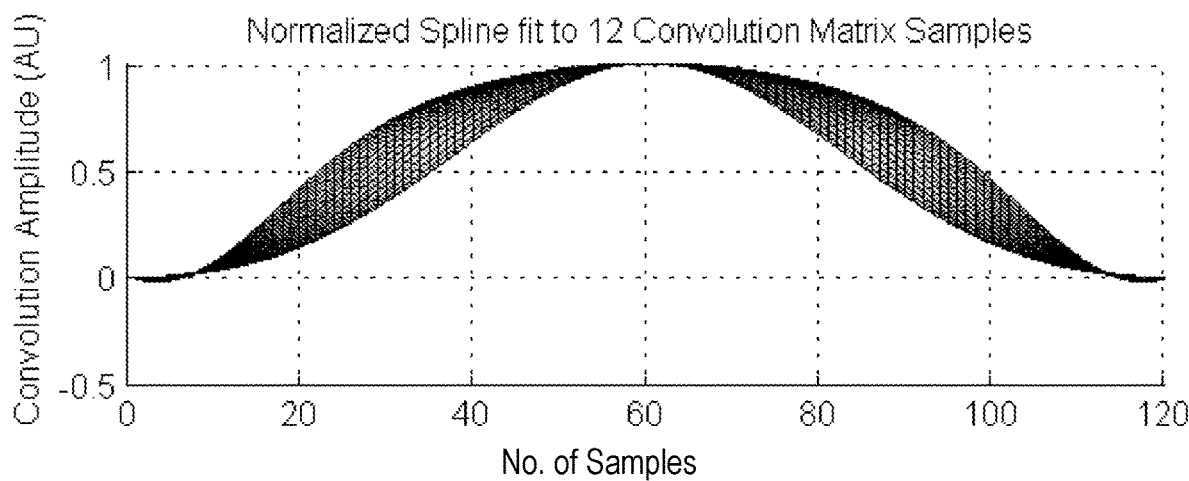
Figure 20A:
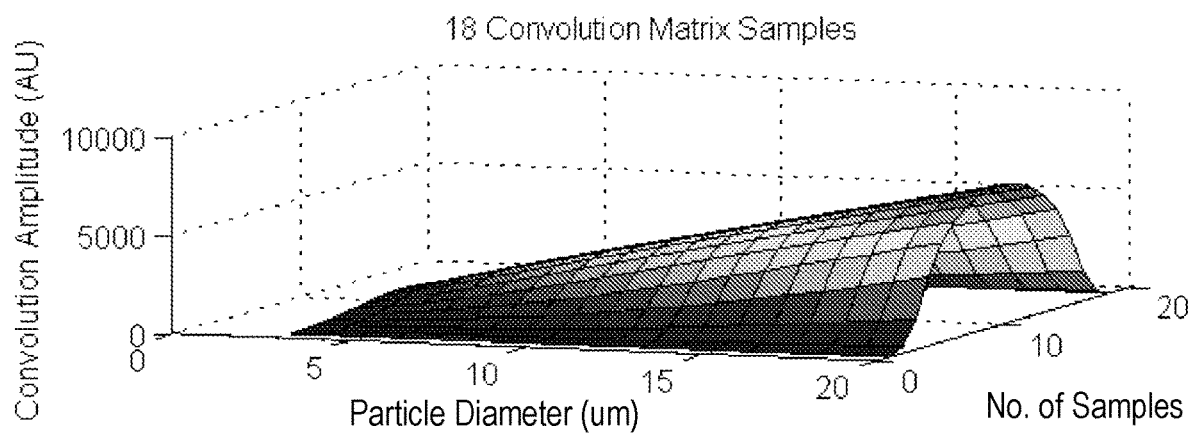
Figure 20B:
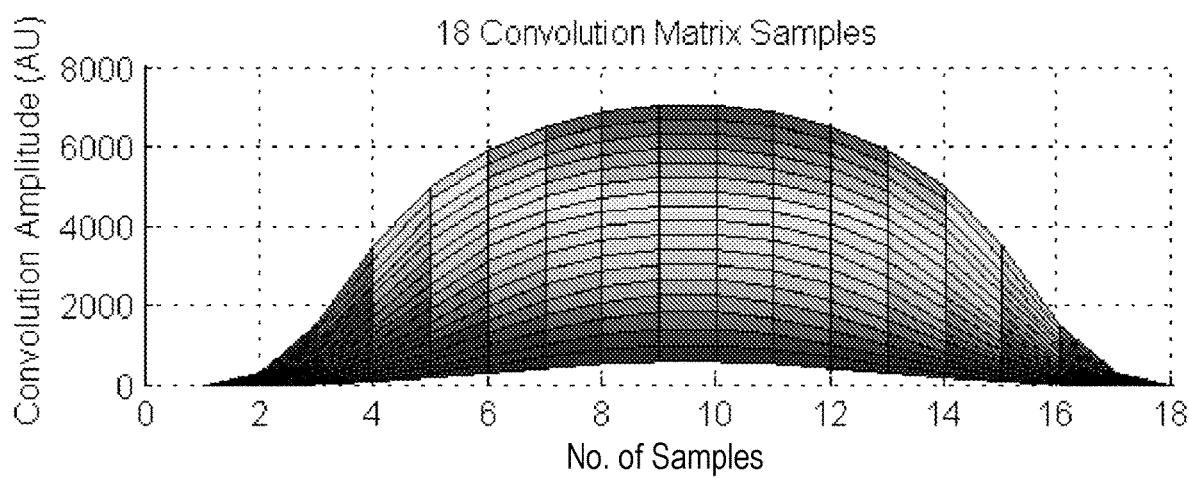
Figure 21A:
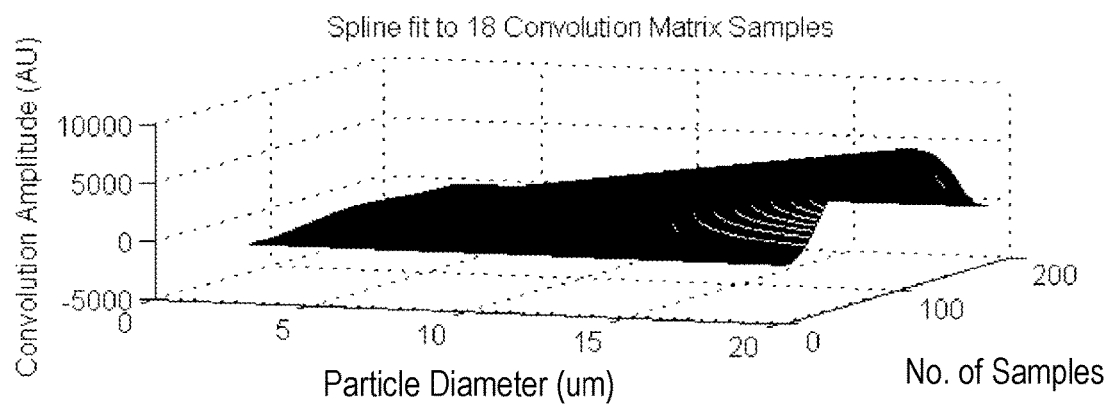
Figure 21B:
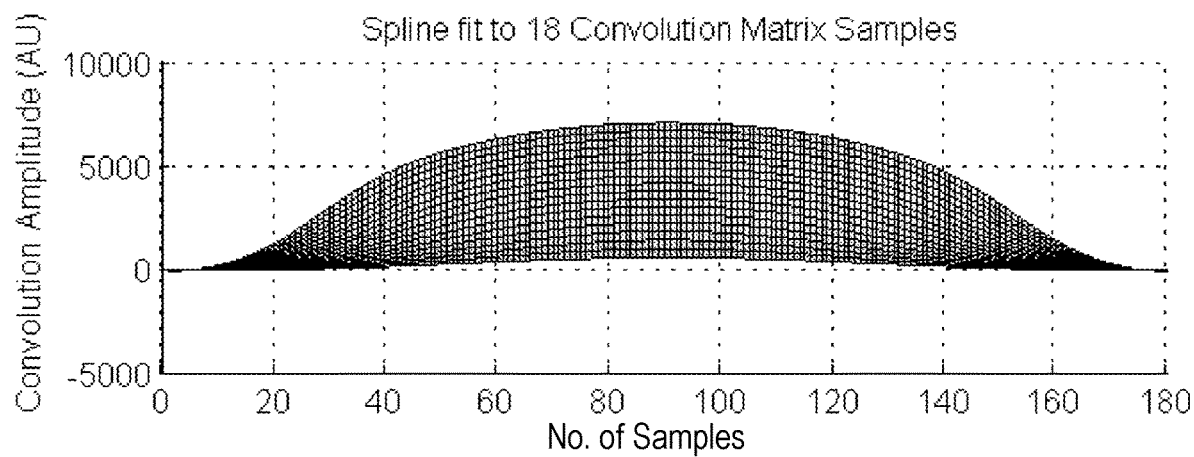
Figure 22A:
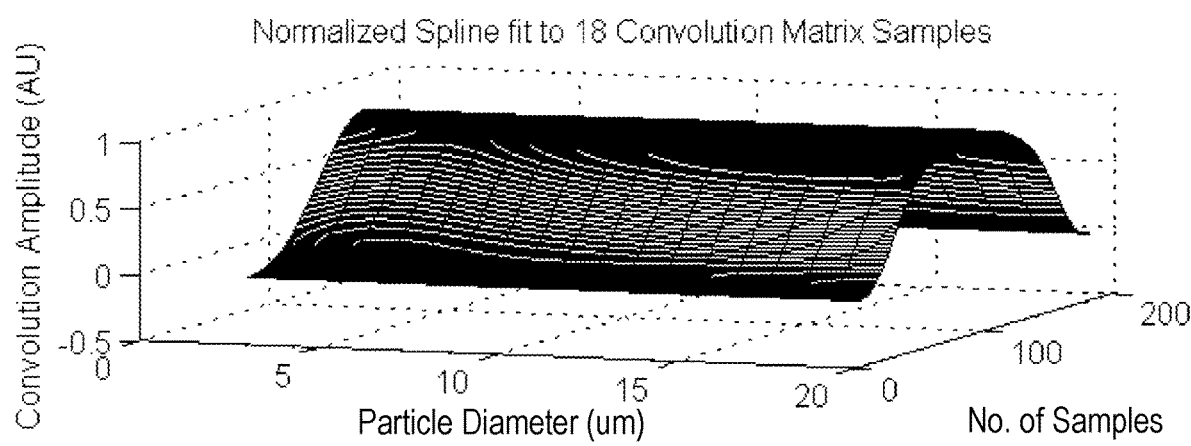
Figure 22B:
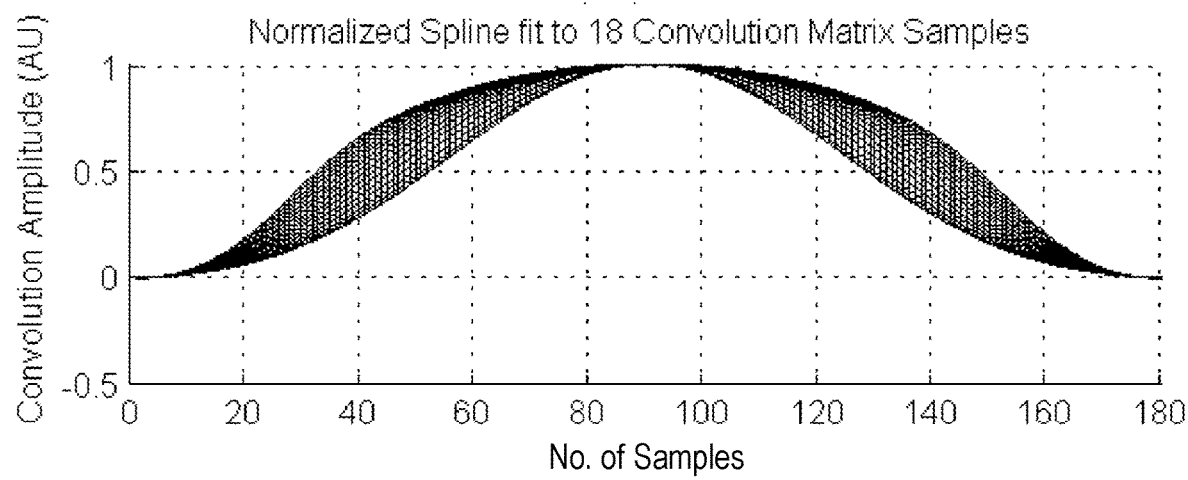
Figure 23A:
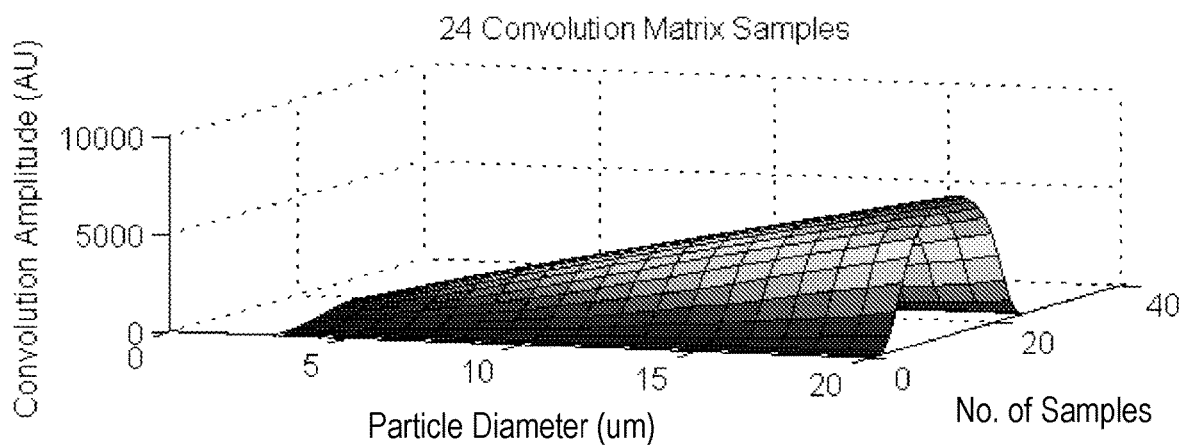
Figure 23B:
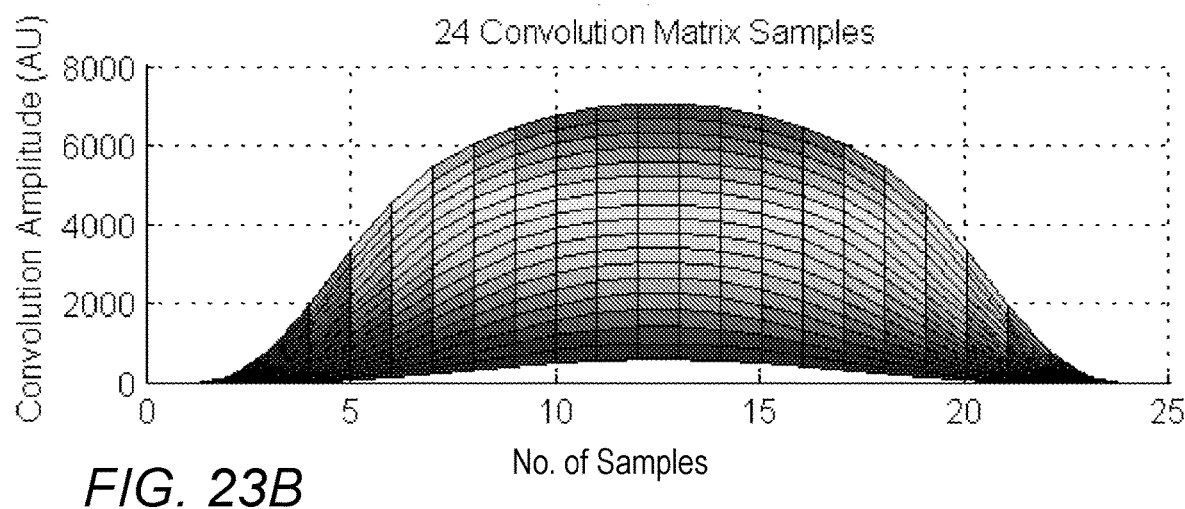
Figure 24A:
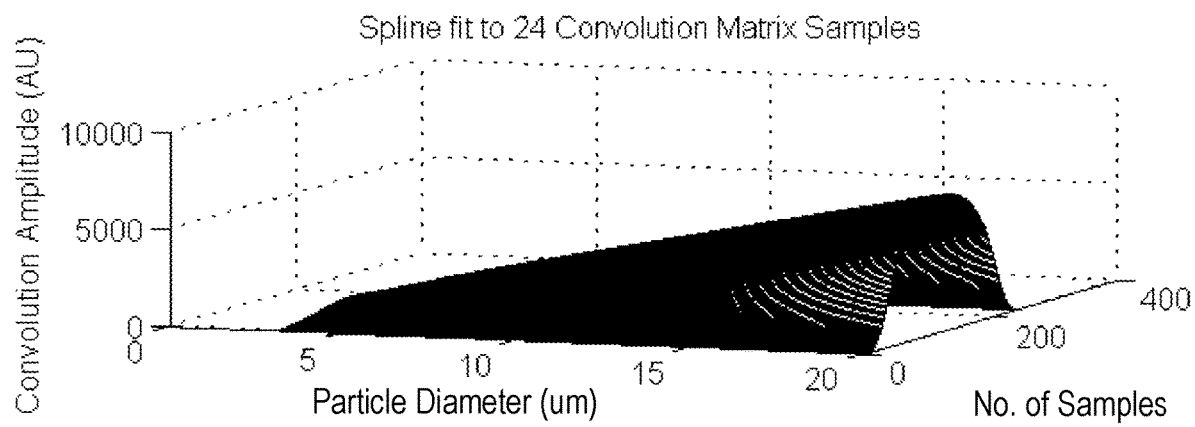
Figure 24B:
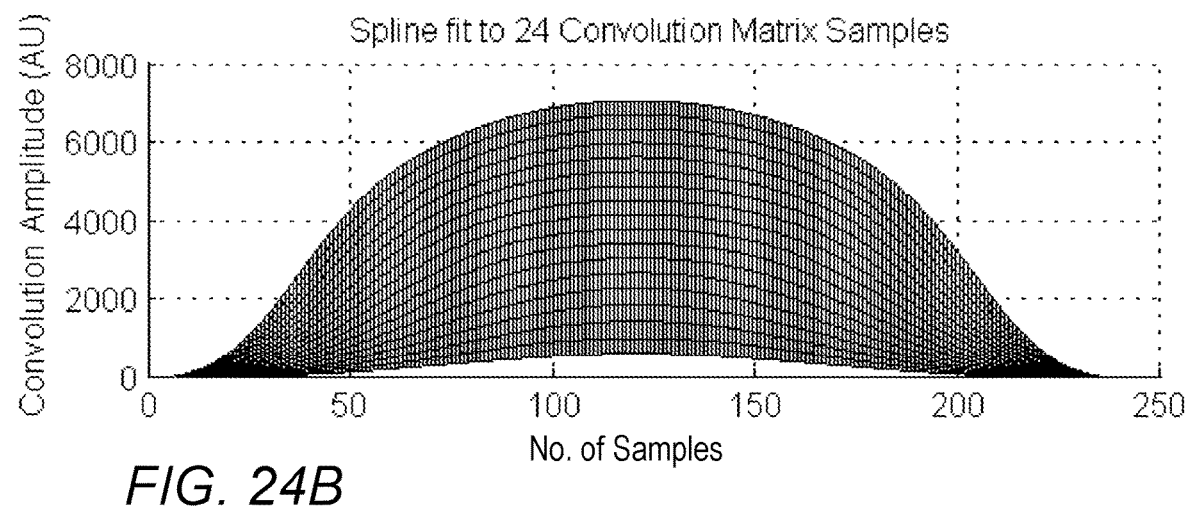
Figure 25A:
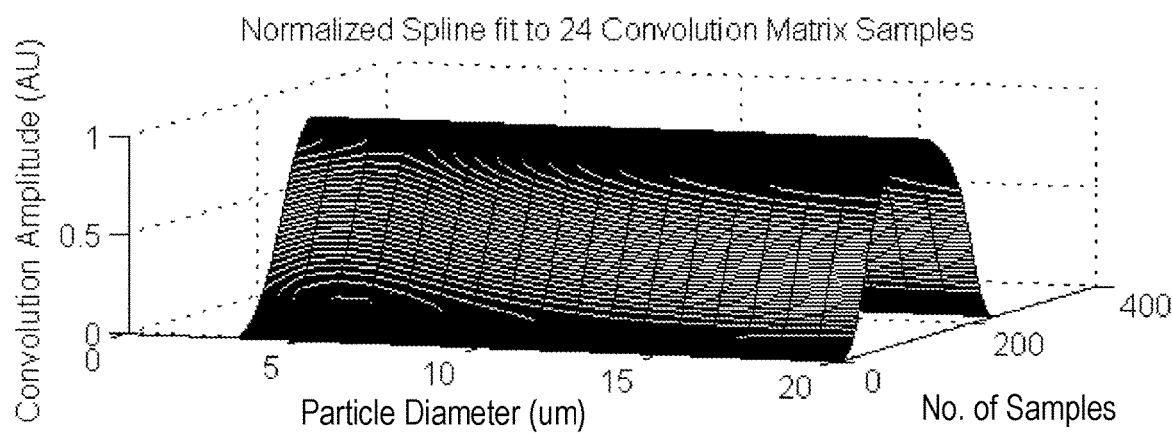
Figure 25B:
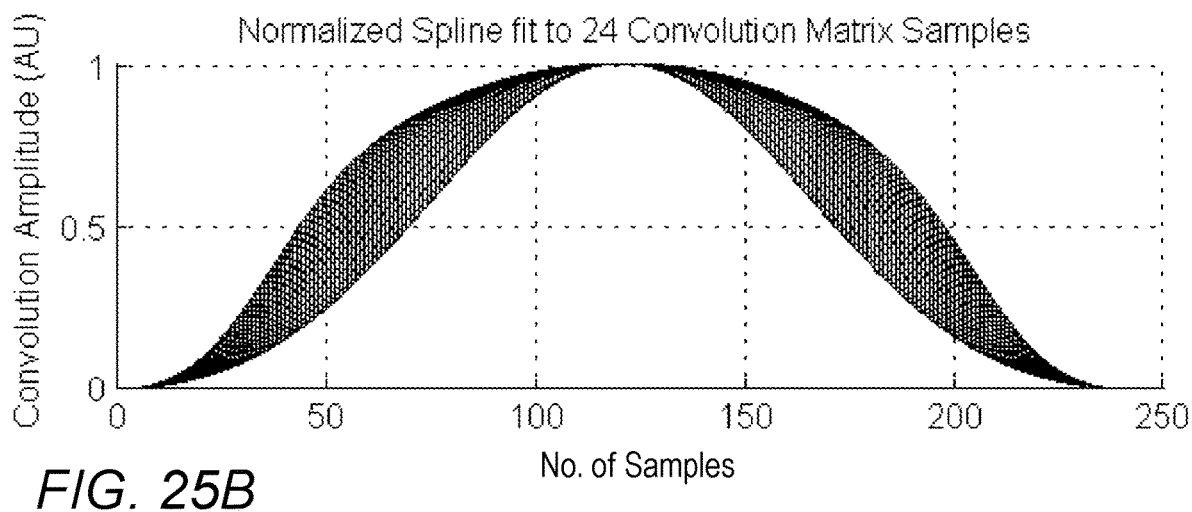
Figure 26:
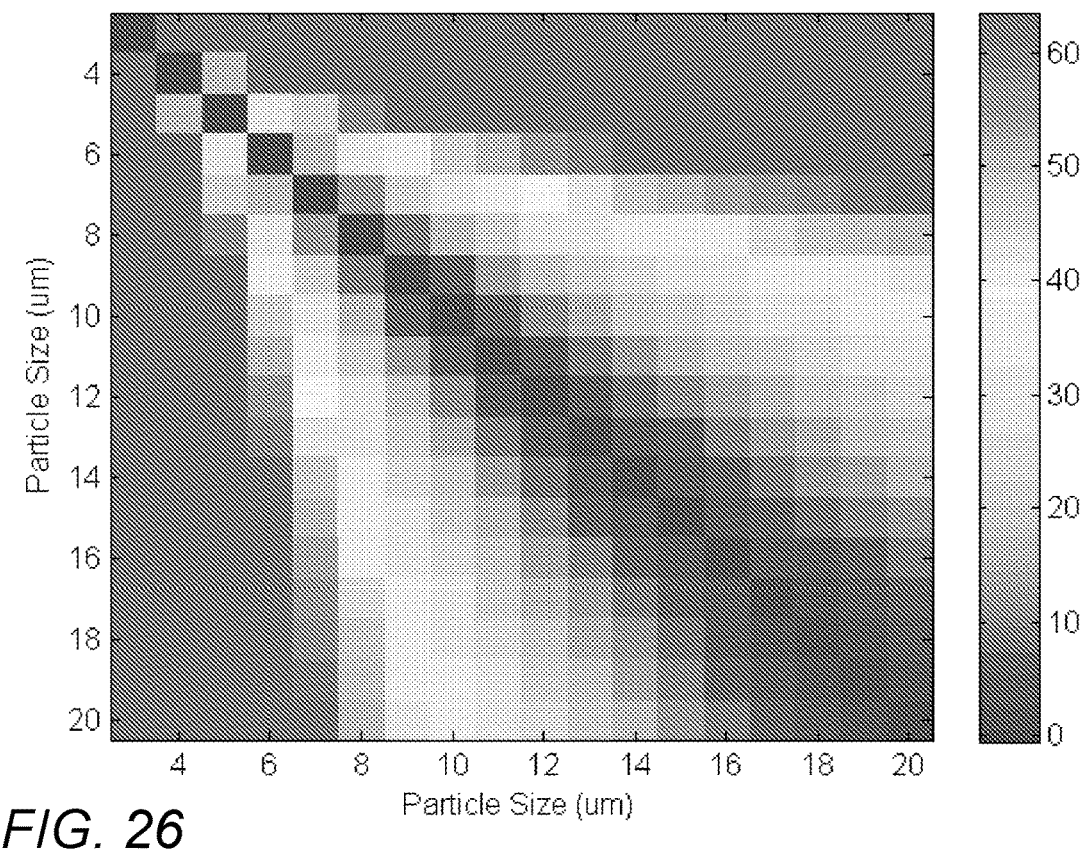
Figure 27:
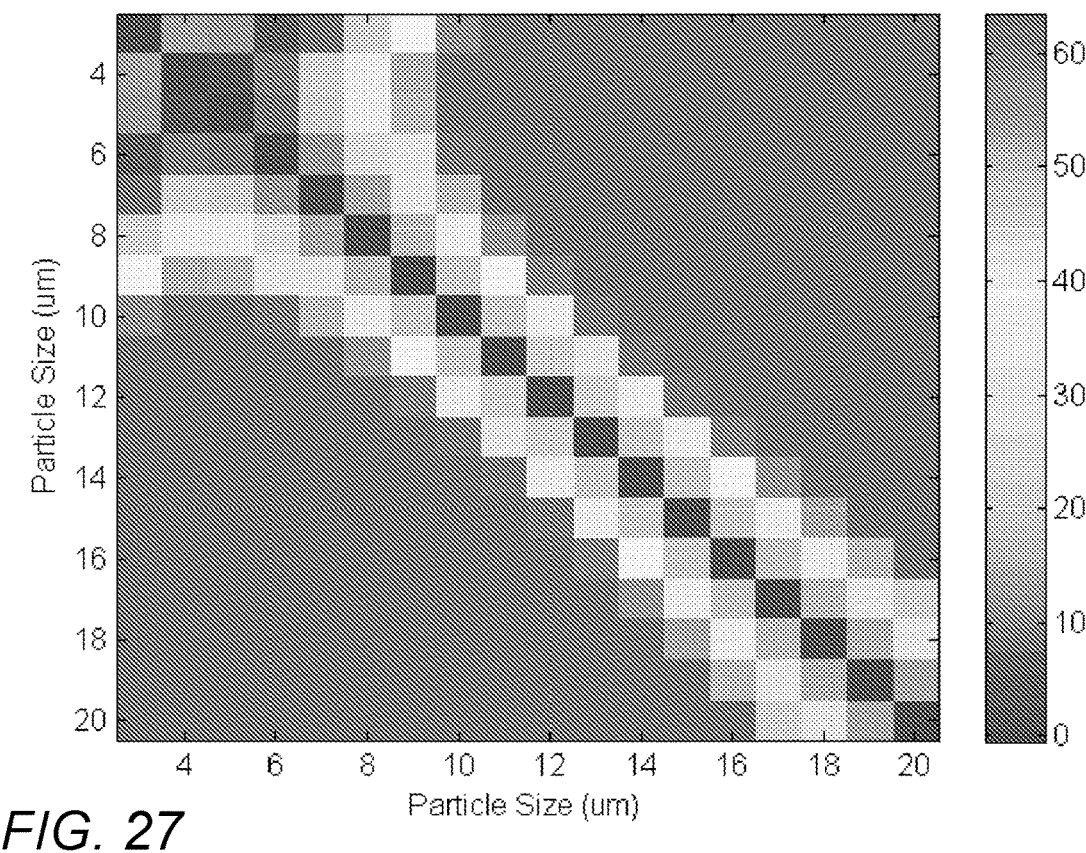
Figure 28:
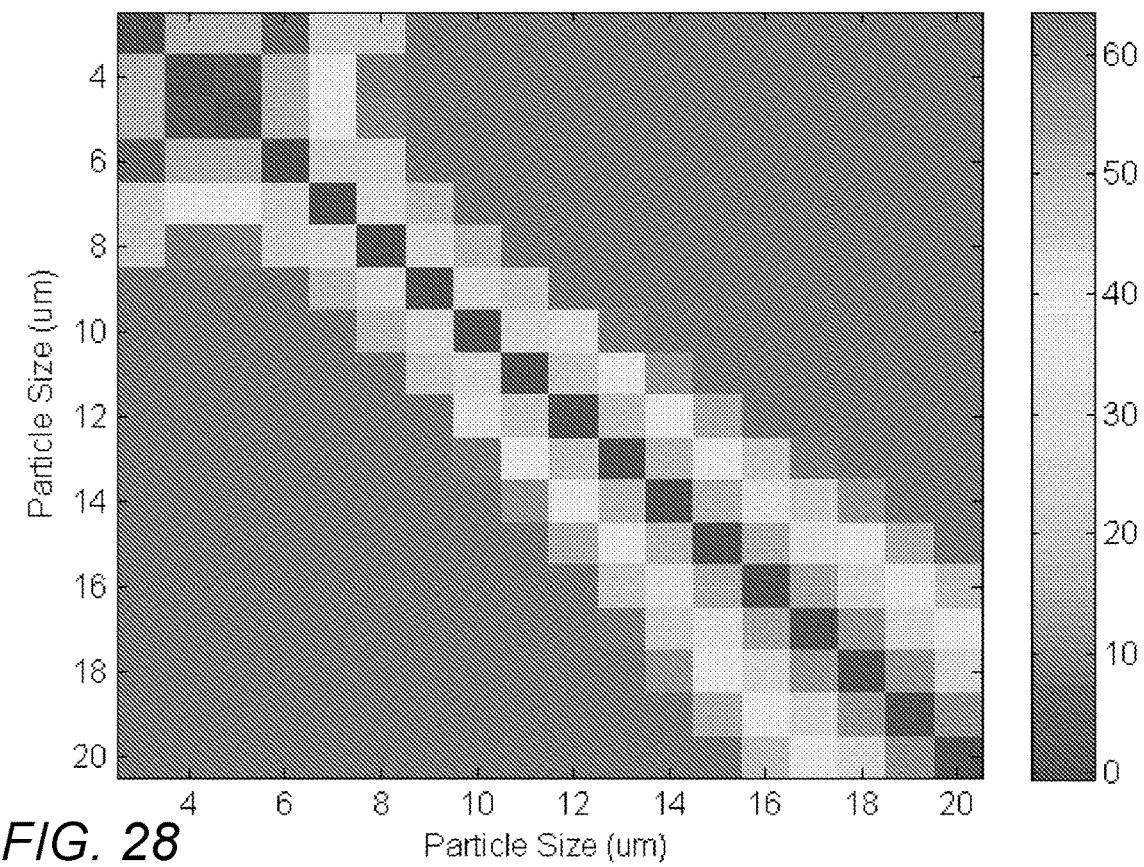
Figure 29:
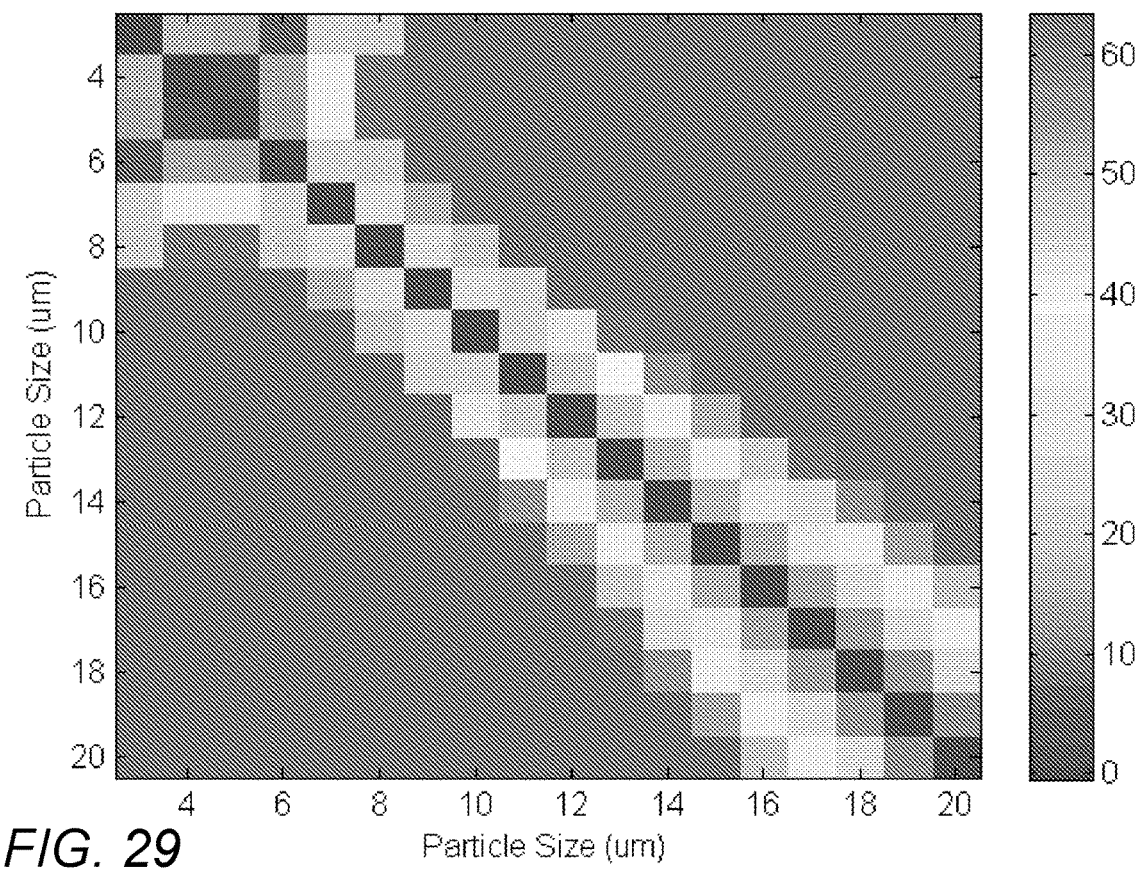
Figure 30:
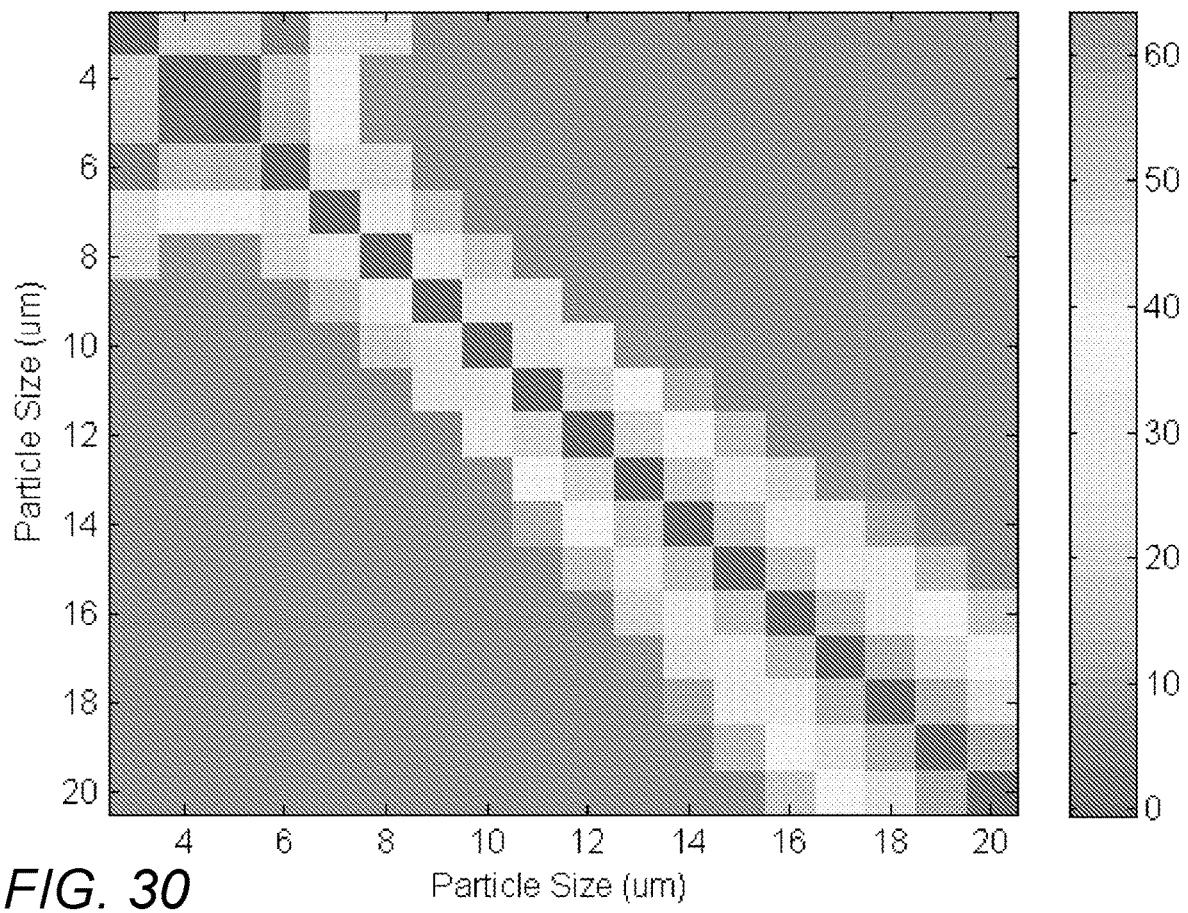
Figure 31A:
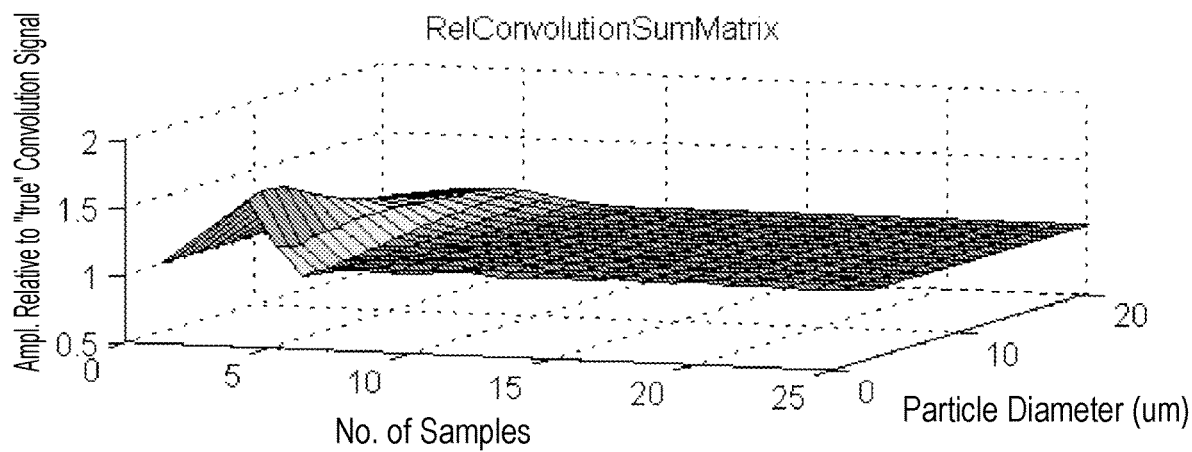

FIG. 16A is a plot of a normalized spline fit to 6 samples from reference convolution matrices for fixed excitation and varying particle diameters showing variation of amplitude and extent as a function of particle size in accordance with an embodiment of the present invention;

FIG. 16B is a plot of a normalized spline fit to 6 samples from reference convolution matrices for fixed excitation and varying particle diameters showing variation of amplitude and extent as a function of particle size viewed from the No. of Samples axis in accordance with an embodiment of the present invention;

FIG. 17A is a plot of 12 samples from reference convolution matrices for fixed excitation and varying particle diameters showing the variation of amplitude and extent as a function of particle size, in accordance with an embodiment of the present invention;

FIG. 17B is a plot of 12 Samples from reference convolution matrices for fixed excitation and varying particle diameters showing the variation of amplitude and extent as a function of particle size viewed from the No. of Samples axis, in accordance with an embodiment of the present invention;

FIG. 18A is a plot of a spline fit to 12 samples from reference convolution matrices for fixed excitation and varying particle diameters showing the variation of amplitude and extent as a function of particle size, in accordance with an embodiment of the present invention;

FIG. 18B is plot of a spline fit to 12 samples from reference convolution matrices for fixed excitation and varying particle diameters showing the variation of amplitude and extent as a function of particle size viewed from the No. of Samples axis, in accordance with an embodiment of the present invention;

FIG. 19A is a plot of a normalized spline fit to 12 samples of reference convolution matrices for fixed excitation and varying particle diameters showing variation of amplitude and extent as a function of particle size, in accordance with an embodiment of the present invention;

FIG. 19B is a normalized spline fit to 12 Samples of reference convolution matrices for fixed excitation and varying particle diameters showing variation of amplitude and extent as a function of particle size viewed from the No. of Samples axis, in accordance with an embodiment of the present invention;

FIG. 20A is a plot of 18 samples from reference convolution matrices for fixed excitation and varying particle diameters showing the variation of amplitude and extent as a function of particle size, in accordance with an embodiment of the present invention;

FIG. 20B is a plot of 18 samples from reference convolution matrices for fixed excitation and varying particle diameters showing the variation of amplitude and extent as a function of particle size viewed from the No. of Samples axis, in accordance with an embodiment of the present invention;

FIG. 21A is a plot of a spline fit to 18 Samples from reference convolution matrices for fixed excitation and varying particle diameters showing the variation of amplitude and extent as a function of particle size, in accordance with an embodiment of the present invention;

FIG. 21B is a plot of a spline fit to 18 Samples from reference convolution matrices for fixed excitation and varying particle diameters showing the variation of amplitude and extent as a function of particle size viewed from the No. of Samples axis, in accordance with an embodiment of the present invention;

FIG. 22A is a plot of a normalized spline fit to 18 samples of reference convolution matrices for fixed excitation and varying particle diameters showing variation of amplitude and extent as a function of particle size, in accordance with an embodiment of the present invention;

FIG. 22B is a plot of a normalized spline fit to 18 samples of reference convolution matrices for fixed excitation and varying particle diameters showing variation of amplitude and extent as a function of particle size viewed from the No. of Samples axis, in accordance with an embodiment of the present invention;

FIG. 23A is a plot of 24 samples from reference convolution matrices for fixed excitation and varying particle diameters showing the variation of amplitude and extent as a function of particle size, in accordance with an embodiment of the present invention;

FIG. 23B is a plot of 24 Samples from reference convolution matrices for fixed excitation and varying particle diameters showing the variation of amplitude and extent as a function of particle size viewed from the No. of Samples axis, in accordance with an embodiment of the present invention;

FIG. 24A is a plot of a spline fit to 24 samples from reference convolution matrices for fixed excitation and varying particle diameters showing the variation of amplitude and extent as a function of particle size, in accordance with an embodiment of the present invention;

FIG. 24B is a plot of a spline fit to 24 samples from reference convolution matrices for fixed excitation and varying particle diameters showing the variation of amplitude and extent as a function of particle size viewed from the No. of Samples axis, in accordance with an embodiment of the present invention;

FIG. 25A is a plot of a normalized spline fit to 24 samples of reference convolution matrices for fixed excitation and varying particle diameters showing variation of amplitude and extent as a function of particle size, in accordance with an embodiment of the present invention;

FIG. 25B is a plot of a normalized spline fit to 24 samples of reference convolution matrices for fixed excitation and varying particle diameters showing variation of amplitude and extent as a function of particle size viewed from the No. of Samples axis, in accordance with an embodiment of the present invention;

FIG. 26 is a heat map of distances between 3 sample normalized spline fits for 3 to 20 micron particles, in accordance with an embodiment of the present invention;

FIG. 27 is a heat map of distances between 6 sample normalized spline fits for 3 to 20 micron particles, in accordance with an embodiment of the present invention;

FIG. 28 is a heat map of distances between 12 sample normalized spline fits for 3 to 20 micron particles, in accordance with an embodiment of the present invention;

FIG. 29 is a heat map of distances between 18 sample normalized spline fits for 3 to 20 micron particles, in accordance with an embodiment of the present invention;

FIG. 30 is a heat map of distances between 24 sample normalized spline fits for 3 to 20 micron particles, in accordance with an embodiment of the present invention;

FIG. 31A is a plot of the ratio of the integral of a reconstructed convolution signal to that of the integral of the "true" convolution signal for given particle diameter as a function of the number of convolution samples showing that beyond about 7 to 8 samples the "reconstructed integral" is essentially equal to the "true integral," in accordance with an embodiment of the present invention; The complete results are in Table 6 below.

Figure 31B:
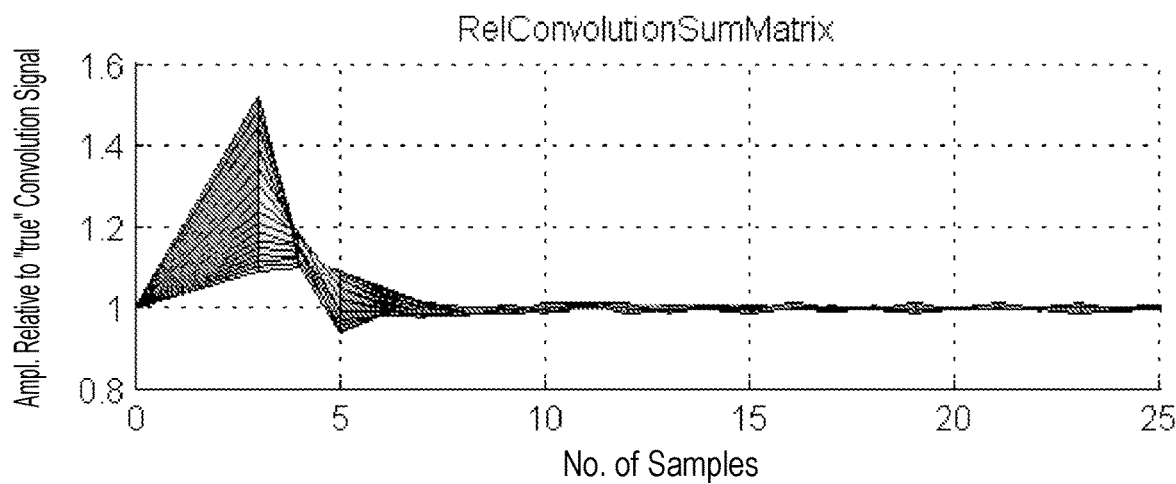

FIG. 31B is a plot of the ratio of the integral of a reconstructed convolution signal to that of the integral of the "true" convolution signal for given particle diameter as a function of the number of convolution samples showing that beyond about 7 to 8 samples the "reconstructed integral" is essentially equal to the "true integral" viewed from the No. of Samples axis, in accordance with an embodiment of the present invention; The complete results are in Table 6 below.

Figure 32A:
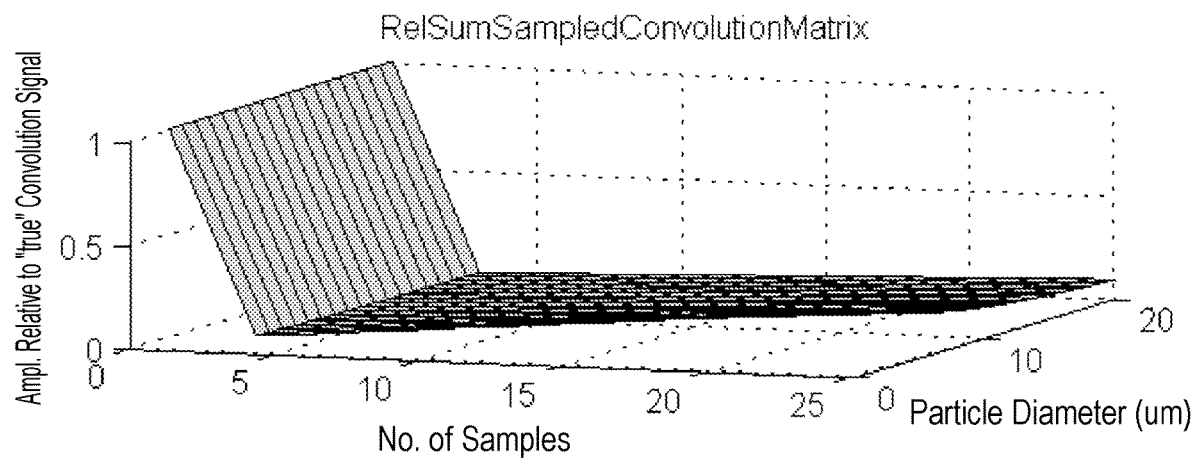

FIG. 32A is a plot of the ratio of the sum of the convolution samples to that of the integral of the "true" convolution signal for given particle diameter as a function of the number of convolution samples showing how the relationship between the sum and the "true convolution integral" varies as a function of particle size, in accordance with an embodiment of the present invention; The complete results are in Table 9 below.

Figure 32B:
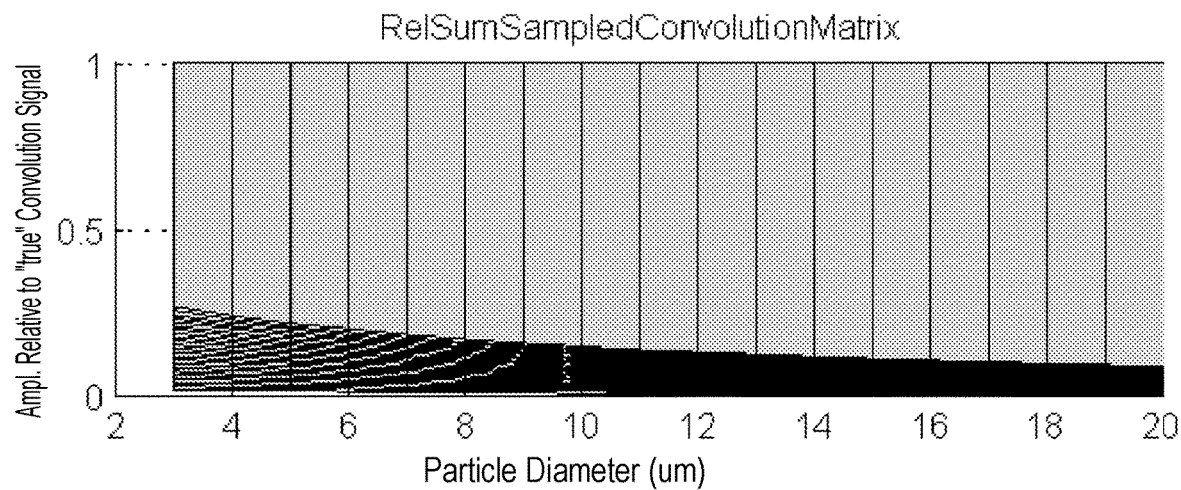

FIG. 32B is a plot of the ratio of the sum of the convolution samples to that of the integral of the "true" convolution signal for given particle diameter as a function of the number of convolution samples showing how the relationship between the sum and the "true convolution integral" varies as a function of particle size viewed from the Particle Diameter axis, in accordance with an embodiment of the present invention; The complete results are in Table 9 below.

Figure 33A:
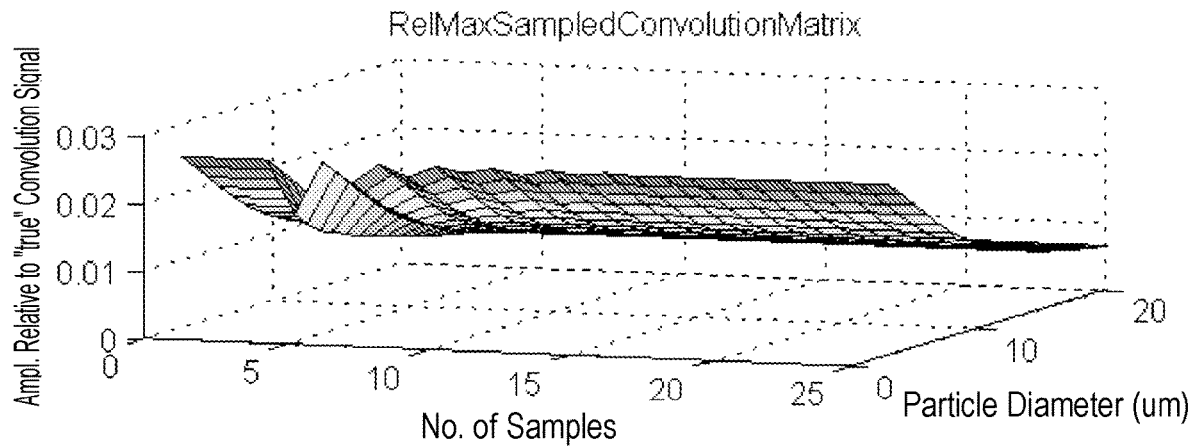

FIG. 33A is a plot of the ratio of the maximum of the convolution samples to that of the integral of the "true" convolution signal for given particle diameter as a function of the number of convolution samples showing how the relationship between the maximum and the "true convolution integral" varies as a function of particle size, in accordance with an embodiment of the present invention; The complete results are in Table 7 below.

Figure 33B:
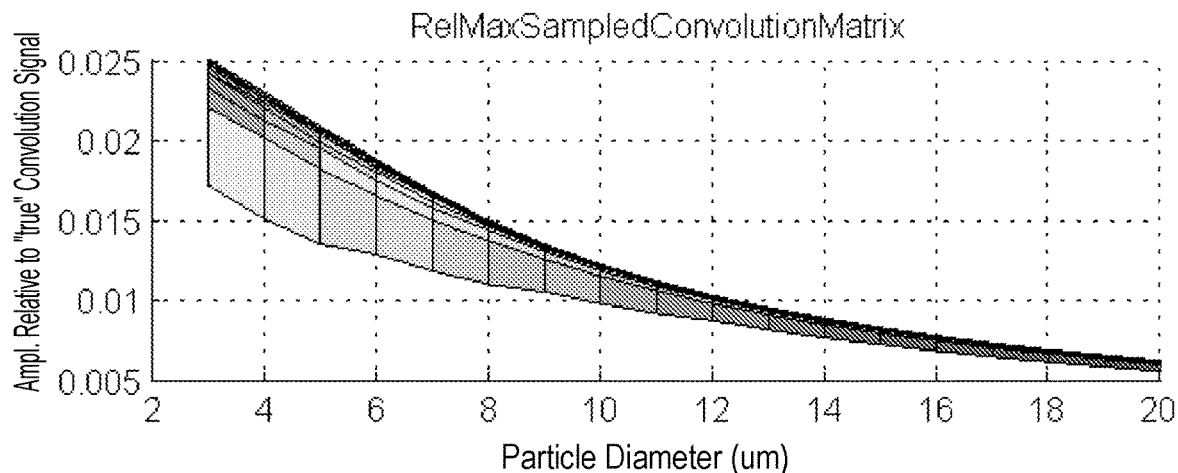

FIG. 33B is a plot of the ratio of the maximum of the convolution samples to that of the integral of the "true" convolution signal for given particle diameter as a function of the number of convolution samples showing how the relationship between the maximum and the "true convolution integral" varies as a function of particle size viewed from the Particle Diameter axis, in accordance with an embodiment of the present invention; The complete results are in Table 7 below.

Figure 34A:
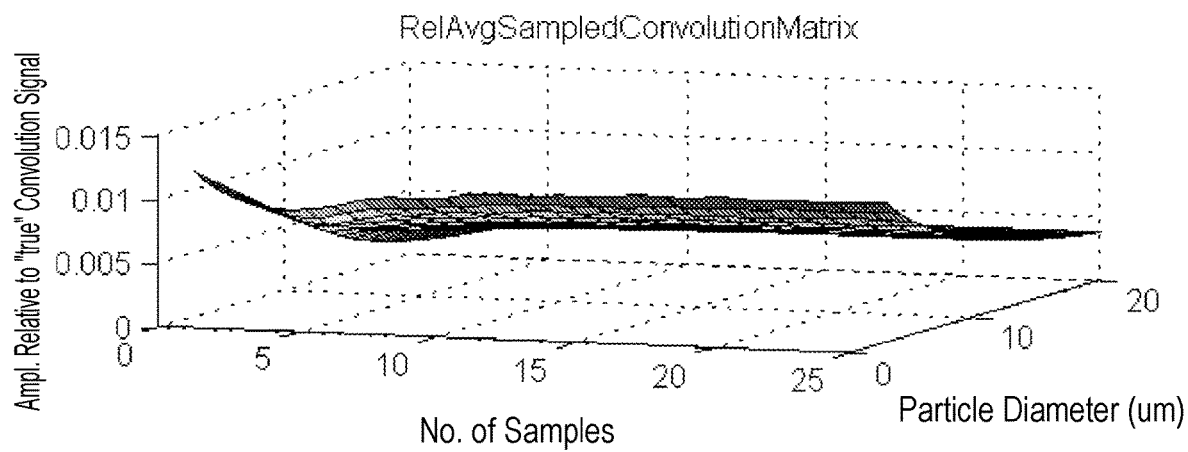

FIG. 34A is the ratio of the average of the convolution samples to that of the integral of the "true" convolution signal for given particle diameter as a function of the number of convolution samples showing how the relationship between the average and the "true convolution integral" varies as a function of particle size, in accordance with an embodiment of the present invention; The complete results are in Table 8 below.

Figure 34B:
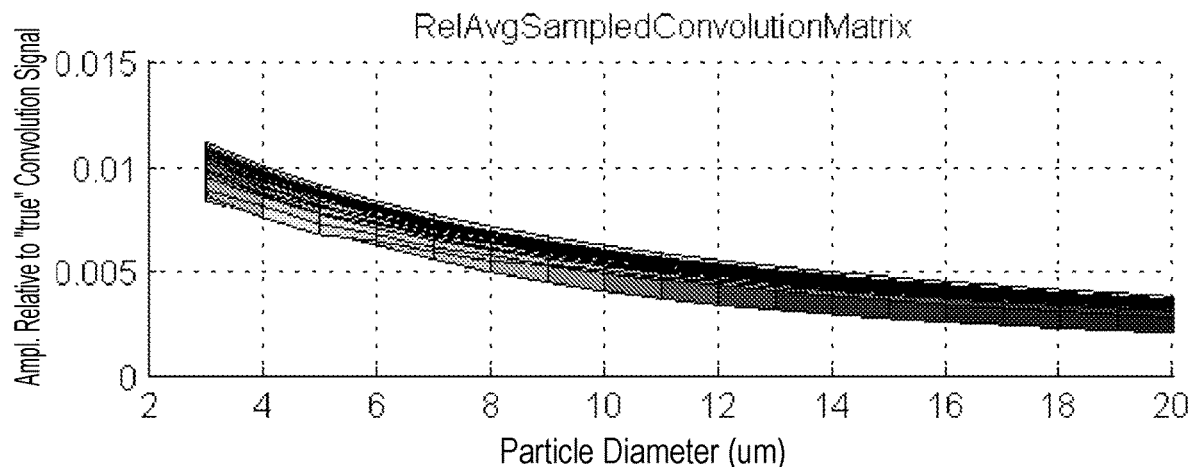

FIG. 34B is the ratio of the average of the convolution samples to that of the integral of the "true" convolution signal for given particle diameter as a function of the number of convolution samples showing how the relationship between the average and the "true convolution integral" varies as a function of particle size viewed from the Particle Diameter axis, in accordance with an embodiment of the present invention; The complete results are in Table 8 below.

In all the figures similar reference numerals identify similar parts.

DETAILED DESCRIPTION OF EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Emission from a fluorophore on a particle flowing through an excitation signal can be modeled as the geometrical convolution of the excitation function with the particle fluorescent emission function. What we wish to know is what the total or integrated emission is from the particle. The following exposition develops a method to determine the integrated particle emission.

Figure 1:
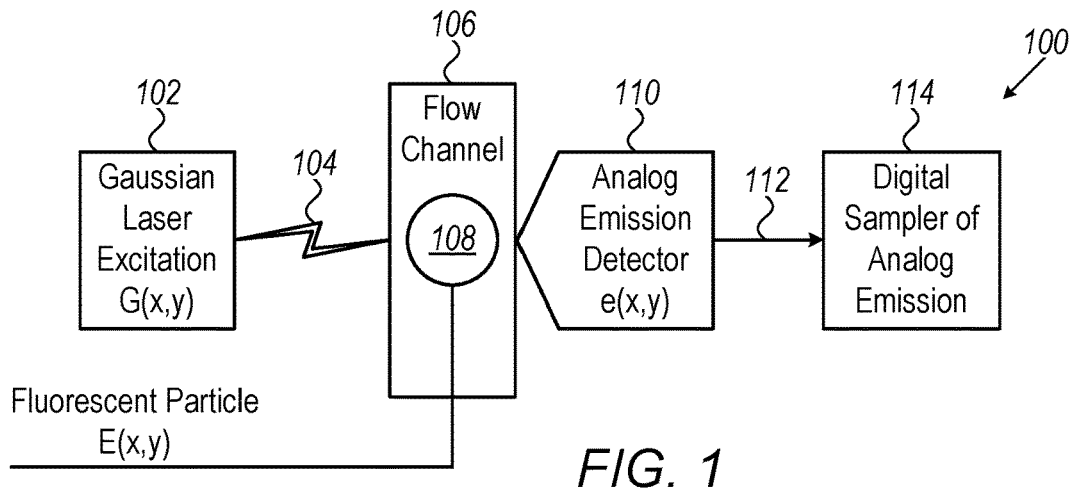

Reference is now made to FIG. 1, which is a simplified schematic illustration of the physical elements of a convolution model, in accordance with an embodiment of the present invention;

A flow chart 100 of the physical model producing the convolved signal representing the particle emission is shown in FIG. 1.

Equation 1 through Equation 5 below describe the signals at various points in the block diagram mathematically.

Briefly, the emission e(x,y) captured by an Analog Emission Detector 110 is the result of the convolution of a Gaussian Laser Excitation, G(x,y) 102, which emits excitation energy 104, such as laser energy, with a Fluorescent Particle fluorescent emission E(x,y) 108 in a flow channel 106. This convolved signal, which is a geometrical convolution, is sampled asynchronously to the motion of the particle that creates the convolution. A Digital Sampler 114 samples the Analog Emission Detector 110 output 112 at a fixed rate. Thus, the number of samples for a given convolution event depends both on the size of the particle and its velocity since these 2 parameters determine the time duration of the of the Analog Emission Detector output 112 corresponding to a specific event.

How should these time samples be used to reconstruct or estimate $\int e(x)dx$?

Several methods are possible and have been used. Among these are:
1. use the maximum sample value or the maximum of the curve fitted to the sample values
2. sum the sample values
3. normalize the sum by the number of sample values, effectively the average of the sample values.

Each of these suggested methods will fail in systems in which particle velocity varies, particle size varies, and/or not all of the particles are small enough to fall within the excitation window.

If the geometrical size of the convolution were known, the best fit of the sample values to a function of this size would yield an estimate of the convolution function independent of particle size and number of samples. Thus, if we first use the sample values to determine the size of the convolution, and then use the sample values to determine a best fit function to the presumed size of the convolution we will have achieved a sample and particle size independent method. The code and various output graphs and tables that follow demonstrate how this can be done.

An alternative would be to use the relationship between each of these measures and $\int e(x)dx$ as for example computed in Table 7, Table 8, and Table 9 by number of samples and particle size once the particle size is determined to provide an estimate of $\int e(x)dx$ by dividing the particle dependent method by its value relative to $\int e(x)dx$ from the table.

The present invention provides methods and systems for deconvolution of a flow cytometer particle output in order to determine individual total particle fluorescent emission, the system including an apparatus adapted to pass a laser excitation energy into a generally perpendicular flow cytometer channel element through which a particle passes, the particle being adapted to be irradiated by the apparatus and to emit at least one fluorescent emission responsive to the laser energy, an analog emission detector adapted to detect at least some of the at least one fluorescent emission, a digital sampler adapted to provide multiple time samples of said analog detector output of said emission from an irradiated particle in said flow cytometer element, adapted to detect the at least one output signal and to blindly deconvolve the at least one output thereby quantifying actual individual particle emission.

Principles

Emission from a fluorophore on a particle flowing through an excitation signal can be modeled as the convolution of the excitation function with the particle fluorescent emission function (See for example Grinvald, Amiram, and Izchak Z. Steinberg. "On the analysis of fluorescence decay kinetics by the method of least-squares." *Analytical biochemistry*

59.2 (1974): 583-598.). What we wish to know is what the total or integrated emission is from the particle. The following exposition develops a method to determine the integrated particle emission.

Flow Cytometer Model

A flow chart 100 of the physical model producing the convolved signal representing the particle emission is shown in FIG. 1.

Estimating Particle Emission

General Description

Equation 1 through Equation 5 below describe the signals at various points in the block diagram mathematically. Briefly, the emission e(x,y) captured by the Analog Emission Detector 110 is the result of the convolution of the Gaussian Laser Excitation, G(x,y) 102 with the Fluorescent Particle fluorescent emission E(x,y) 108. This convolved signal, which is a geometrical convolution, is sampled asynchronously to the motion of the particle that creates the convolution. The Digital Sampler samples the Analog Emission Detector output 112 at a fixed rate. Thus, the number of samples for a given convolution event depends both on the size of the particle and its velocity since these 2 parameters determine the time duration of the of the Analog Emission Detector output corresponding to a specific event.

DETAILED DESCRIPTION

When excited by laser excitation at an appropriate wavelength for the fluorophore on the particle, the overall detected emission, e(x,y), from the particle is given by the convolution of the excitation intensity as a function of x and y, G(x,y) 102, and the particle emission function, E(x,y) 108 as shown in Equation 1.

$$e(x,y) = \iint G(x-\xi, y-\upsilon) E(\xi,\upsilon) d\xi d\upsilon \qquad \text{Equation 1}$$

In the case where the excitation is uniform across the channel direction, y, and Gaussian along the channel, x, the excitation function G (x,y) is described by Equation 2.

$$G(x,y) = \mathcal{N}(x;\mu,\sigma) \forall y \qquad \text{Equation 2}$$

With this excitation the convolution is reduced to a one dimensional convolution of the Gaussian beam shape with the integrated particle emission across the channel as shown in Equation 3, Equation 4 and Equation 5. Thus, our observable is a sampled version of e(x), and we wish to estimate $\int E(x)_y dx$ the integrated emission from the particle.

$$e(x, y) = \int \int \mathcal{N}(x-\xi; \mu, \sigma) E(\xi, \upsilon) d\xi d\upsilon \qquad \text{Equation 3}$$

$$= \int \mathcal{N}(x-\xi; \mu, \sigma) \int E(\xi, \upsilon) d\upsilon d\xi$$

$$e(x, y) = e(x) = \int \mathcal{N}(x-\xi; \mu, \sigma) E(\xi)_y d\xi \text{ where,} \qquad \text{Equation 4}$$

$$E(x)_y = \int E(x, y) dy \qquad \text{Equation 5}$$

From Fubini's theorem, if f and g are integrable functions, then the integral of their convolution on the whole space is simply obtained as the product of their integrals:

$$\int_{R^d} (f*g)(x) dx = (\int_{R^d} f(x) dx)(\int_{R^d} g(x) dx) \qquad \text{Equation 6}$$

Thus, if we integrate Equation 4 with respect to x, the result is a constant times $\int E(x)_y dx$, our desired result, since the excitation is constant.

$$\int e(x) dx = \int \mathcal{N}(x;\mu,\sigma) dx \int E(x)_y dx = K \int E(x)_y dx \qquad \text{Equation 7}$$

Sampling the Convolution Signal

As noted in FIG. 1, the Digital Sampler 114 samples the Analog Emission Detector output 112 at a fixed rate so that the number of samples for a given convolution event depends both on the size of the particle and its velocity. Thus the signal provided for analysis is a time sampled version of e(x), $[e(t_i)]_1^n$, as shown in Equation 8.

$$[e(t_i)]_1^n = \left[ \int_{x(t_i)}^{x(t_{i+1})} e(x) dx \right]_1^n \text{ where} \qquad \text{Equation 8}$$

$$t_{i+1} \geq t_i \text{ and } x(t_{i+1}) \geq x(t_i)$$

In the limit as $x(t_{i+1}) \rightarrow x(t_i)$ we have the idealized impulse sampler. In general, we have a pulse sampler with pulse width $x(t_{i+1}) - x(t_i)$. $e(t_i)$ for this case is the average of e(x) in the interval multiplied by the length of the interval. For the case where all the sampling intervals are equal using the $e(t_i)$ without normalizing by the interval width simply adds another multiplicative constant to the values. For our purposes we can ignore this normalization since we are interested in relative values only, and there are other arbitrary multiplicative constants in the data stream.

How should these time samples be used to reconstruct or estimate $\int e(x) dx$?

Several methods are possible and have been used. Among these are:

1. use the maximum sample value or the maximum of the curve fitted to the sample values
2. sum the sample values
3. normalize the sum by the number of sample values, effectively the average of the sample values.

Each of these suggested methods will fail in systems in which particle velocity varies, particle size varies, and/or not all of the particles are small enough to fall within the excitation window.

Particles Smaller and Larger than Excitation

If the particle is smaller than the excitation, then choosing a maximum sample value or the maximum of a curve fitted to the sample values will be a reasonable estimate of the integrated emission from the particle. In this case, the maximum value is in fact a good estimate of the total particle emission. However, if the particle is larger than the excitation window there is no single sample that includes the entire emission from the particle and therefore the maximum of the sample values will represent only a fraction of the integrated emission from the particle. This fraction will vary depending on the relative size of the particle compared to the excitation window. Thus, this method does not work universally.

Sum or Normalized Sum of the Sample Values

The sum method fails in the case when the velocity of the particles is not constant. When the velocity of the particle is not constant, the number of samples, n, will vary. Each sample is a valid sample of the convolution but depending on the exact velocity will be at a different location along the convolution and thus will provide a different amplitude of the underlying convolution. Thus, simply summing the sample values does not provide an appropriate estimate of $\int e(x) dx$. This can easily be seen by considering a case of n samples and 2n samples where each of the additional n samples is between a pair of the original samples. Summing the 2n samples will yield a sum approximately twice that of the sum of the n samples. A further demonstration based on actual data samples is shown in Table 5.

One might think that normalizing this sum by the number of samples is a reasonable solution. As long as the particle size remains constant this normalized sum, which is the average of the convolution will provide a consistent estimate of the convolution sum as the emission amplitude of the particle varies. This is clear since the same intensity multiplicative factor is applied to both the average of the convolution and its sum.

However since the average of the convolution and the sum of the convolution do not bear the same relationship for different size particles this method fails when comparing different sized particles.

Particle Size Independent Method

If the geometrical size of the convolution were known, the best fit of the sample values to a function of this size would yield an estimate of the convolution function independent of particle size and number of samples. Thus, if we first use the sample values or any other method (e.g. analysis of forward and/or side scatter, and/or imaging to determine the particle size) to determine the size of the convolution, and then use the sample values to determine a best fit function to the presumed size of the convolution we will have achieved a sample and particle size independent method. The code and various output graphs and tables that follow demonstrate how this can be done.

An alternative would be to use the relationship between each of these measures and $\int e(x)dx$ as for example computed in Table 7, Table 8, and Table 9 by number of samples and particle size once the particle size is determined to provide an estimate of $\int e(x)dx$ by dividing the particle dependent method by its value relative to $\int e(x)dx$ from the table.

Method

General Description

Figure 2:
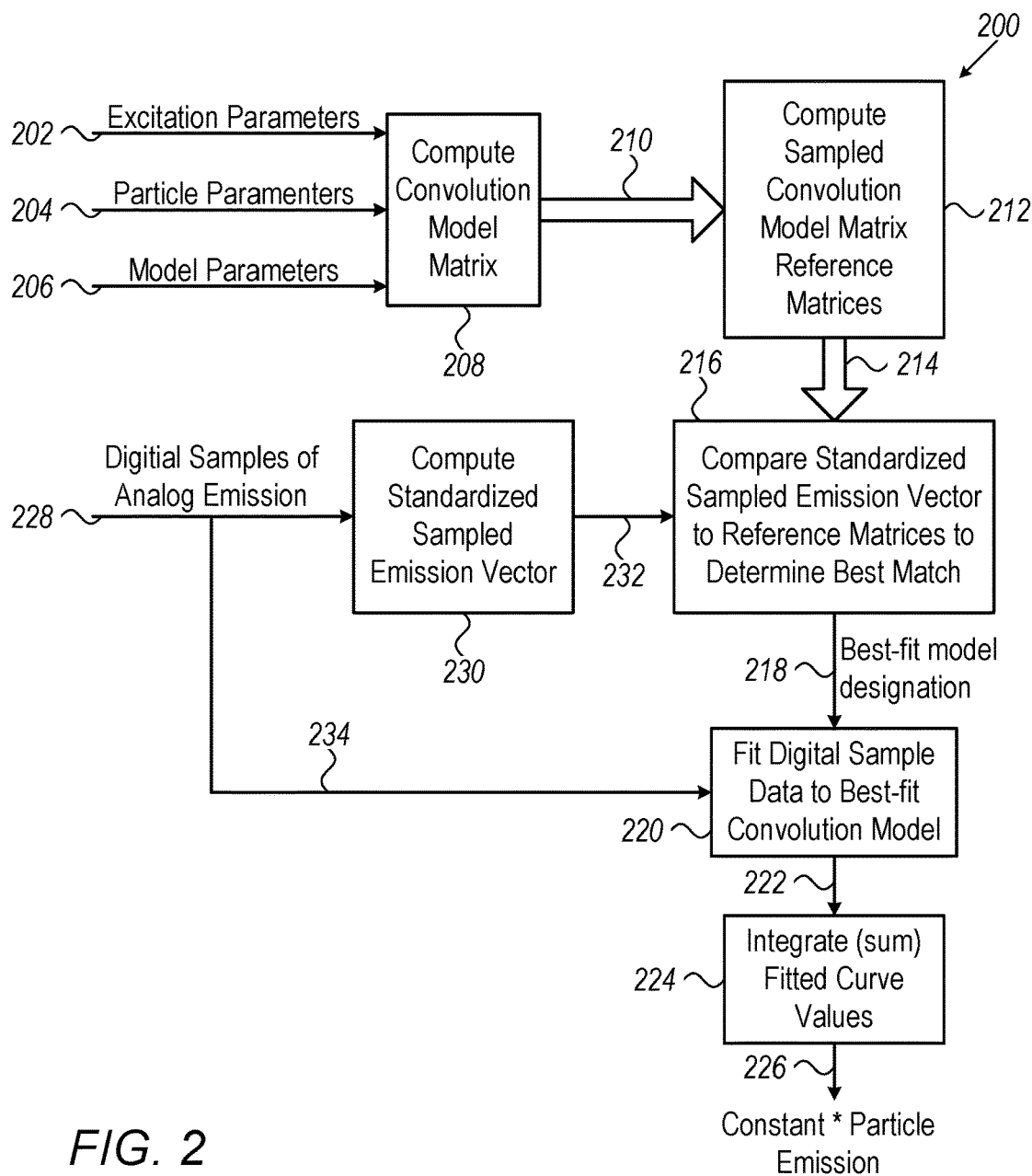

Shown in FIG. 2 is a block diagram of the method used to deconvolve the digital samples of the analog emission signal in order to obtain the value of the particle emission.

The primary issue solved by this method is the relationship between the digital samples and the true total particle emission. As will be shown below, methods that have been used such as summing the digital signals, averaging the digital signals or using the peak of the digital signals or a curve fitted through them bear a relationship to the total particle emission that depends on the size of the particle. In addition, any method that simply sums values of the digital signals will trivially give incorrect answers as the number of samples for a given particle varies. Indeed, the number of samples for the same size particle will vary depending on its velocity since the sampling occurs at a fixed rate regardless of the particle velocity.

The basic method is to use a model of convolved signals for different particles and excitation patterns and determine which pattern is best matched by the digital samples. Given the best matched pattern, the digital signals are fit to this pattern. After this fit, the estimate of the true convolution is integrated. By Fubini's theorem, see Equation 6 and Equation 7 above, this provides the product of the integral of the excitation and the integral of the emission.

Since we know the model, the integral of the excitation is known and therefore the integral of the particle emission, or total particle emission can be determined by dividing the product by the integral of the excitation. In the case where the excitation is constant the integral of the convolution can be used without modification since it is simply the total particle emission multiplied by a constant as shown in Equation 7 above. The rest of this exposition will assume that the excitation is constant. The extension to excitation variation simply increases the number of cases of model convolutions. One skilled in the art could easily extend the work here to cover those additional cases.

Detailed Description of the Method Based on FIG. 2

Reference is now made to FIG. 2, which is a simplified schematic illustration of a flowchart 200 of a method for deconvolving the total particle emission from the signals obtained from the physical elements of a convolution model, in accordance with an embodiment of the present invention.

Starting at the upper left block in FIG. 2, references must first be computed in a computing step 212. It should be noted that these references need be computed only once if the method in flowchart 200 is to be applied to multiple samples.

The Matlab code beginning in the section, Read parameter value' below shows an implementation of this method. 10 parameters describing an excitation 202, a particle 204 and a model 206 are read from an Excel spreadsheet. The following are the comments from the routine 'ReadDeconParamValues' that describe the 10 parameters. Parameters 1 and 2 describe the excitation. Parameters 4, 5 and 6 describe the particles. The remaining parameters describe the model.

A single routine, 'BuildReferenceMatrices' computes a convolution model matrix 208 as well as the various sampled versions of the data in this matrix. The Matlab code is shown in the section Compute reference matrices' below. An output from the matrix is exemplified by output 210.

Using the physical elements, depicted in FIG. 1, information, signals and/or data from fluorescent particle 108 are obtained and from output 210 are inputted into a first computing step 212 to compute sampled convolution model reference matrices and to output a reference matrix output 214.

In parallel, digital samples of analog emission 228 are sampled and inputted into a second computing step 230 for computing standardized sample emission vectors.

In a third computing step 216, data 214 from the reference matrix output step 212 is sampled and reference matrices are computed. At least one output of sampled emission vectors 232 are outputted from second computing step 230. Additionally, at least one output 232 from the second computing step, comprising standardized sampled emission vectors 232 are compared with reference matrices data 214 in a comparing step 216 to determine a best match and output of a best-fit model designation 218 is outputted.

In a fitting step 220, samples of analog emission 234 are fitted to the best fit model designation 218, to output a best-fit convolution model output 222. The best-fit convolution model output 222 is then integrated in an integrating step 224 thereby producing a deconvolution 226 of total particle emission.

Reference is now made to FIG. 10A, which is a reference convolution matrices plot for fixed excitation and varying particle diameters displayed as side-by-side surface plots showing the variation of amplitude and extent as a function of particle size in accordance with an embodiment of the present invention. Additionally, FIG. 10B shows a reference convolution matrices plot for fixed excitation and varying particle diameters displayed as side-by-side surface plots showing the variation of amplitude and extent as a function of particle size viewed along the Particle Diameter axis in accordance with an embodiment of the present invention.

The convolution signal as a function of particle size for a fixed Gaussian excitation with a waist of 3 μm along the direction of flow is shown as a surface plot in FIG. 10A and FIG. 10B. One can see that as the particle size increases both the amplitude of the convolved signal and its extent increase. The number of samples of a given overall convolved signal resulting from the passage of a particle of a given size is determined by the velocity of the particle.

As will be seen below once the number of samples exceeds a minimum number to reproduce the convolved signal one can use these samples to estimate the convolved signal by fitting a spline of a length equal to that of the sum of the lengths of the particle and the excitation in the convolution signal model matrix, or 2*the particle length+ the length of the excitation depending on the convolution model. The Matlab 'conv' function that provides a convolution length of m+n−1 for vectors of length m and n respectively was used for the computations in this discussion without loss of generality.

Thus, in order to properly utilize the sampled values one must obtain an estimate of the particle size from the sample values. This is accomplished by standardizing the sampled values in order to compare them with standardized representations of samples of the model.

Specifically, for a given particle size the resulting convolution in the convolution model matrix is sampled from 3 to 25 times at equally spaced intervals. Examples of these samplings as a function of particle size are shown in the surface plots in FIG. 11A, FIG. 11B, FIG. 14A, FIG. 14B, FIG. 17A, FIG. 17B, FIG. 20A, FIG. 20B, FIG. 23A, and FIG. 23B for 3, 6, 12, 18, and 24 samples, respectively.

FIG. 11A is a plot 1100 of 3 samples from reference convolution matrices for fixed excitation and varying particle diameters showing the variation of amplitude and extent as a function of particle size in accordance with an embodiment of the present invention. FIG. 11B shows a plot of 3 Samples from reference convolution matrices for fixed excitation and varying particle diameters showing the variation of amplitude and extent as a function of particle size viewed from the No. of Samples axis in accordance with an embodiment of the present invention;

FIG. 14A shows a plot of 6 samples from reference convolution matrices for fixed excitation and varying particle diameters showing the variation of amplitude and extent as a function of particle size in accordance with an embodiment of the present invention. FIG. 14B shows a plot of 6 samples from reference convolution matrices for fixed excitation and varying particle diameters showing the variation of amplitude and extent as a function of particle size viewed from the No. of Samples axis in accordance with an embodiment of the present invention; FIG. 17A shows a plot of 12 samples from reference convolution matrices for fixed excitation and varying particle diameters showing the variation of amplitude and extent as a function of particle size, in accordance with an embodiment of the present invention. FIG. 17B shows a plot of 12 Samples from reference convolution matrices for fixed excitation and varying particle diameters showing the variation of amplitude and extent as a function of particle size viewed from the No. of Samples axis, in accordance with an embodiment of the present invention;

FIG. 20A shows a plot of 18 samples from reference convolution matrices for fixed excitation and varying particle diameters showing the variation of amplitude and extent as a function of particle size, in accordance with an embodiment of the present invention. FIG. 20B shows a plot of 18 samples from reference convolution matrices for fixed excitation and varying particle diameters showing the variation of amplitude and extent as a function of particle size viewed from the No. of Samples axis in accordance with an embodiment of the present invention.

FIG. 23A shows a plot of 24 samples from reference convolution matrices for fixed excitation and varying particle diameters showing the variation of amplitude and extent as a function of particle size, in accordance with an embodiment of the present invention. FIG. 23B shows a plot of 24 Samples from reference convolution matrices for fixed excitation and varying particle diameters showing the variation of amplitude and extent as a function of particle size viewed from the No. of Samples axis, in accordance with an embodiment of the present invention.

In order to standardize these sampled versions, a spline with 10 points per sample point is fit to the samples. Thus for example, cases with 3 sample points will be represented by spline fits of 30 points. Examples of these spline fits are shown in the surface plots in FIG. 12A, FIG. 12B, FIG. 15A, FIG. 15B, FIG. 18A, FIG. 18B, FIG. 21A, FIG. 21B, FIG. 24A, and FIG. 24B for 3, 6, 12, 18, and 24 samples, respectively.

FIG. 12A is a plot of a spline fit to 3 samples from reference convolution matrices for fixed excitation and varying particle diameters showing the variation of amplitude and extent as a function of particle size in accordance with an embodiment of the present invention;

FIG. 12B is a plot of a spline fit to 3 Samples from Reference Convolution Matrices for fixed excitation and varying particle diameters showing the variation of amplitude and extent as a function of particle size viewed from the No. of Samples axis in accordance with an embodiment of the present invention; FIG. 15A shows a plot of a spline fit to 6 samples from reference convolution matrices for fixed excitation and varying particle diameters showing the variation of amplitude and extent as a function of particle size in accordance with an embodiment of the present invention. FIG. 15B shows a plot of a spline fit to 6 samples from reference convolution matrices for fixed excitation and varying particle diameters showing the variation of amplitude and extent as a function of particle size viewed from the No. of Samples axis.

FIG. 18A shows a plot of a spline fit to 12 samples from reference convolution matrices for fixed excitation and varying particle diameters showing the variation of amplitude and extent as a function of particle size, in accordance with an embodiment of the present invention. FIG. 18B shows a plot of a spline fit to 12 samples from reference convolution matrices for fixed excitation and varying particle diameters showing the variation of amplitude and extent as a function of particle size viewed from the No. of Samples axis, in accordance with an embodiment of the present invention.

FIG. 21A shows a plot of a spline fit to 18 Samples from reference convolution matrices for fixed excitation and varying particle diameters showing the variation of amplitude and extent as a function of particle size, in accordance with an embodiment of the present invention. FIG. 21B shows a plot of a spline fit to 18 Samples from reference convolution matrices for fixed excitation and varying particle diameters showing the variation of amplitude and extent as a function of particle size viewed from the No. of Samples axis, in accordance with an embodiment of the present invention.

FIG. 24A shows a plot of a spline fit to 24 samples from reference convolution matrices for fixed excitation and varying particle diameters showing the variation of amplitude and extent as a function of particle size, in accordance with an embodiment of the present invention. FIG. 24B shows a plot of a spline fit to 24 samples from reference convolution matrices for fixed excitation and varying particle diameters showing the variation of amplitude and extent as a function of particle size viewed from the No. of Samples axis, in accordance with an embodiment of the present invention. One more step is necessary in order to complete the references. It is clear that the amplitude of the samples will vary as the particle emission. On the other hand, the shape of the convolution signal depends only on the size of the excitation, which for our purposes is fixed, and the size of the particle. Thus we wish to have an amplitude independent reference. This is obtained by normalizing each of the spline fit curves to have a maximum amplitude of one. Examples of these normalized spline fits are shown in the surface plots in FIG. 13A, FIG. 13B, FIG. 16A, FIG. 16B, FIG. 19A, FIG. 19B, FIG. 22A, FIG. 22B, FIG. 25A, and FIG. 25B, for 3, 6, 12, 18, and 24 samples, respectively.

FIG. 13A shows a plot of a normalized spline fit to 3 samples from reference convolution matrices for fixed excitation and varying particle diameters showing variation of amplitude and extent as a function of particle size in accordance with an embodiment of the present invention. FIG. 13B shows a plot of a normalized spline fit to 3 samples from reference convolution matrices for fixed excitation and varying particle diameters showing variation of amplitude and extent as a function of particle size viewed from the No. of Samples axis in accordance with an embodiment of the present invention.

FIG. 16A shows a plot of a normalized spline fit to 6 samples from reference convolution matrices for fixed excitation and varying particle diameters showing variation of amplitude and extent as a function of particle size in accordance with an embodiment of the present invention. FIG. 16B shows a plot of a normalized spline fit to 6 samples from reference convolution matrices for fixed excitation and varying particle diameters showing variation of amplitude and extent as a function of particle size viewed from the No. of Samples axis in accordance with an embodiment of the present invention.

FIG. 19A shows a plot of a normalized spline fit to 12 samples of reference convolution matrices for fixed excitation and varying particle diameters showing variation of amplitude and extent as a function of particle size, in accordance with an embodiment of the present invention. FIG. 19B shows a normalized spline fit to 12 Samples of reference convolution matrices for fixed excitation and varying particle diameters showing variation of amplitude and extent as a function of particle size viewed from the No. of Samples axis, in accordance with an embodiment of the present invention.

FIG. 22A shows a plot of a normalized spline fit to 18 samples of reference convolution matrices for fixed excitation and varying particle diameters showing variation of amplitude and extent as a function of particle size, in accordance with an embodiment of the present invention. FIG. 22B shows a plot of a normalized spline fit to 18 samples of reference convolution matrices for fixed excitation and varying particle diameters showing variation of amplitude and extent as a function of particle size viewed from the No. of Samples axis, in accordance with an embodiment of the present invention;

FIG. 25A shows a plot of a normalized spline fit to 24 samples of reference convolution matrices for fixed excitation and varying particle diameters showing variation of amplitude and extent as a function of particle size, in accordance with an embodiment of the present invention. FIG. 25B shows a plot of a normalized spline fit to 24 samples of reference convolution matrices for fixed excitation and varying particle diameters showing variation of amplitude and extent as a function of particle size viewed from the No. of Samples axis, in accordance with an embodiment of the present invention.

One can observe that for 3 samples as shown in FIG. 13A and FIG. 13B, there is no difference in the normalized shape as a function of particle size. However, even for as few as 6 samples as shown in FIG. 16A and FIG. 16B, there is a noticeable shape difference as a function of particle size. The shape differences will be analyzed quantitatively in detail by sample size and particle size by computing distances between shapes, displaying distances in heat maps as well as providing the actual distance values in tables in csv files. These computations are in the sections 'Compute distances' and 'Export the Distance Matrix'.

The distance measure used is simply the Euclidean distance between normalized shapes for a given number of samples. Details of this computation are in the Matlab code and comments for the function 'MatEucDist' in the section 'Compute distances'. It should be noted that when computing distances only the normalized shapes for a given number of samples are compared to the unknown. That is because we obviously know the number of samples for the particular event under analysis.

The parameters chosen in this example are to create a spline fit with 10 times the number of points as sample points. Thus, for example for the case of 3 sample values the spline fit and normalized spline fit will have 30 points, for 12 sample values the spline fit and normalized spline fit will have 120 points. This is evident in FIG. 12A, FIG. 12B, FIG. 13A, FIG. 13B, FIG. 18A, FIG. 18B, FIG. 19A, and FIG. 19B. It is also clear that in this example dealing only with constructed samples from an original convolution function, the distance between the normalized spline fit for a given particle size compared to the normalized spline fit for other particle sizes will be zero when the comparison is to itself and greater than zero otherwise.

Reference is now made to heat maps FIG. 26-30. FIG. 26 is a heat map of distances between 3 sample normalized spline fits for 3 to 20 micron particles, in accordance with an embodiment of the present invention. FIG. 27 is a heat map of distances between 6 sample normalized spline fits for 3 to 20 micron particles, in accordance with an embodiment of the present invention. FIG. 28 is a heat map of distances between 12 sample normalized spline fits for 3 to 20 micron particles, in accordance with an embodiment of the present invention. FIG. 29 is a heat map of distances between 18 sample normalized spline fits for 3 to 20 micron particles, in accordance with an embodiment of the present invention. FIG. 30 is a heat map of distances between 24 sample normalized spline fits for 3 to 20 micron particles, in accordance with an embodiment of the present invention.

It is useful to picture these distances using a heat map. Heat maps for cases 3, 6, 12, 18 and 24 samples showing the distances between particles of different size are in FIG. 26 through FIG. 30, respectively. It is pretty clear from these heat maps that once the number of samples is greater than 6, particles of all sizes can be discriminated. It is also interesting to note that while it is easy to distinguish among the larger particles, particles less than 6 μm, which are totally contained within the excitation window are not that easily distinguished. This suggests that in order to discriminate amongst various sized particles smaller excitation windows, or at least excitation windows that are somewhat smaller than the particle or desirable. The actual numerical distance values are in Table 14, Table 15, Table 16, Table 17 and Table 18.

Particle Velocity

What is the essence of estimating the true convolution integral? What we have is a spatial convolution resulting from the emitting particle passing through the excitation beam. This spatial convolution is sampled at fixed time intervals. Since we do not know the speed of the particle nor is the particle entry into the excitation beam synchronized with the sampling, we do not know the location of the samples on the particle nor the distance between samples on the particle. If we knew the true distance from the beginning of the convolution to the end of the convolution we could use the acquired samples to estimate the shape of this convolution and consequently it's integral.

The deconvolution method described determines the geometric size of the convolution by matching the normalized particle samples to precomputed convolution functions for different size particles. A detailed example of this process is described in the section TWO EVENTS FROM THE SAME POPULATION WITH DIFFERENT NUMBER OF SAMPLES. Using this matching technique the closest particle size match to both of the particles is 4 μm. Once this is determined we know that the geometrical convolution length (based on the preselected sampling granularity) should be 100. If the geometrical particle size were determined independently one could skip this matching step and use a 4 μm particle size along with the 6 μm beam size to determine the geometrical convolution length of 100 μm.

Spline fits to the 11 points from the first event and the 16 points from the 2nd event are each summed to produce the convolution integral value shown in Table 5—Comparison of parameters derived from Event 1 and 2 samples showing that with no normalization, parameter values depend on the number of samples. Normalization to the number of samples works for particles of the same size, but will fail when comparing emission values from difference size particles as shown in the section 'DIFFERENT SIZE PARTICLES.'

So, how can we use velocity to determine the geometrical convolution length, or distance? This is straightforward. Velocity is by definition distance divided by time. Or distance is the product of velocity and time. We know the time of the event because of the fixed sampling rate and if we also knew the velocity during the event we could simply multiply the time by the velocity to get the geometric length of the event. Knowing this we could pick the correct convolution length to which the samples would be fitted. This would significantly reduce the computational load by obviating the need for the normalizing and matching computations to determine the particle size.

Reference is now made to FIGS. 31A and 31B. FIG. 31A is a plot of the ratio of the integral of a reconstructed convolution signal to that of the integral of the "true" convolution signal for given particle diameter as a function of the number of convolution samples showing that beyond about 7 to 8 samples the "reconstructed integral" is essentially equal to the "true integral," in accordance with an embodiment of the present invention; The complete results are in Table 6 below. FIG. 31B is a plot of the ratio of the integral of a reconstructed convolution signal to that of the integral of the "true" convolution signal for given particle diameter as a function of the number of convolution samples showing that beyond about 7 to 8 samples the "reconstructed integral" is essentially equal to the "true integral" viewed from the No. of Samples axis, in accordance with an embodiment of the present invention. The complete results are in Table 6 below.

The fact that reconstructing the convolution from which the convolution integral is determined provides a particle size and sample size (beyond a minimum number of samples) independent estimate of the true integrated convolution is demonstrated in FIG. 31A and FIG. 31B—Ratio of the integral of reconstructed convolution signal to that of the integral of the "true" convolution signal for given particle diameter as a function of the number of convolution samples showing that beyond about 7 to 8 samples the "reconstructed integral" is essentially equal to the "true integral." The complete results are in Table 6.

Performance of the Various Measures Derived from the Event Sample Values

As noted above, measures of the convolution samples that have been used are:
1. summing the digital signals,
2. using the peak of the digital signals or a curve fitted through them
3. averaging the digital signals The relationship of each of these measures to the true convolution depends on the particle size. In situations where only a single particle size is being used each of these measures will provide values that are fairly consistent with the integral of the true convolution that is the measure of particle emission that we desire.

On the other hand, estimating the true convolution and integrating this estimate provides a particle size independent measure of particle emission. This is demonstrated in FIG. 31A, B through FIG. 34A, B. FIG. 32A shows a plot of the ratio of the sum of the convolution samples to that of the integral of the "true" convolution signal for given particle diameter as a function of the number of convolution samples showing how the relationship between the sum and the "true convolution integral" varies as a function of particle size, in accordance with an embodiment of the present invention; The complete results are in Table 9 below. FIG. 32B is a plot of the ratio of the sum of the convolution samples to that of the integral of the "true" convolution signal for given particle diameter as a function of the number of convolution samples showing how the relationship between the sum and the "true convolution integral" varies as a function of particle size viewed from the Particle Diameter axis, in accordance with an embodiment of the present invention; The complete results are in Table 9 below.

FIG. 33A is a plot of the ratio of the maximum of the convolution samples to that of the integral of the "true" convolution signal for given particle diameter as a function of the number of convolution samples showing how the relationship between the maximum and the "true convolution integral" varies as a function of particle size, in accordance with an embodiment of the present invention; The complete results are in Table 7 below. FIG. 33B is a plot of the ratio of the maximum of the convolution samples to that of the integral of the "true" convolution signal for given particle diameter as a function of the number of convolution samples showing how the relationship between the maximum and the "true convolution integral" varies as a function of particle size viewed from the Particle Diameter axis, in accordance with an embodiment of the present invention; The complete results are in Table 7 below.

Turning to FIG. 34A, there is seen a ratio of the average of the convolution samples to that of the integral of the "true" convolution signal for given particle diameter as a function of the number of convolution samples showing how the relationship between the average and the "true convolution integral" varies as a function of particle size, in accordance with an embodiment of the present invention; The complete results are in Table 8 below. FIG. 34B shows a ratio of the average of the convolution samples to that of the integral of the "true" convolution signal for given particle diameter as a function of the number of convolution samples showing how the relationship between the average and the "true convolution integral" varies as a function of particle size viewed from the Particle Diameter axis, in accordance with an embodiment of the present invention; The complete results are in Table 8 below.

As indicated in the descriptions of each of these figures the relationship between the computed measure and the underlying true convolution integral is plotted as a function of both number of samples and particle size. We can readily see from these figures that only for the integral of the estimated convolution function, FIG. 31A,B, is the ratio of the estimate to the true convolution integral virtually one for all particle sizes once the number of samples is greater than about 5 or 6. For all other measures the ratio of the measure to the integral of the true convolution, i.e. particle emission, varies as a function of particle size. The greatest variation is for the case of using the peak of the digital signals or a curve fitted through them. Also, simply summing the sample values provide answers for the same particle that are proportional to the number of sample points.

Detailed values of the ratios are in Table 6, Table 7, Table 8 and Table 9 below. The actual values of the measures are in Table 10, Table 11, Table 12 and Table 13 below.

Check with Real Data

Keeping the Excitation Window Size Constant

We have simplified this exposition by assuming that the excitation window size remains constant. If in fact this window size varied, it would simply increase the number of reference cases since we would need a reference case for every combination of window particle size and number of samples. In principle this would not be an issue except for the increase in computation time required to compare to a significantly larger number of references.

In many cases the size of the excitation window does not vary significantly even when a particle location does.

Beam Parameters

The geometry and behavior of a Gaussian beam are governed by a set of beam parameters shown in FIG. 3, which are defined in the following.

Beam Width or Spot Size

For a Gaussian beam propagating in free space, the spot size (radius) w(z) will be at a minimum value $w_0$ at one place along the beam axis, known as the beam waist. For a beam of wavelength $\lambda$ at a distance z along the beam from the beam waist, the variation of the spot size is given by $$w(z) = w_0 \sqrt{\left(1 + \left(\frac{z}{z_R}\right)^2\right)}$$

where the origin of the z-axis is defined, without loss of generality, to coincide with the beam waist, and where $z_R = (\pi w_0^2)/\lambda$ is called the Rayleigh range.

Figure 3:
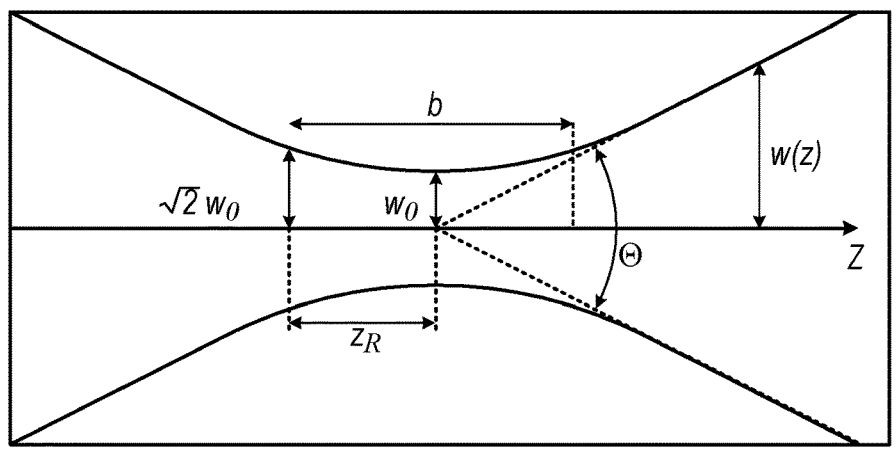

Reference is now made to FIG. 3, which is a simplified schematic illustration of a variation of a beam width of a Gaussian laser beam, in accordance with an embodiment of the present invention.

Based on the formulas above using the parameters shown in FIG. 3 describing a Gaussian beam, Table 1 below summarizes the key width and distance parameters for Gaussian beams with waists of 2, 2.5, and 3 μm respectively.

Figure 4:
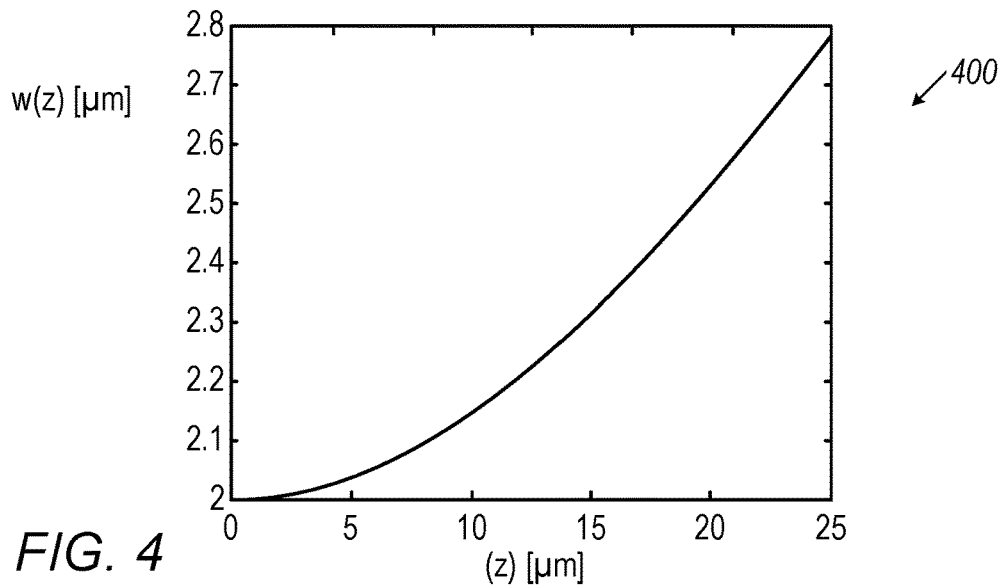
Figure 5:
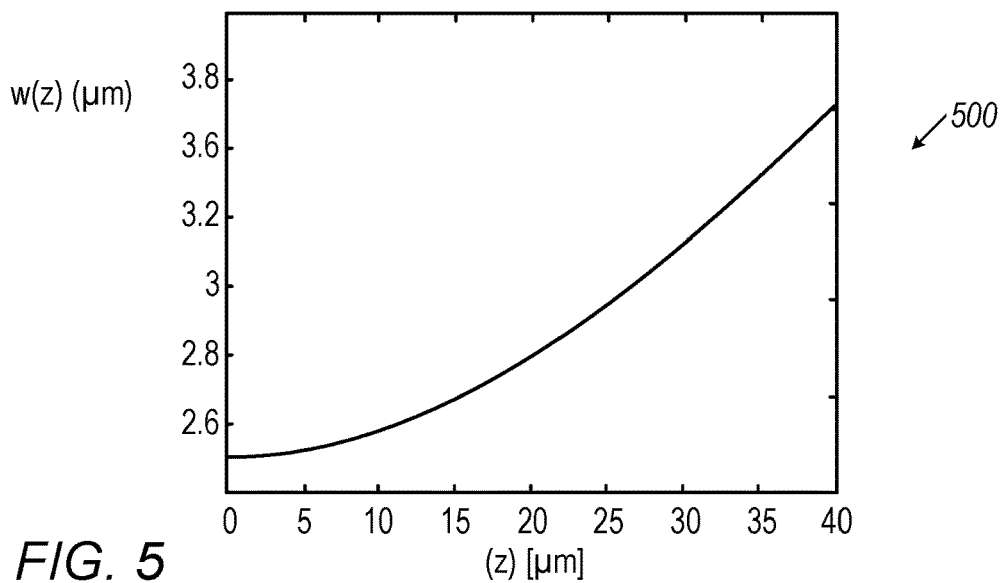

Reference is now made to FIG. 4, which is a plot 400 of a beam width as a function of a distance from a waist for a two micron beam waist, in accordance with an embodiment of the present invention. Turning also to FIG. 5, there is seen is a plot 500 of a beam width as a function of a distance from a waist for a 2.5 micron beam waist, in accordance with an embodiment of the present invention. Additionally, turning to FIG. 6, there is seen a plot 600 of a beam width as a function of a distance from a waist for a three micron beam waist, in accordance with an embodiment of the present invention.

Figure 6:
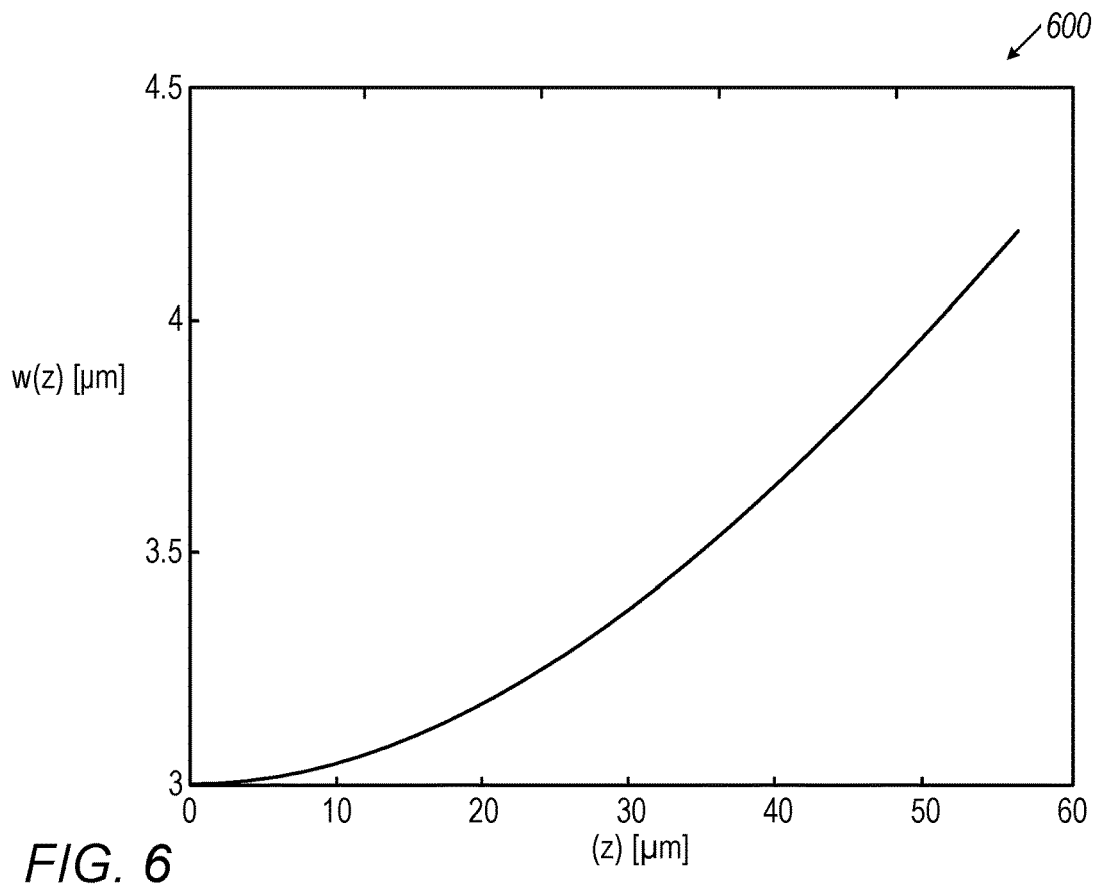

As shown in FIG. 4, FIG. 5 and FIG. 6, the increase in beam width for a distance of 25 μm from the beam waste is at most about 39% for a 2 μm beam waste, but less than 9% for a 3 μm beam waste. Thus for example in a system in which the particle location is at most 25 μm from a 3 μm beam waste the change in the excitation beam is minimal and would therefore not significantly affect the convolution. Thus in many cases only particle size must be varied.

TABLE 1

Summary of the Rayleigh range and width at the Rayleigh range for Gaussian beams with minimum waists of 2, 2.5 and 3 μm.

| Beamwidth, w0 | Parameter | Parameter Value (um) |
|---|---|---|
| 2 um | Rayleigh range, zR | 25.75 |
| 2 um | Width at Rayleigh range, wzR | 2.83 |
| 2.5 um | Rayleigh range, zR | 40.24 |
| 2.5 um | Width at Rayleigh range, wzR | 3.54 |
| 3 um | Rayleigh range, zR | 57.94 |
| 3 um | Width at Rayleigh range, wzR | 4.24 |

Different Size Particles

Figure 7A:
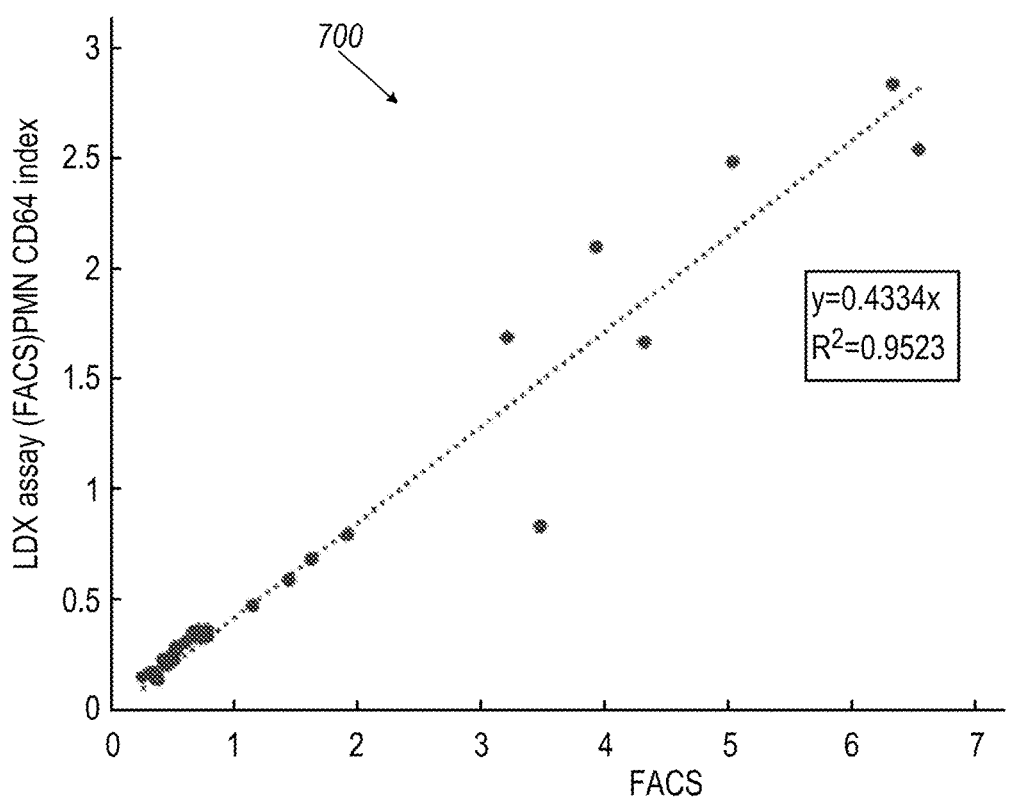

We had questioned why the slope of the best fit comparing LeukoDx assay results to those of Trillium LK-12 was not one as shown in FIG. 7A, B. FIG. 7A shows a plot 700 of a correlation of a CD64 assay (LeukoDx assay) results for PMN (neutrophils) of the present invention versus a Trillium LK-12 assay, in accordance with an embodiment of the present invention.

FIG. 7B shows a plot 750 of a correlation of a CD64 assay results for PMN (neutrophils) and Mon (monocytes) of the present invention versus a Trillium LK-12 assay, in accordance with an embodiment of the present invention.

The answer quite simply is that LeukoDx emission estimates were based on peak values of individual events.

The index values in FIG. 7A are the ratio of neutrophil emission to reference bead emission. The flow cytometer on which the Trillium LK-12 results are based provides a true estimate of particle emission independent of particle size. The peak values compared to the true emission provided by the LeukoDx assay vary as a function of particle size.

Turning to Table 7 below, we can observe that for a particle size of 5 um, approximately the size of the Trillium reference beads, the maximum value of the true convolution relative to the integral of the true convolution is approximately 0.0209 while for a particle size of approximately 14 um, approximately the size of a neutrophil or monocyte, the maximum value of the true convolution relative to the integral of the true convolution is approximately 0.0089 the ratio of the particle relative estimate to the bead relative estimate 0.0089/0.0209=0.426, which is amazingly close to the slope of 0.4334 in FIG. 7A and the slope of 0.4276 in FIG. 7B. This result is not significantly changed for the relative values of the maximum to the true integral of the convolution if 10 samples are assumed in this case for a particle size of 5, the bead, the value is 0.0199, and for a particle size of 14, the neutrophil the value is 0.00884 a ratio of 0.442. Thus, the model and analysis produced by the model predict the results we have obtained.

If averaging of the digital samples is used the change as a function of particle size is not as great and therefore we would expect the slope to be closer to one. The corresponding ratios for true convolution and 10 samples are 0.550 and 0.552 respectively.

Two Events from the Same Population with Different Number of Samples

How well will the algorithm handle 2 events from the same population with different numbers of samples? To answer this question, data from an MESF series was used. The data from a bar beginning at 631 in the histogram of the normalized Alexa 488 signature (F488NPSW) was examined, and 2 events with significantly different number of samples were selected.

Selected data values for each of these 2 events are summarized in Table 2 and Table 3 below. We will focus the analysis and demonstration on the data from the Waveband2 which is where the peak Alexa 488 emission occurs.

The first step is to create normalized spline fits for each of these 2 events. According to the parameter selected, 10 spline points per sample point will be used.

Figure 8B:
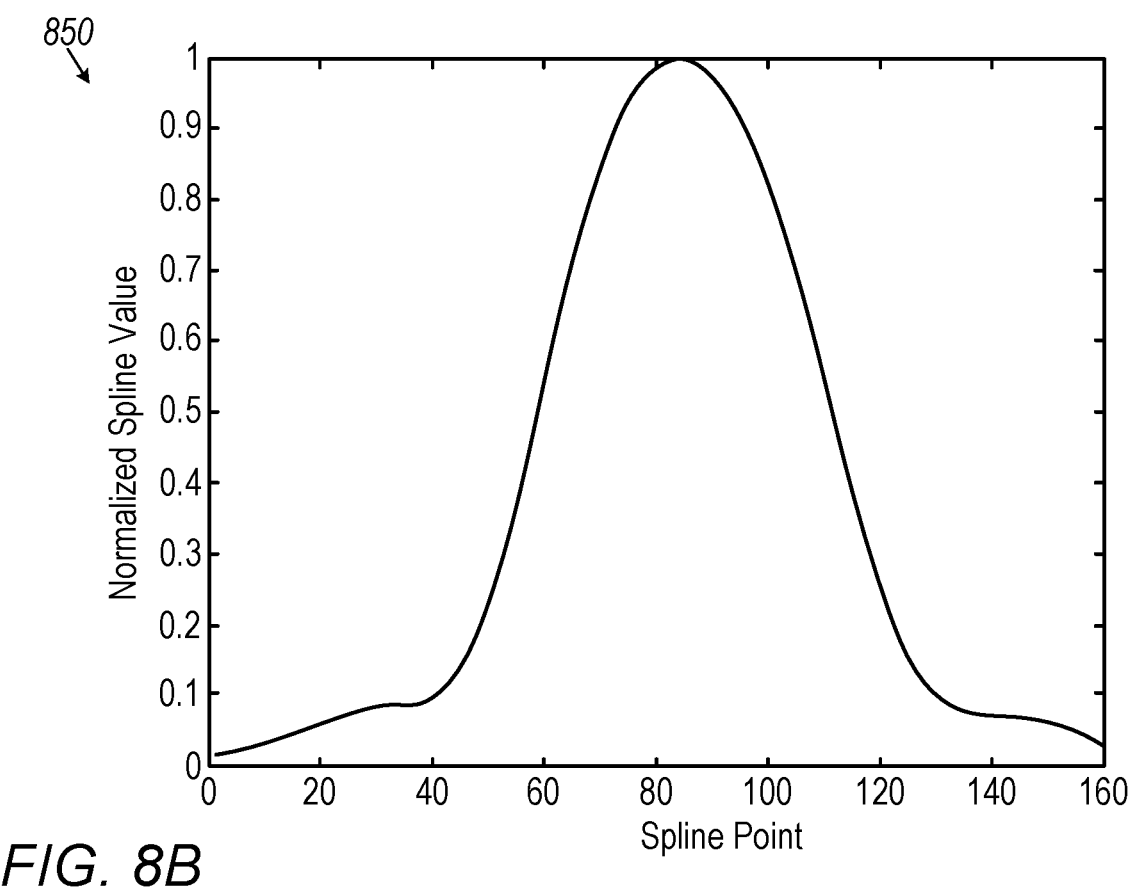

Reference is now made to FIG. 8A, which is a normalized spline plot 800 for Event 1 Waveband2 (11 sample points). Fitted spline uses 10 points per sample point; Turning to FIG. 8B, there is seen a normalized spline plot 850 for Event 2 Waveband2 (16 sample points). Fitted spline 850 uses 10 points per sample point;

The resulting normalized spline fits for each event are shown in FIGS. 8A and 8B. Event 1, which has 11 sample points, has a normalized spline fit that is 110 points long, while event 2, which has 16 sample points, has a normalized spline fit that is 160 points long.

TABLE 2

Event 1 Data

| PulseNo | PStart | PCurrent | PulseWidth-1 | Waveband1 | Waveband2 |
|---|---|---|---|---|---|
| 16 | 41500 | 41500 | 10 | 13 | 115 |
| 16 | 41500 | 41501 | 10 | 55 | 164 |
| 16 | 41500 | 41502 | 10 | 175 | 557 |
| 16 | 41500 | 41503 | 10 | 199 | 813 |
| 16 | 41500 | 41504 | 10 | 1075 | 3571 |
| 16 | 41500 | 41505 | 10 | 2283 | 7241 |
| 16 | 41500 | 41506 | 10 | 2411 | 8031 |
| 16 | 41500 | 41507 | 10 | 1575 | 5522 |
| 16 | 41500 | 41508 | 10 | 423 | 1353 |
| 16 | 41500 | 41509 | 10 | 203 | 674 |
| 16 | 41500 | 41510 | 10 | 86 | 267 |

TABLE 3

Event 2 Data

| PulseNo | PStart | PCurrent | PulseWidth-1 | Waveband1 | Waveband2 |
|---|---|---|---|---|---|
| 183 | 394869 | 394869 | 15 | 37 | 108 |
| 183 | 394869 | 394870 | 15 | 99 | 307 |
| 183 | 394869 | 394871 | 15 | 112 | 535 |
| 183 | 394869 | 394872 | 15 | 179 | 694 |
| 183 | 394869 | 394873 | 15 | 303 | 1000 |
| 183 | 394869 | 394874 | 15 | 882 | 2799 |
| 183 | 394869 | 394875 | 15 | 1673 | 5696 |
| 183 | 394869 | 394876 | 15 | 2280 | 7596 |
| 183 | 394869 | 394877 | 15 | 2469 | 8073 |
| 183 | 394869 | 394878 | 15 | 2139 | 7241 |
| 183 | 394869 | 394879 | 15 | 1662 | 5151 |

TABLE 3-continued

Event 2 Data

| PulseNo | PStart | PCurrent | PulseWidth-1 | Waveband1 | Waveband2 |
|---|---|---|---|---|---|
| 183 | 394869 | 394880 | 15 | 798 | 2548 |
| 183 | 394869 | 394881 | 15 | 297 | 950 |
| 183 | 394869 | 394882 | 15 | 213 | 607 |
| 183 | 394869 | 394883 | 15 | 166 | 497 |
| 183 | 394869 | 394884 | 15 | 108 | 226 |

The event 1 normalized spline vector was compared to the normalized spline vectors for particles between 3 and 20 μm sampled 11 times. The event 2 normalized spline vector was compared to the normalized spline vectors for particles between 3 and 20 μm sampled 16 times. As described above, the comparison is to compute the distance between the event normalized spline and the reference normalized splines. Table 4 below shows the distance between the normalized spline for each event and the corresponding particle size normalized splines for the given number of samples in each event. In both cases the minimum distance is for a particle size of 4 μm. Thus, in each case the total spline length should be 100 corresponding to an excitation of 6 μm a particle diameter of 4 μm for a total geometrical convolution length of 10 μm with 10 spline points per geometrical point.

TABLE 4

Distance between Event 1 and Event 2 and the normalized reference spline fits for 11 and 16 samples respectively showing that in both cases the closest match it to a particle of size 4 um.

| Samples Particle (um) | Event 1 11 MeDist1 | Event 2 16 MeDist2 |
|---|---|---|
| 3 | 2.391 | 2.512 |
| 4 | 2.263 | 2.374 |
| 5 | 2.276 | 2.384 |
| 6 | 2.387 | 2.517 |
| 7 | 2.601 | 2.736 |
| 8 | 2.845 | 3.007 |
| 9 | 3.081 | 3.280 |
| 10 | 3.298 | 3.530 |
| 11 | 3.496 | 3.760 |
| 12 | 3.676 | 3.966 |
| 13 | 3.831 | 4.152 |
| 14 | 3.967 | 4.322 |
| 15 | 4.090 | 4.474 |
| 16 | 4.202 | 4.608 |
| 17 | 4.303 | 4.729 |
| 18 | 4.395 | 4.840 |
| 19 | 4.475 | 4.943 |
| 20 | 4.544 | 5.035 |

As shown in Table 5 below, and described in its description, measures that depend on the sample points directly without any correction for the number of sample points, specifically Waveband2 sum and F488, the signature of Alexa 488, differ for event one and event 2 essentially in proportion to the number of samples, as can be seen quantitatively from the values of the ratio 1 to 2. Normalizing these measures by either the number of samples or a parameter related to the number of samples as is the case for F488NPSW, yields parameter values that are within about 6% or better for the 2 particles. These measures will work as long as only a single particle size is involved.

However if multiple particle sizes are to be compared as was the case in the example cited in section DIFFERENT SIZE PARTICLES, above, these measures would fail to yield consistent results proportional to the integral of the convolution. We can also see from Table 5 below that the Spline Sum representing the integral of the convolution yields values for the 2 particles that are within about 3.5%. Thus this demonstrates the method using real data.

It should be noted that while we used an integer particle size to determine the length of the spline to be fitted a non-integer particle size based on interpolating the location of the minimum could also be used. For example suppose the interpolated minimum was 4.5, then an overall convolution length of 45+60 equal 105 could have been used instead of the 40+60 equal 100 that in fact was used. This would provide an integrated convolution slightly larger than the one that was computed and perhaps one that more accurately represents the integral of the true convolution. The method illustrated here is simply to demonstrate a method recognizing that one skilled in the art can find other ways to determine the particle size from the collected data. The point is that one needs an estimate of the particle size based on the data in order to choose an appropriate overall convolution length.

TABLE 5

Comparison of parameters derived from Event 1 and 2 samples showing that with no normalization parameter values depend on the number of samples. Normalization to the number of samples works for particles of the same size, but will fail when comparing emission values from difference size particles as shown in the section '

| Event | Samples | Waveband 2 Sum | Waveband 2 Sum/# Samples | F488 | F488/# Samples | F488NP5 W | Spline Sum |
|---|---|---|---|---|---|---|---|
| Event1 | 11 | 28308 | 2573 | 30735 | 2794 | 768.393 | 279790 |
| Event2 | 16 | 44028 | 2751 | 47874 | 2992 | 759.907 | 289950 |
| Ratio 1 to 2 | 0.688 | 0.643 | 0.935 | 0.642 | 0.934 | 1.011 | 0.965 |

Figure 9:
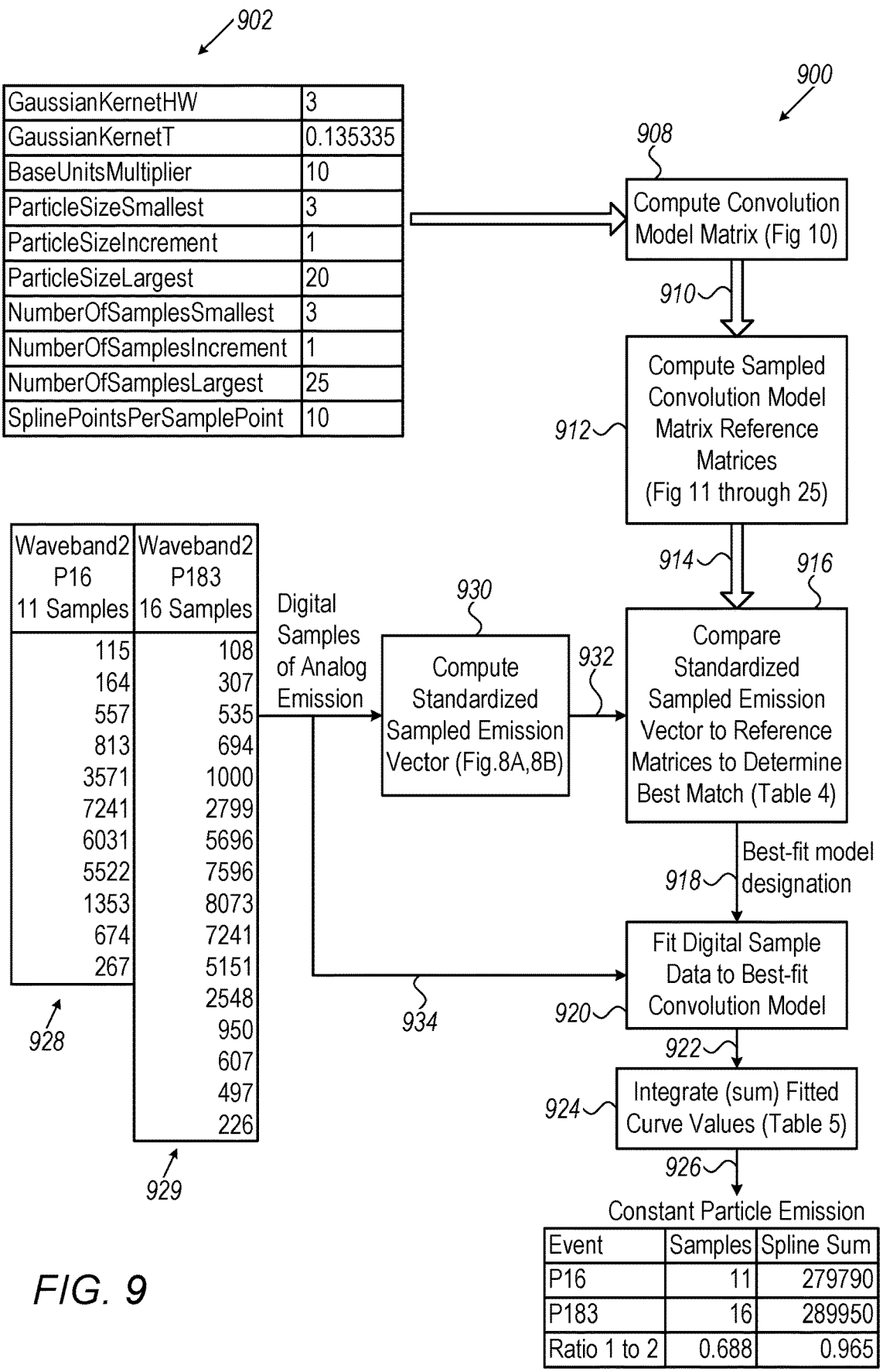

Reference is now made to FIG. 9, which is a simplified schematic illustration of a flowchart 900 of a method for deconvolving the total particle emission from the signals obtained from the physical elements of a convolution model, in accordance with an embodiment of the present invention specialized for the two real data events.

Using the physical elements, depicted in FIG. 1, information, signals and data from fluorescent particle 108 are obtained in a data obtaining step 902. The data are inputted into a convolution model matrix, for example, as shown in FIG. 10A, in a computing step 908 and a reference matrix output 910 is outputted therefrom.

In parallel, waveband samples 928 and 929 from 11 and 16 samples, respectively are inputted into a second computing step 930 for computing standardized sample emission vectors. These are exemplified in FIGS. 8A and 8B.

In a third computing step 912, data 914 from the reference matrix output 910 is sampled and reference matrices shown in FIGS. 11-25 are computed. At least one output of sampled emission vectors 914 are outputted from third computing step 912. Additionally, at least one output from the second computing step, comprising standardized sampled emission vectors 932 are compared with reference matrices data 914 in a comparing step 916 to determine a best match (see Table 4 hereinbelow) and output a best-fit model designation 918.

In a fitting step 920, samples of analog emission 934 are fitted to the best fit model designation 918, to output a best-fit convolution model output 922. The best-fit convolution model output 922 is then integrated in an integrating step 924 thereby producing a deconvolution 926 of total particle emission.

Comparison of the Prior Art to the Present Invention

In U.S. Pat. No. 5,909,278, Time-Resolved Fluorescence Decay Measurements For Flowing Particles by Deka, et al, an apparatus and method for the measurement and analysis of fluorescence for individual cells and particles in flow are described. Deka relies on the deconvolution method described by Grinvald, Analytical Biochemistry 59, 583-598 (1974), "On the analysis of Fluorescence Decay Kinetics by the Method of Least-Squares," to deconvolve the time samples of the fluorescent decay.

The deconvolution described by Deka and Grinvald is not the deconvolution of the method in this invention. The following are differences between Deka and Grinvald and the method of this invention. Deka and Grinvald describe methods that deconvolve only the time relationship between the excitation and the corresponding fluorescent decay and between the finite sampling of the decay and the true underlying time function. The following is reproduced from Deka column 7 line 24 through column 8 line 58.

The present method is applied to fluorescent microspheres and to biological cells stained with different dyes. Specifically, the measurement and analysis of both single and double exponential decays is demonstrated for individual Chinese hamster ovary (line CHO) cells stained with propidium iodide (PI) only, Fluorescein isothiocyanate (FITC) only, and with both PI and FITC. The system was tested using standard fluorescent microspheres with known fluorescence decay and lifetime. Reference will now be made in detail to the present preferred embodiments of the invention, an example of which is illustrated in the accompanying drawings. For time-domain fluorescence decay measurements, the sample (i.e., a cell or a particle) is excited by a pulse of light. The true fluorescence signal due to this pulsed excitation is the convolution of the impulse response function of the fluorescence decay and the excitation light pulse. Since the measurement system itself has a finite response time, the recorded fluorescence pulse is actually the convolution of the true fluorescence signal and the instrument's response function. In other words, the measured fluorescence signal is the convolution of the fluorescence decay and the system response function, where the system response function is the convolution of the excitation light pulse and the instrument's response function. Thus, the system response function is given by and the recorded fluorescence signal is given by $$e(t)=[L(t) \otimes S(t)], \tag{1}$$

and the recorded fluorescence signal is given by $$F(t)=e(t) \otimes D(t), \tag{2}$$

where L(t), S(t), D(t) are the temporal profile of the excitation light pulse, the instrument response function, and the impulse response function of the fluorescence decay, respectively. The symbol ® represents a convolution between two functions. In an actual experiment, the system response function, e(t), is obtained by measuring the scattered signal from a nonfluorescent particle, and deconvolutes it from the measured fluorescence signal, F(t), to extract D(t). In integral notation $$F(t) = \int_0^t D(t')e(t-t')dt'. \quad (3)$$

If the base line of the optical excitation is not zero, i.e., the transient pulses are superimposed upon a continuous wave (cw) intensity K, the system response function, represented by the scattered signal, is given by $$E(t) = K + e(t) \quad (4)$$

The measured fluorescence intensity due to the above excitation is given by $$F(t) = \int_0^t D(t')(K + e(t-t'))dt', \text{ from which}$$

$$F(t) = K\int_0^t D(t')dt' + \int_0^t D(t')e(t-t')dt',$$

$$F(t) = K' + \int_0^t D(t')e(t-t')dt', \text{ or}$$

$$F(t) = K' + \int_0^t D(t-t')e(t')dt' \quad (5)$$

The first term on the right hand side of Equation (5) represents the steady-state fluorescence due to the cw part of the excitation. The second term gives the pulsed component of the fluorescence signal and is superimposed on the cw intensity. If the respective base lines are subtracted from the scattered signal (K in Equ. 4) and the fluorescence signal (K' in Equ. 5), the baseline corrected pair of signals behave as if there was no cw excitation in the first place. Therefore, the impulse response function of the fluorescence decay can be extracted by deconvoluting the baseline corrected function, $E(t)-K$, from the baseline corrected fluorescence signal $F(t)-K'$. For digitally acquired datasets, however, the start time may have a nonzero value, say $t_R$, that marks an instant before the pulse has a chance to rise above the baseline. In that situation, the lower limit for the above integration, that gives the convolution of the decay law with the response function, should be taken as $t_R$, and a numerical integration performed accordingly. The deconvolution is accomplished by the method of Grinvald et al. Here, a model decay function $$D(t) = \sum_i \alpha_i \exp(-t/\tau_i) \quad (6)$$

is assumed and is convoluted with the measured systems response function repeatedly, each time varying the parameters ($\alpha_i$ and $\tau_i$, until the difference between the reconvoluted signal and the experimental fluorescence signal is minimized. This procedure is known as the iterative reconvolution method. It is straightforward to extend the fitting procedure to arbitrary nonexponential decay functions that may not be expressed as the sum of a finite number of exponential decays. See, e.g. Ware, supra.

The first observed difference is that the case discussed by both Deka and Grinvald the entire particle is illuminated and the issue to be resolved is that the illumination is not an impulse so that in fact the finite duration of the excitation illumination causes multiple decay emissions. The objective of Deka and Grinvald is to determine the fluorescence decay impulse response from the observed convolution of the desired impulse response with the finite excitation. Thus, were the particle in fact illuminated by an impulse excitation the resulting emission would in fact be the desired impulse response. In contrast, in the present invention were it erroneously assumed that the time domain convolution considered by Deka and Grinvald was analogous to the spatial domain convolution given by $$e(x,y) = \iint G(x-\xi, y-\upsilon)E(\xi,\upsilon)d\xi d\upsilon$$

in equation 1 below and the excitation was an impulse given by $$G(x,y) = \delta(x,y)$$

Then the resulting emission would be given by $$e(x,y) = \iint \delta(x-\xi, y-\upsilon)E(\xi,\upsilon)d\xi d\upsilon = E(x,y)$$

the emission of the particle at the point x,y. This is not the total emission of the particle which is the objective of the present invention. Therefore, the method of Deka and Grinvald does not handle the situation where the excitation covers only part of the particle. The method of this invention determines the total particle emission regardless of whether the entire particle or only part of the particle is excited during the observation of the particle emission.

In essence Deka and Grinvald require a linear time invariant system, whereas the present invention handles a linear time varying system as well. The ability of the present invention to handle a linear time varying system is demonstrated by the example shown in FIGS. 8A, 8B and 9 and Tables 2, 3, 4 and 5, where particles of the same size one sampled 11 times in the other sampled 16 times (this is the time varying component) yield essentially the same total emission.

Deka requires time invariance in order to use the scatter signal from a second particle in order to determine the starting time correction and system characterization function. Again were the Deka method used to characterize the system function in the 2 particle example below it would fail because the different velocities of the 2 particles yielded different numbers of samples for each of the 2 particles.

Thus, the method of Deka and Grinvald is not capable of producing the total emission of a particle under conditions where the method of the present invention can do so.

| Deconvolution Method Attributes |
| --- |
| 1.1 Model excitation and particle fluorescence to yield geometrical observed emission convolution model |
| 1.1.1 Geometrical convolution depends only on excitation geometry and particle emission geometry |
| 1.1.2 Geometrical convolution is independent of particle velocity and number of samples |
| 1.2 Measured signal is sampled geometrical convolution |
| 1.2.1 Know number of samples |
| 1.2.2 Do not know geometrical location of the time samples |
| 1.2.3 Therefore do not know geometrical length of sampled convolution |
| 1.2.4 Therefore this is a linear time varying system |

Deconvolution Method Attributes 1.3 To estimate the geometric convolution, fit sample values to a curve with the geometric length of the "true" convolution
1.4 How to find the length of the true convolution?
1.4.1 Match normalized convolution samples to a precomputed table of normalized convolution matrices for each particle size and number of samples
1.4.1.1 function [ConvolutionMatrix, SampledConvolutionMatrix, . . . SpSampledConvolutionMatrix, NrmSpSampledConvolutionMatrix] . . . = BuildReferenceMatrices(DeconParamValues)
1.4.1.2 Find best match of normalized sample curve to normalized convolutions using a distance measure (i.e. min distance).
The best match is the closest match to a normalized convolution for the given number of samples and therefore determines the particle size.
Given the particle size and the known size of the excitation the geometric size of the convolution is determined.
1.4.2 Independently determine particle size.
Given the particle size and the known size of the excitation the geometric size of the convolution is determined.
1.4.3 Determine geometrical convolution length from independent measurement of particle velocity and # of samples
1.4.3.1 Distance = Velocity * Time
1.4.3.2 Velocity is measured.
Time = # of samples * sample interval.
Thus geometrical convolution length = Distance, which can be computed.
1.5 Compute total particle emission
1.5.1 From Fubini's theorem, if f and g are integrable functions, then the integral of their convolution on the whole space is simply obtained as the product of their integrals:
1.5.2 Thus
$\int_{R^d} (f * g)(x)dx = (\int_{R^d} f(x)dx)(\int_{R^d} g(x)dx)$.
1.5.3 And the total particle emission is given by
$\int_{R^d} f(x)dx = (\int_{R^d} (f * g)dx)/(\int_{R^d} g(x)dx)$
or
$\int_{R^d} f(x)dx = K * (\int_{R^d} (f * g)dx$
1.5.4 Setting K = 1, i.e. using the integral of the geometrical convolution simply scales the particle total emission. This is generally of no consequence since there are multiple electrooptical scale factors that are not determined and are irrelevant since emission values need only maintain a fixed relationship to one another.
1.6 Thus, integral of the convolution is the product of the integral of the excitation and the integral of particle emission (total emission)
1.6.1 Integral of the excitation is known and constant
1.6.2 Either divide integral of convolution by integral of excitation or use integral of convolution as K*integral of emission
1.7 Determine total particle emission for each particle independently
1.8 Allows total particle emission to be determined for capillary slit flow cytometer regardless of particle size variation Method requires that all of the following attributes be satisfied: 1.1, 1.2, 1.3, 1.4, 1.5, 1.6, 1.7, 1.8.

| Prior Art | Attributes Satisfied | Basic Method | Fails to Teach |
|---|---|---|---|
| 2 Slit Scan Flow Cytometry | | | |
| 2.1 Real-Time Classification of Chromosomes in Slit Scan Flow Cytometry | 1.2 Measured signal is sampled geometrical convolution, but no mention of the word "convolution" in the document | "For each chromosome the fluorescence emission is sampled at 256 instants and digitized. This results in time resolved profiles of the distribution of the fluorescence along the chromosome axis. These profiles allow a classification according to centromeric index (DNA contents of the long chromosome arm divided by total DNA contents), number of centromeres (e.g., dicentrics), or specific DNA sequences (e.g., in the case of translocations)." | 1.1, 1.2, 1.3, 1.4, 1.5, 1.6, 1.7, 1.8. |
| 2.2 Depth of field and improved resolution of slit-scan flow systems | 1.2 Measured signal is sampled geometrical convolution, but no mention of the word "convolution" in the document | "In a slit-scan flow cytometer particles specifically labelled by fluorochromes (e.g., cells, chromosomes) are aligned coaxially in a flow stream. One by another they pass a ribbon-like shaped laser beam with a diameter smaller than the particle length. Although several slit-scan flow systems have been developed during the last two decades, a complete description of the theory of optical resolution under the real experimental conditions used as well as a description how to | 1.1, 1.2, 1.3, 1.4, 1.5, 1.6, 1.7, 1.8. |

| Prior Art | Attributes Satisfied | Basic Method | Fails to Teach |
|---|---|---|---|
| | | overcome experimental limitations are missing. Often, resolution values are estimated under the assumption of ideal Gaussian beam propagation. These estimates suffer from a discrepancy to practical implementation. Here, some of these effects in slit-scan optics will be discussed from a more theoretical point of view. In order to obtain an acceptable depth of field, a focal width around 2 um appears to be an optimum under the regime of Gaussian beam propagation. However, in practice, effects due to thick lenses, finite apertures, chromatic aberrations, or the ellipticity of the laser beam overshadow this result and influence the laser beam shape. To further improve the resolution with a high depth of field, new concepts are required. Therefore, a combination of an interference fringe pattern of two coherent laser beams for excitation (fringe-scanning) with a slit-scan detection of the incoherent fluorescence light is introduced. Preliminary experience of the first experimental realization will be discussed." | |
| 2.3 Signal Processing in Slit-Scan Flow Cytometry | 1.2 Measured signal is sampled geometrical convolution, but no mention of the word "convolution" in the document | "In order to measure physical aspects of cell-cell interaction using a flow cytometer, it is necessary to measure the individual scatter and/or fluorescence signals of adherent cells (conjugates). In principle these individual signals can be obtained by using slit-scan illumination. If the 2 cells that form the conjugate have similar sizes, the hydrodynamic forces in the funnel of a typical flow cell will orient the cells along the direction of flow. Therefore a slit-scan illumination can resolve the individual cells. In previous work, the total slit-scan profile was measured using a transient recorder and was analyzed with a computer afterwards. For the particular problem of conjugated cells, one is only interested in the peak heights of the signals from individual cells. In this report we describe a simple analog signal processing system for measuring the 2 peak heights of a slit-scan signal from 2 adherent cells. The timing of this system is based upon one input signal that always shows 2 peaks when a conjugate passes the slit, e.g., forward light scatter, and the first derivative of that signal. The zero crossing points of the first derivative indicate the maxima and minima in the signal and can be used to determine the contact region (minimum signal). The principle of taking the derivative of an input signal was used by van Oven et al. to identify the centromere position in chromosomes by the determination of the so-called pulse dip index. They did not measure the separate peak heights of the signal, but they used the derivative to calculate a new parameter, the ratio of the profile up to the first local minimum and the total area of the profile. Our signal processing system has a modular construction which can be used for different purposes by changing the logic circuit. This logic circuit can be easily changed because it is designed using an erasable programmable logic device (EPLD). Two peak detectors are used for every parameter, which requires double peak evaluation. The processing time is dependent on the length of the signal, and the double peak evaluation causes no extra delay. Measurements on the fluorescence changes of a potential sensitive dye, induced by interactions between natural killer (NK) cells and their target cells (K562), are presented as an illustration of the possibilities of this signal processing system." | 1.1, 1.2, 1.3, 1.4, 1.5, 1.6, 1.7, 1.8. |
| 2.4 Slit-Scan Flow Cytometry for Consistent High Resolution DNA Analysis of X- and Y-Chromosomes Bearing Sperm | 1.2 Measured signal is sampled geometrical convolution, but no mention of the word "convolution" in the document | This paper describes the application of slit-scan flow cytometry for accurate DNA analysis of X- and Y-chromosome bearing sperm. The introduction of the slit-scanning technique was initiated to improve the consistency in resolution of the X and Y population from donor to donor. An optimal resolution is essential for high purity sorting of X and Y sperm, as the difference in DNA | 1.1, 1.2, 1.3, 1.4, 1.5, 1.6, 1.7, 1.8. |

| Prior Art | Attributes Satisfied | Basic Method | Fails to Teach |
|---|---|---|---|
| | | content is small (3-4%) in most mammals. This difference is the discriminatory parameter for the flow cytometric sorting of the two populations. Our approach was to focus on the role of the sperm tail in the detection process. Slit scan flow cytometric analysis allows the whole sperm to be spatially analyzed along the direction of flow. Sperm were stained with Dansyl Lysine, a UV excitable fluorescent membrane dye, which stained the head, midpiece, and principal piece. Analysis of these stained sperm showed that there was no difference between the relative number of sperm that travel headfirst or tailfirst through the detection zone of the flow cytometer. The influence of sperm with coiled tails on DNA analysis was also investigated. The proportion of sperm with coiled tails influences semen quality. The standard X-Y separation procedure uses Hoechst 33342, which stains all intact sperm, both living and dead. Propidium iodide was added to discriminate the dead sperm population. Slit-scan analysis showed that measurement of a sample containing a high proportion of living sperm with coiled W s results in an inferior DNA histogram and reduced X-Y resolution. Sperm with coiled tails can result in a lower detected fluorescence intensity, but the reason for this is unclear. Slit-scan flow cytometry allows exclusion of sperm with coiled tails from the analysis, resulting in a restoration of high resolution of X- and Y-chromosome bearing sperm populations. | |
| 2.5 Instrument for Real-Time Pulse-Shape Analysis of Slit-Scan Flow Cytometry Signals | 1.2 Measured signal is sampled geometrical convolution, but no mention of the word "convolution" in the document | "An instrument is described which analyses shapes of fluorescence profiles generated by particles passing through the focussed laser beam of a flow cytometer. The output signal of this pulse-shape analyzer is used as input for the signal processing electronics of a commercial flow cytometer system. The instrument detects dips in pulse-profiles; a shape parameter named Pulse Dip Index (PDI) is defined as the ratio of the integrated signal from the beginning of the pulse until the first dip, relative to the integrated signal of the complete profile. This PDI is similar to the Centromeric Index of chromosomes The composition of aggregates in mixtures of fluorescent particles of different sizes was evaluated by PDI analysis. In our experiments the PDI was determined within 30 us from the onset of the pulse-profile and particles with a specified morphology of interest were selected for on-line registration of their profiles as digitized pulse-shapes. In a cell sorter system, the PDI can be used as a parameter for sorting." | 1.1, 1.2, 1.3, 1.4, 1.5, 1.6, 1.7, 1.8. |
| 3 Distribution Deconvolution | | | |
| 3.1 US 2005/0009060 | None | The present disclosure provides systems for multiplexed multitarget screening of cell populations having one or more wild type or mutated ligand targets and measuring cell responses to ligands using high throughput screening techniques, including flowcytometry (FCM). The method includes the steps of: 1) developing cell populations to be screened; 2) staining cell populations using one or more fluorochromes to yield a distinct excitation/emission signature for each cell population; 3) combining labelled cell populations into a single mixed suspension; 4) analyzing populations to resolve them on the basis of their unique signature; and 5) resolving individual populations and deconvoluting data to extract meaningful information about populations. | 1.1, 1.2, 1.3, 1.4, 1.5, 1.6, 1.7, 1.8. Individual particle analysis based on deconvolving the individual particle's signature from the sampled geometric convolution of the particle emission and excitation. |

-continued

| Prior Art | Attributes Satisfied | Basic Method | Fails to Teach |
|---|---|---|---|
| 3.1.1 MULTIPLEXED MULTI TARGET SCREENING METHOD resolving individual populations and deconvoluting data to extract meaningful information about populations. | | | |
| 3.2 US 5,633,945 | None | Cell samples, stained with a fluorescent dye, taken up by DNA in the individual cells, are scanned with a cytometer, which measures the integrated value of fluorescent light/cell. The integrated values of all of the cells are compiled to create an histogram of cell counts versus integrated fluorescent light, representing a cell population of (a) cells having a complement of DNA, but not in the process of division (G0 phase), (b) cells having two full compliments of DNA, but which have not actually divided into two cells (G2 phase) and (c) cells which are in the process of replicating their DNA (S, separation phase). The percentages of cells in each of the phases, represented in the histogram as separated peaks of sizes proportional to the Go and G2 populations, and separation S phase population, aids in the prognosis of a patient's cancer development. More serious malignancy is indicated by increased S and G2 phase populations. Errors, e.g., resulting from statistical errors, focusing problems, inaccurate measurement of background. etc., in the integrated values and compilation of cells in the histogram, affect the accuracy and prognostic value of the peaks and separation phase, and are corrected by a method, wherein the convolution of error function with the signal function (representing the number of cells, as determined by the fluorescence measurements. with a DNA content of a specified value), is modeled and the error function removed, by deconvolution, from the G0 and G2 peaks and the S phase. | 1.1, 1.2, 1.3, 1.4, 1.5, 1.6, 1.7, 1.8. Individual particle analysis based on deconvolving the individual particle's signature from the sampled geometric convolution of the particle emission and excitation. |
| 3.2.1 Thus the cell distribution $S(x)$ is derived from the histogram $H(x)$ and the error function $E(\Delta x)$ by taking the inverse fast Fourier transform of the quantity the fast Fourier transform of the histogram divided by the fast Fourier transform of the error function. 3.2.2 ACCURACY IN CELL MITOSIS ANALYSIS In accordance with the method of the present invention with an inverse fast Fourier transform a relation between the histogram $H(x)$ cell distribution $S(x)$ and error function $E(\Delta x)$ is represented as: $S(x) = F - 1 (F(H(x))/F(E(\Delta x)))$ | | | |
| 3.3 3. U.S. Pat. No. 7,842,512 | None | A method for photochemical reactor characterization includes an application of using dyed microspheres exposed to UV irradiation under a collimated-beam system. Particle specific fluorescence intensity measurements are conducted using samples form the collimated beam and flow-through reactor results using flow cytometry. A numerical model may be used to simulate the behavior of the reactor system to provide a particle-tracking algorithm to interrogate the flow and intensity field simulations for purposes of developing a particle specific estimate of the dose delivery. A method for measuring UV dose distribution delivery in photochemical reactors is | 1.1, 1.2, 1.3, 1.4, 1.5, 1.6, 1.7, 1.8. Individual particle analysis based on deconvolving the individual particle's signature from the sampled geometric convolution of the particle emission and excitation. |

| Prior Art | Attributes Satisfied | Basic Method | Fails to Teach |
|---|---|---|---|
| | | provided that includes introducing microspheres labeled with a photochemically-active compound in a UV reactor. The labeled micro spheres are harvested downstream of the irradiated Zone of a UV reactor and exposed to UV irradiation under a collimated beam of UV irradiation. The method further includes quantifying a UV dose-response behavior, conducting fluorescence intensity measurement on the labeled microspheres from the UV reactor, and developing an estimate of a dose distribution delivered by a UV reactor based on the numerical deconvolution of the sum of the UV dose response behavior and fluorescent intensity of exposed micro spheres. | |
| 3.3.1 DYED MICROSPHERES FOR CHARACTERIZATION OF PHOTOCHEMICAL REACTOR BEHAVIOR. The deconvolution process may be achieved by importing data from the flow cytometry analyses into a MATLAB program or equivalent program | | | |
| 4 Fluorescence Lifetime Measurement | | | See detailed discussion in Section COMPARISON OF THE PRIOR ART TO THE PRESENT INVENTION above |
| 4.1 Grinvald, Analytical Biochemistry 59, 583-598 (1974), "On the analysis of Fluorescence Decay Kinetics by the Method of Least-Squares," | 1.2 Measured signal is sampled geometrical convolution | Analysis of fluorescence decay kinetics aims at the determination of the analytic expression and the numerical values of the pertinent parameters which describe the decay process. In the well-known method of least-squares, one assumes a plausible functional form for the decay data and adjusts the values of the parameters until the statistically best fit is obtained between the data and the calculated decay function, i.e., until the sum of the weighted squares of the residuals is at a minimum. It is shown that proper weighting of the squares of the residuals may markedly improve the quality of the analysis. Such weighting requires information about the character of the experimental noise, which is often available, e.g., when the noise is due to counting error in photon-counting techniques. Furthermore, dramatic improvements in the accuracy of the analysis may often be achieved by use of auxiliary information available about the system studied. For example, the preexponents in a multiexponential fluorescence decay of a mixture of chromophores (such as tryptophan residues in a protein molecule) may sometimes be estimated independently; much higher accuracy can then be attained for the decay lifetimes by analysis of the decay kinetics. It is proposed that the shape of the autocorrelation function of the weighted residuals may serve as a convenient criterion for the quality of fit between the experimental data and the decay function obtained by analysis. The above conclusions were reached by analysis of computer-simulated experiments, and the usefulness of this approach is illustrated. The importance of stating the uncertainties in the estimated parameters inherent in the analysis of decay kinetics is stressed. | 1.1, 1.2, 1.3, 1.4, 1.5, 1.6, 1.7, 1.8. Individual particle analysis based on deconvolving the individual particle's signature from the sampled geometric convolution of the particle emission and excitation. |
| 4.2 5,909,278, TIME-RESOLVED FLUORESCENCE DECAY MEASUREMENTS FOR FLOWING PARTICLES by Deka | 1.2 Measured signal is sampled geometrical convolution | Time-resolved fluorescence decay measurements for flowing particles. An apparatus and method for the measurement and analysis of fluorescence for individual cells and particles in flow are described, wherein the rapid measurement capabilities of flow cytometry and the robust measurement and analysis procedures of time-domain fluorescence lifetime spectroscopy are combined. A pulse-modulated cw | 1.1, 1.2, 1.3, 1.4, 1.5, 1.6, 1.7, 1.8. Individual particle analysis based on deconvolving the individual particle's signature from the sampled geometric |

-continued

| Prior Art | Attributes Satisfied | Basic Method | Fails to Teach |
|---|---|---|---|
| | | laser is employed for excitation of the particles, The characteristics and the repetition rate of the excitation pulses can be readily adjusted to accommodate for fluorescence decays having a wide range of lifetimes. | convolution of the particle emission and excitation. |
| 5 Particle Position Measurement 5.1 US20150112627 | 1.2 Measured signal is sampled geometrical convolution, but no mention of the word "convolution" in the document | "To provide a technique capable of highly accurately measure the intensity and the spectrum of fluorescence and scattered light by effectively correcting measurement error that occurs due to variation of flow positions of fine particles in a channel. A data correction method for a fine particle measurement device is provided, which includes an intensity detection procedure capable of detecting light generated from a fine, particle by emitting light onto the fine particle flowing through a channel, and obtaining intensity information about the light, a position detection procedure capable of obtaining position information about the fine particle, and a correction procedure for correcting the intensity information on the basis of the position information." | 1.1, 1.2, 1.3, 1.4, 1.5, 1.6, 1.7, 1.8. Individual particle analysis based on deconvolving the individual particle's signature from the sampled geometric convolution of the particle emission and excitation. |
| 5.2 US20150276575 | 1.2 Measured signal is sampled geometrical convolution, but no mention of the word "convolution" in the document | "A microparticle measuring apparatus for highly accurately detecting the position of a microparticle flowing through a flow channel includes a light irradiation unit for irradiating a microparticle flowing through a flow channel with light, and a scattered light detection unit for detecting scattered light from the microparticle, including an objective lens for collecting light from the microparticle, a light splitting element for dividing the scattered light from the light collected by the objective lens, into first and second scattered light, a first scattered light detector for receiving an S-polarized light component, and an astigmatic element disposed between the light splitting element and the first scattered light detector, and making the first scattered light astigmatic. A relationship between a length L from a rear principal point of the objective lens to a front principal point of the astigmatic element, and a focal length f of the astigmatic element satisfies the following formula I. 1.5f≤L≤2.5f (I)" | 1.1, 1.2, 1.3, 1.4, 1.5, 1.6, 1.7, 1.8. Individual particle analysis based on deconvolving the individual particle's signature from the sampled geometric convolution of the particle emission and excitation. |

REFERENCES

Ayers, G. R., and J. Christopher Dainty. "Iterative blind deconvolution method and its applications." Optics letters 13.7 (1988): 547-549.

Biggs, David S C, and Mark Andrews. "Acceleration of iterative image restoration algorithms." Applied optics 36.8 (1997): 1766-1775.

Fahmy, Mamdouh F., et al. "A new fast iterative blind deconvolution algorithm." Journal of Signal and Information Processing 3.01 (2012): 98.

Fish, D. A., et al. "Blind deconvolution by means of the Richardson-Lucy algorithm." JOSA A 12.1 (1995): 58-65.

Holmes, Timothy J., and Yi-Hwa Liu. "Acceleration of maximum-likelihood image restoration for fluorescence microscopy and other noncoherent imagery." JOSA A 8.6 (1991): 893-907.

Ulmer, Waldemar. "Inverse problem of linear combinations of Gaussian convolution kernels (deconvolution) and some applications to proton/photon dosimetry and image processing." Inverse Problems 26.8 (2010): 085002.

Ulmer, W. "Convolution/deconvolution of generalized Gaussian kernels with applications to proton/photon physics and electron capture of charged particles." Journal of Physics: Conference Series. Vol. 410. No. 1. IOP Publishing, 2013.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

| DeconParameterInput001.xlsx | | | | | | | | |
|---|---|---|---|---|---|---|---|---|
| Gaussian KernelHW | Gaussian KernelT | BaseUnits Multiplier | ParticleSize Smallest | ParticleSize Increment | ParticleSize Largest | NumberOf Samples Smallest | NumberOf Samples Increment | NumberOf Samples Largest | SplinePoints PerSample Point |
| 3 | 0.135335 | 10 | 3 | 1 | 20 | 3 | 1 | 25 | 10 |

TABLE 6

Relative Convolution Sum Matrix: RelConvolutionSumMatrix
Ratio of the integral of reconstructed convolution signal to that of the integral of the "true" convolution signal for given particle diameter as a function of the number of convolution samples showing that beyond about 7 to 8 samples the "reconstructed integral" is essentially equal to the "true integral."

| | | Number of Samples | | | | | | | | | | |
|---|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 1 | 1.4830 | 1.1472 | 0.9419 | 0.9863 | 1.0018 | 0.9898 | 0.9852 | 1.0141 | 1.0131 | 0.9856 | 0.9994 |
| 4 | 1 | 1.5166 | 1.1211 | 0.9582 | 0.9857 | 0.9886 | 0.9832 | 0.9969 | 0.9993 | 1.0123 | 0.9999 | 0.9999 |
| 5 | 1 | 1.5160 | 1.1064 | 0.9397 | 0.9829 | 0.9788 | 1.0031 | 1.0001 | 0.9878 | 1.0106 | 1.0119 | 0.9884 |
| 6 | 1 | 1.4924 | 1.1514 | 0.9715 | 0.9825 | 0.9977 | 0.9939 | 1.0077 | 0.9983 | 1.0098 | 0.9942 | 1.0101 |
| 7 | 1 | 1.4426 | 1.1502 | 0.9620 | 0.9853 | 0.9869 | 0.9875 | 0.9883 | 0.9981 | 1.0079 | 0.9980 | 0.9994 |
| 8 | 1 | 1.3897 | 1.1513 | 0.9929 | 0.9897 | 0.9779 | 1.0005 | 0.9939 | 0.9937 | 1.0065 | 1.0031 | 1.0006 |
| 9 | 1 | 1.3424 | 1.1815 | 0.9903 | 0.9950 | 0.9906 | 0.9931 | 0.9966 | 1.0017 | 1.0057 | 1.0034 | 0.9990 |
| 10 | 1 | 1.3013 | 1.1768 | 1.0218 | 0.9986 | 0.9856 | 0.9881 | 1.0006 | 0.9965 | 1.0042 | 0.9954 | 1.0001 |
| 11 | 1 | 1.2659 | 1.1709 | 1.0222 | 1.0028 | 0.9824 | 0.9836 | 0.9887 | 0.9989 | 1.0028 | 0.9972 | 0.9941 |
| 12 | 1 | 1.2352 | 1.1811 | 1.0497 | 1.0080 | 0.9948 | 0.9938 | 0.9909 | 1.0009 | 1.0018 | 1.0007 | 1.0041 |
| 13 | 1 | 1.2085 | 1.1677 | 1.0499 | 1.0140 | 0.9923 | 0.9901 | 0.9939 | 0.9953 | 1.0012 | 0.9987 | 0.9987 |
| 14 | 1 | 1.1850 | 1.1538 | 1.0712 | 1.0204 | 0.9907 | 0.9869 | 0.9956 | 0.9906 | 1.0007 | 0.9938 | 0.9999 |
| 15 | 1 | 1.1644 | 1.1506 | 1.0696 | 1.0269 | 1.0013 | 0.9968 | 0.9886 | 0.9908 | 0.9997 | 0.9976 | 0.9970 |
| 16 | 1 | 1.1461 | 1.1370 | 1.0848 | 1.0331 | 1.0011 | 0.9931 | 0.9904 | 0.9929 | 0.9988 | 1.0007 | 0.9981 |
| 17 | 1 | 1.1297 | 1.1244 | 1.0813 | 1.0389 | 1.0015 | 0.9972 | 0.9960 | 0.9904 | 0.9981 | 0.9975 | 0.9950 |
| 18 | 1 | 1.1150 | 1.1202 | 1.0912 | 1.0442 | 1.0120 | 0.9944 | 0.9974 | 0.9971 | 0.9976 | 0.9954 | 1.0006 |
| 19 | 1 | 1.1018 | 1.1089 | 1.0851 | 1.0487 | 1.0130 | 1.0040 | 0.9928 | 0.9955 | 0.9973 | 0.9973 | 0.9979 |
| 20 | 1 | 1.0898 | 1.0986 | 1.0891 | 1.0525 | 1.0142 | 1.0017 | 0.9936 | 0.9975 | 0.9973 | 0.9984 | 0.9983 |

| | Number of Samples | | | | | | | | | | | |
|---|---|---|---|---|---|---|---|---|---|---|---|---|
| PartSize (μm) | 14 | 15 | 16 | 17 | 18 | 19 | 20 | 21 | 22 | 23 | 24 | 25 |
| 3 | 1.0005 | 0.9954 | 1.0138 | 1.0000 | 0.9973 | 1.0135 | 0.9954 | 1.0005 | 0.9971 | 0.9862 | 0.9985 | 1.0014 |
| 4 | 0.9969 | 0.9872 | 1.0007 | 1.0016 | 0.9980 | 1.0001 | 0.9969 | 1.0126 | 1.0003 | 1.0000 | 1.0004 | 1.0000 |
| 5 | 1.0031 | 1.0002 | 1.0019 | 0.9986 | 0.9967 | 0.9884 | 0.9979 | 1.0008 | 1.0028 | 1.0115 | 0.9979 | 0.9991 |
| 6 | 0.9994 | 1.0002 | 1.0104 | 1.0003 | 1.0000 | 0.9990 | 1.0018 | 1.0102 | 1.0002 | 0.9982 | 1.0016 | 1.0103 |
| 7 | 1.0092 | 1.0002 | 1.0003 | 0.9910 | 1.0024 | 1.0005 | 1.0018 | 1.0002 | 1.0006 | 0.9989 | 0.9983 | 1.0000 |
| 8 | 0.9975 | 1.0078 | 1.0014 | 0.9980 | 1.0025 | 1.0001 | 1.0025 | 1.0077 | 0.9990 | 1.0023 | 0.9922 | 1.0013 |
| 9 | 0.9958 | 1.0023 | 1.0069 | 1.0018 | 1.0015 | 0.9999 | 1.0006 | 0.9998 | 0.9989 | 1.0000 | 0.9964 | 0.9989 |
| 10 | 0.9993 | 0.9977 | 0.9998 | 1.0060 | 0.9977 | 0.9992 | 0.9984 | 1.0059 | 0.9998 | 1.0000 | 0.9994 | 1.0001 |
| 11 | 0.9996 | 0.9948 | 1.0012 | 1.0008 | 1.0054 | 1.0009 | 0.9997 | 0.9994 | 0.9946 | 0.9985 | 0.9981 | 0.9947 |
| 12 | 1.0003 | 0.9995 | 1.0048 | 1.0018 | 1.0032 | 1.0048 | 1.0008 | 1.0025 | 1.0047 | 1.0031 | 1.0013 | 0.9994 |
| 13 | 1.0027 | 0.9996 | 0.9999 | 0.9983 | 0.9975 | 1.0000 | 1.0044 | 0.9992 | 1.0000 | 1.0009 | 1.0008 | 0.9994 |
| 14 | 1.0007 | 0.9996 | 1.0012 | 0.9990 | 1.0006 | 0.9960 | 0.9972 | 1.0040 | 0.9973 | 0.9961 | 1.0015 | 0.9991 |
| 15 | 0.9955 | 1.0031 | 1.0032 | 0.9962 | 0.9996 | 0.9993 | 0.9999 | 0.9991 | 1.0036 | 1.0000 | 0.9989 | 1.0008 |
| 16 | 1.0014 | 1.0004 | 0.9999 | 0.9988 | 1.0023 | 1.0002 | 1.0025 | 1.0032 | 0.9999 | 1.0033 | 1.0025 | 1.0001 |
| 17 | 0.9985 | 0.9982 | 1.0011 | 1.0005 | 0.9972 | 0.9993 | 0.9970 | 0.9990 | 1.0023 | 0.9995 | 1.0031 | 1.0008 |
| 18 | 0.9983 | 0.9961 | 1.0021 | 1.0025 | 0.9969 | 1.0004 | 0.9999 | 1.0028 | 1.0008 | 0.9996 | 1.0007 | 1.0029 |
| 19 | 0.9958 | 0.9994 | 0.9996 | 1.0007 | 1.0007 | 0.9998 | 0.9985 | 0.9990 | 1.0003 | 1.0007 | 0.9985 | 0.9999 |
| 20 | 1.0006 | 0.9986 | 1.0003 | 0.9998 | 0.9989 | 1.0000 | 1.0009 | 1.0023 | 0.9998 | 1.0001 | 1.0009 | 0.9999 |

TABLE 7

Relative Maximum Sampled Convolution Matrix: RelMaxSampledConvolutionMatrix
Ratio of the maximum of the convolution samples to that of the integral of the "true" convolution signal for given particle diameter as a function of the number of convolution samples showing the relationship between the maximum and the "true convolution integral" varies as a function of particle size.

| | | Number of Samples | | | | | | | | | | |
|---|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 0.02499 | 0.02499 | 0.01718 | 0.02499 | 0.02199 | 0.02499 | 0.02319 | 0.02499 | 0.02412 | 0.02499 | 0.02412 | 0.02499 |
| 4 | 0.02298 | 0.02298 | 0.01510 | 0.02298 | 0.02014 | 0.02298 | 0.02117 | 0.02298 | 0.02199 | 0.02298 | 0.02232 | 0.02298 |
| 5 | 0.02086 | 0.02086 | 0.01353 | 0.02086 | 0.01822 | 0.02086 | 0.01951 | 0.02086 | 0.01985 | 0.02086 | 0.02039 | 0.02086 |
| 6 | 0.01881 | 0.01881 | 0.01290 | 0.01881 | 0.01650 | 0.01881 | 0.01748 | 0.01881 | 0.01800 | 0.01881 | 0.01822 | 0.01881 |

TABLE 7-continued

Relative Maximum Sampled Convolution Matrix: RelMaxSampledConvolutionMatrix
Ratio of the maximum of the convolution samples to that of the integral of the "true" convolution signal for given particle diameter as a function of the number of convolution samples showing the relationship between the maximum and the "true convolution integral" varies as a function of particle size.

| | | | | | | | | | | | | |
|---|---|---|---|---|---|---|---|---|---|---|---|---|
| 7 | 0.01677 | 0.01677 | 0.01189 | 0.01677 | 0.01502 | 0.01677 | 0.01574 | 0.01677 | 0.01613 | 0.01677 | 0.01644 | 0.01677 |
| 8 | 0.01500 | 0.01500 | 0.01104 | 0.01500 | 0.01373 | 0.01500 | 0.01441 | 0.01500 | 0.01464 | 0.01500 | 0.01473 | 0.01500 |
| 9 | 0.01351 | 0.01351 | 0.01057 | 0.01351 | 0.01259 | 0.01351 | 0.01305 | 0.01351 | 0.01321 | 0.01351 | 0.01334 | 0.01351 |
| 10 | 0.01228 | 0.01228 | 0.00987 | 0.01228 | 0.01155 | 0.01228 | 0.01189 | 0.01228 | 0.01207 | 0.01228 | 0.01211 | 0.01228 |
| 11 | 0.01124 | 0.01124 | 0.00924 | 0.01124 | 0.01064 | 0.01124 | 0.01090 | 0.01124 | 0.01104 | 0.01124 | 0.01112 | 0.01124 |
| 12 | 0.01035 | 0.01035 | 0.00880 | 0.01035 | 0.00985 | 0.01035 | 0.01010 | 0.01035 | 0.01021 | 0.01035 | 0.01023 | 0.01035 |
| 13 | 0.00959 | 0.00959 | 0.00824 | 0.00959 | 0.00915 | 0.00959 | 0.00936 | 0.00959 | 0.00945 | 0.00959 | 0.00950 | 0.00959 |
| 14 | 0.00893 | 0.00893 | 0.00773 | 0.00893 | 0.00855 | 0.00893 | 0.00872 | 0.00893 | 0.00880 | 0.00893 | 0.00884 | 0.00893 |
| 15 | 0.00836 | 0.00836 | 0.00734 | 0.00836 | 0.00802 | 0.00836 | 0.00819 | 0.00836 | 0.00825 | 0.00836 | 0.00829 | 0.00836 |
| 16 | 0.00785 | 0.00785 | 0.00692 | 0.00785 | 0.00754 | 0.00785 | 0.00769 | 0.00785 | 0.00775 | 0.00785 | 0.00779 | 0.00785 |
| 17 | 0.00740 | 0.00740 | 0.00655 | 0.00740 | 0.00712 | 0.00740 | 0.00725 | 0.00740 | 0.00732 | 0.00740 | 0.00734 | 0.00740 |
| 18 | 0.00700 | 0.00700 | 0.00625 | 0.00700 | 0.00674 | 0.00700 | 0.00686 | 0.00700 | 0.00692 | 0.00700 | 0.00695 | 0.00700 |
| 19 | 0.00664 | 0.00664 | 0.00594 | 0.00664 | 0.00640 | 0.00664 | 0.00652 | 0.00664 | 0.00657 | 0.00664 | 0.00659 | 0.00664 |
| 20 | 0.00631 | 0.00631 | 0.00566 | 0.00631 | 0.00610 | 0.00631 | 0.00620 | 0.00631 | 0.00624 | 0.00631 | 0.00627 | 0.00631 |

| | Number of Samples | | | | | | | | | | | |
|---|---|---|---|---|---|---|---|---|---|---|---|---|
| PartSize (μm) | 14 | 15 | 16 | 17 | 18 | 19 | 20 | 21 | 22 | 23 | 24 | 25 |
| 3 | 0.02446 | 0.02499 | 0.02473 | 0.02499 | 0.02473 | 0.02499 | 0.02473 | 0.02499 | 0.02473 | 0.02499 | 0.02490 | 0.02499 |
| 4 | 0.02258 | 0.02298 | 0.02258 | 0.02298 | 0.02278 | 0.02298 | 0.02278 | 0.02298 | 0.02278 | 0.02298 | 0.02278 | 0.02298 |
| 5 | 0.02039 | 0.02086 | 0.02058 | 0.02086 | 0.02058 | 0.02086 | 0.02072 | 0.02086 | 0.02072 | 0.02086 | 0.02072 | 0.02086 |
| 6 | 0.01840 | 0.01881 | 0.01855 | 0.01881 | 0.01855 | 0.01881 | 0.01855 | 0.01881 | 0.01867 | 0.01881 | 0.01867 | 0.01881 |
| 7 | 0.01656 | 0.01677 | 0.01656 | 0.01677 | 0.01665 | 0.01677 | 0.01665 | 0.01677 | 0.01665 | 0.01677 | 0.01671 | 0.01677 |
| 8 | 0.01481 | 0.01500 | 0.01487 | 0.01500 | 0.01487 | 0.01500 | 0.01492 | 0.01500 | 0.01492 | 0.01500 | 0.01492 | 0.01500 |
| 9 | 0.01339 | 0.01351 | 0.01343 | 0.01351 | 0.01343 | 0.01351 | 0.01346 | 0.01351 | 0.01346 | 0.01351 | 0.01346 | 0.01351 |
| 10 | 0.01215 | 0.01228 | 0.01219 | 0.01228 | 0.01222 | 0.01228 | 0.01222 | 0.01228 | 0.01224 | 0.01228 | 0.01224 | 0.01228 |
| 11 | 0.01115 | 0.01124 | 0.01117 | 0.01124 | 0.01119 | 0.01124 | 0.01119 | 0.01124 | 0.01119 | 0.01124 | 0.01121 | 0.01124 |
| 12 | 0.01028 | 0.01035 | 0.01030 | 0.01035 | 0.01030 | 0.01035 | 0.01032 | 0.01035 | 0.01032 | 0.01035 | 0.01033 | 0.01035 |
| 13 | 0.00952 | 0.00959 | 0.00954 | 0.00959 | 0.00955 | 0.00959 | 0.00957 | 0.00959 | 0.00957 | 0.00959 | 0.00957 | 0.00959 |
| 14 | 0.00888 | 0.00893 | 0.00889 | 0.00893 | 0.00890 | 0.00893 | 0.00890 | 0.00893 | 0.00891 | 0.00893 | 0.00891 | 0.00893 |
| 15 | 0.00830 | 0.00836 | 0.00832 | 0.00836 | 0.00832 | 0.00836 | 0.00833 | 0.00836 | 0.00834 | 0.00836 | 0.00834 | 0.00836 |
| 16 | 0.00780 | 0.00785 | 0.00781 | 0.00785 | 0.00782 | 0.00785 | 0.00783 | 0.00785 | 0.00783 | 0.00785 | 0.00784 | 0.00785 |
| 17 | 0.00736 | 0.00740 | 0.00737 | 0.00740 | 0.00738 | 0.00740 | 0.00738 | 0.00740 | 0.00738 | 0.00740 | 0.00739 | 0.00740 |
| 18 | 0.00696 | 0.00700 | 0.00697 | 0.00700 | 0.00697 | 0.00700 | 0.00698 | 0.00700 | 0.00698 | 0.00700 | 0.00698 | 0.00700 |
| 19 | 0.00660 | 0.00664 | 0.00661 | 0.00664 | 0.00662 | 0.00664 | 0.00662 | 0.00664 | 0.00663 | 0.00664 | 0.00663 | 0.00664 |
| 20 | 0.00628 | 0.00631 | 0.00629 | 0.00631 | 0.00629 | 0.00631 | 0.00630 | 0.00631 | 0.00630 | 0.00631 | 0.00630 | 0.00631 |

TABLE 8

Relative Average Sampled Convolution Matrix: RelAvgSampledConvolutionMatrix
Ratio of the average of the convolution samples to that of the integral of the "true" convolution signal for given particle diameter as a function of the number of convolution samples showing the relationship between the average and the "true convolution integral" varies as a function of particle size.

| | Number of Samples | | | | | | | | | | | |
|---|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 0.01111 | 0.00834 | 0.00860 | 0.00885 | 0.00946 | 0.00975 | 0.00973 | 0.00984 | 0.01025 | 0.01034 | 0.01015 | 0.01037 |
| 4 | 0.01000 | 0.00767 | 0.00755 | 0.00811 | 0.00854 | 0.00864 | 0.00871 | 0.00897 | 0.00908 | 0.00929 | 0.00926 | 0.00932 |
| 5 | 0.00909 | 0.00696 | 0.00677 | 0.00726 | 0.00773 | 0.00777 | 0.00806 | 0.00815 | 0.00816 | 0.00843 | 0.00851 | 0.00837 |
| 6 | 0.00833 | 0.00627 | 0.00645 | 0.00678 | 0.00706 | 0.00727 | 0.00734 | 0.00754 | 0.00755 | 0.00771 | 0.00766 | 0.00783 |
| 7 | 0.00769 | 0.00559 | 0.00595 | 0.00615 | 0.00651 | 0.00664 | 0.00675 | 0.00683 | 0.00698 | 0.00711 | 0.00709 | 0.00715 |
| 8 | 0.00714 | 0.00500 | 0.00552 | 0.00579 | 0.00604 | 0.00611 | 0.00635 | 0.00639 | 0.00645 | 0.00659 | 0.00661 | 0.00664 |
| 9 | 0.00667 | 0.00451 | 0.00529 | 0.00534 | 0.00564 | 0.00578 | 0.00589 | 0.00596 | 0.00606 | 0.00614 | 0.00617 | 0.00619 |
| 10 | 0.00625 | 0.00409 | 0.00494 | 0.00508 | 0.00527 | 0.00539 | 0.00548 | 0.00562 | 0.00565 | 0.00575 | 0.00575 | 0.00581 |
| 11 | 0.00588 | 0.00375 | 0.00462 | 0.00475 | 0.00495 | 0.00504 | 0.00514 | 0.00523 | 0.00534 | 0.00540 | 0.00542 | 0.00543 |
| 12 | 0.00556 | 0.00345 | 0.00440 | 0.00455 | 0.00468 | 0.00481 | 0.00490 | 0.00496 | 0.00505 | 0.00510 | 0.00514 | 0.00518 |
| 13 | 0.00526 | 0.00320 | 0.00412 | 0.00429 | 0.00443 | 0.00454 | 0.00463 | 0.00470 | 0.00476 | 0.00483 | 0.00485 | 0.00488 |
| 14 | 0.00500 | 0.00298 | 0.00387 | 0.00412 | 0.00422 | 0.00429 | 0.00438 | 0.00448 | 0.00450 | 0.00459 | 0.00459 | 0.00464 |
| 15 | 0.00476 | 0.00279 | 0.00367 | 0.00391 | 0.00402 | 0.00411 | 0.00420 | 0.00424 | 0.00429 | 0.00437 | 0.00439 | 0.00441 |
| 16 | 0.00455 | 0.00262 | 0.00346 | 0.00376 | 0.00385 | 0.00391 | 0.00400 | 0.00405 | 0.00411 | 0.00416 | 0.00420 | 0.00421 |
| 17 | 0.00435 | 0.00247 | 0.00327 | 0.00357 | 0.00369 | 0.00374 | 0.00382 | 0.00389 | 0.00392 | 0.00398 | 0.00401 | 0.00402 |
| 18 | 0.00417 | 0.00233 | 0.00313 | 0.00344 | 0.00354 | 0.00360 | 0.00365 | 0.00373 | 0.00377 | 0.00381 | 0.00383 | 0.00387 |
| 19 | 0.00400 | 0.00221 | 0.00297 | 0.00328 | 0.00340 | 0.00345 | 0.00353 | 0.00356 | 0.00362 | 0.00366 | 0.00368 | 0.00371 |
| 20 | 0.00385 | 0.00210 | 0.00283 | 0.00315 | 0.00328 | 0.00332 | 0.00338 | 0.00343 | 0.00348 | 0.00352 | 0.00355 | 0.00357 |

TABLE 8-continued

Relative Average Sampled Convolution Matrix: RelAvgSampledConvolutionMatrix
Ratio of the average of the convolution samples to that of the integral of the "true" convolution signal
for given particle diameter as a function of the number of convolution samples showing the relationship between the
average and the "true convolution integral" varies as a function of particle size.

| PartSize (μm) | Number of Samples | | | | | | | | | | | |
|---|---|---|---|---|---|---|---|---|---|---|---|---|
| | 14 | 15 | 16 | 17 | 18 | 19 | 20 | 21 | 22 | 23 | 24 | 25 |
| 3 | 0.01043 | 0.01044 | 0.01068 | 0.01057 | 0.01058 | 0.01079 | 0.01062 | 0.01071 | 0.01069 | 0.01060 | 0.01075 | 0.01080 |
| 4 | 0.00934 | 0.00930 | 0.00947 | 0.00952 | 0.00952 | 0.00957 | 0.00956 | 0.00974 | 0.00964 | 0.00966 | 0.00969 | 0.00970 |
| 5 | 0.00855 | 0.00857 | 0.00862 | 0.00862 | 0.00864 | 0.00859 | 0.00869 | 0.00875 | 0.00878 | 0.00888 | 0.00877 | 0.00880 |
| 6 | 0.00780 | 0.00784 | 0.00796 | 0.00791 | 0.00794 | 0.00795 | 0.00800 | 0.00808 | 0.00802 | 0.00802 | 0.00806 | 0.00815 |
| 7 | 0.00726 | 0.00723 | 0.00727 | 0.00723 | 0.00734 | 0.00735 | 0.00738 | 0.00739 | 0.00740 | 0.00741 | 0.00741 | 0.00744 |
| 8 | 0.00666 | 0.00677 | 0.00676 | 0.00676 | 0.00681 | 0.00681 | 0.00685 | 0.00690 | 0.00686 | 0.00690 | 0.00684 | 0.00692 |
| 9 | 0.00621 | 0.00628 | 0.00634 | 0.00633 | 0.00635 | 0.00636 | 0.00638 | 0.00639 | 0.00640 | 0.00642 | 0.00641 | 0.00644 |
| 10 | 0.00583 | 0.00586 | 0.00589 | 0.00595 | 0.00593 | 0.00595 | 0.00597 | 0.00603 | 0.00600 | 0.00601 | 0.00602 | 0.00604 |
| 11 | 0.00549 | 0.00549 | 0.00556 | 0.00557 | 0.00562 | 0.00561 | 0.00562 | 0.00563 | 0.00562 | 0.00565 | 0.00566 | 0.00565 |
| 12 | 0.00519 | 0.00521 | 0.00526 | 0.00527 | 0.00529 | 0.00532 | 0.00531 | 0.00535 | 0.00535 | 0.00535 | 0.00535 | 0.00536 |
| 13 | 0.00493 | 0.00494 | 0.00496 | 0.00497 | 0.00498 | 0.00501 | 0.00505 | 0.00504 | 0.00505 | 0.00506 | 0.00507 | 0.00508 |
| 14 | 0.00468 | 0.00469 | 0.00472 | 0.00473 | 0.00475 | 0.00474 | 0.00476 | 0.00480 | 0.00478 | 0.00479 | 0.00482 | 0.00482 |
| 15 | 0.00443 | 0.00448 | 0.00450 | 0.00449 | 0.00452 | 0.00453 | 0.00455 | 0.00455 | 0.00458 | 0.00458 | 0.00458 | 0.00460 |
| 16 | 0.00425 | 0.00426 | 0.00428 | 0.00429 | 0.00432 | 0.00433 | 0.00435 | 0.00436 | 0.00436 | 0.00438 | 0.00439 | 0.00438 |
| 17 | 0.00405 | 0.00407 | 0.00410 | 0.00411 | 0.00412 | 0.00413 | 0.00414 | 0.00416 | 0.00418 | 0.00418 | 0.00420 | 0.00420 |
| 18 | 0.00389 | 0.00389 | 0.00393 | 0.00395 | 0.00394 | 0.00397 | 0.00397 | 0.00400 | 0.00400 | 0.00400 | 0.00401 | 0.00403 |
| 19 | 0.00372 | 0.00375 | 0.00377 | 0.00378 | 0.00380 | 0.00381 | 0.00381 | 0.00382 | 0.00383 | 0.00384 | 0.00384 | 0.00386 |
| 20 | 0.00359 | 0.00360 | 0.00363 | 0.00363 | 0.00364 | 0.00366 | 0.00367 | 0.00369 | 0.00369 | 0.00369 | 0.00370 | 0.00371 |

TABLE 9

Relative Sum Sampled Convolution Matrix: RelSumSampledConvolutionMatrix
Ratio of the sum of the convolution samples to that of the integral of the "true" convolution signal for
given particle diameter as a function of the number of convolution samples showing the relationship between the sum
and the "true convolution integral" varies as a function of particle size.

| PartSize (μm) | UnSamp | Number of Samples | | | | | | | | | | |
|---|---|---|---|---|---|---|---|---|---|---|---|---|
| | | 3 | 4 | 5 | 6 | 7 | 8 | 9 | 10 | 11 | 12 | 13 |
| 3 | 1 | 0.0250 | 0.0344 | 0.0443 | 0.0568 | 0.0682 | 0.0779 | 0.0886 | 0.1025 | 0.1138 | 0.1218 | 0.1348 |
| 4 | 1 | 0.0230 | 0.0302 | 0.0405 | 0.0512 | 0.0605 | 0.0697 | 0.0807 | 0.0908 | 0.1022 | 0.1111 | 0.1212 |
| 5 | 1 | 0.0209 | 0.0271 | 0.0363 | 0.0464 | 0.0544 | 0.0645 | 0.0734 | 0.0816 | 0.0927 | 0.1021 | 0.1088 |
| 6 | 1 | 0.0188 | 0.0258 | 0.0339 | 0.0424 | 0.0509 | 0.0587 | 0.0679 | 0.0755 | 0.0849 | 0.0919 | 0.1018 |
| 7 | 1 | 0.0168 | 0.0238 | 0.0308 | 0.0390 | 0.0465 | 0.0540 | 0.0614 | 0.0698 | 0.0782 | 0.0850 | 0.0930 |
| 8 | 1 | 0.0150 | 0.0221 | 0.0289 | 0.0362 | 0.0428 | 0.0508 | 0.0575 | 0.0645 | 0.0725 | 0.0793 | 0.0863 |
| 9 | 1 | 0.0135 | 0.0211 | 0.0267 | 0.0338 | 0.0405 | 0.0471 | 0.0537 | 0.0606 | 0.0676 | 0.0740 | 0.0805 |
| 10 | 1 | 0.0123 | 0.0197 | 0.0254 | 0.0316 | 0.0377 | 0.0439 | 0.0506 | 0.0565 | 0.0632 | 0.0690 | 0.0755 |
| 11 | 1 | 0.0112 | 0.0185 | 0.0238 | 0.0297 | 0.0353 | 0.0411 | 0.0471 | 0.0534 | 0.0594 | 0.0650 | 0.0706 |
| 12 | 1 | 0.0104 | 0.0176 | 0.0228 | 0.0281 | 0.0337 | 0.0392 | 0.0446 | 0.0505 | 0.0561 | 0.0616 | 0.0674 |
| 13 | 1 | 0.0096 | 0.0165 | 0.0215 | 0.0266 | 0.0317 | 0.0370 | 0.0423 | 0.0476 | 0.0531 | 0.0582 | 0.0635 |
| 14 | 1 | 0.0089 | 0.0155 | 0.0206 | 0.0253 | 0.0300 | 0.0351 | 0.0403 | 0.0450 | 0.0505 | 0.0550 | 0.0603 |
| 15 | 1 | 0.0084 | 0.0147 | 0.0195 | 0.0241 | 0.0288 | 0.0336 | 0.0381 | 0.0429 | 0.0480 | 0.0526 | 0.0574 |
| 16 | 1 | 0.0079 | 0.0138 | 0.0188 | 0.0231 | 0.0274 | 0.0320 | 0.0365 | 0.0411 | 0.0458 | 0.0504 | 0.0548 |
| 17 | 1 | 0.0074 | 0.0131 | 0.0179 | 0.0221 | 0.0261 | 0.0306 | 0.0350 | 0.0392 | 0.0438 | 0.0481 | 0.0522 |
| 18 | 1 | 0.0070 | 0.0125 | 0.0172 | 0.0212 | 0.0252 | 0.0292 | 0.0336 | 0.0377 | 0.0419 | 0.0459 | 0.0504 |
| 19 | 1 | 0.0066 | 0.0119 | 0.0164 | 0.0204 | 0.0242 | 0.0282 | 0.0321 | 0.0361 | 0.0402 | 0.0442 | 0.0482 |
| 20 | 1 | 0.0063 | 0.0113 | 0.0158 | 0.0197 | 0.0232 | 0.0270 | 0.0308 | 0.0348 | 0.0387 | 0.0425 | 0.0464 |

| PartSize (μm) | Number of Samples | | | | | | | | | | | |
|---|---|---|---|---|---|---|---|---|---|---|---|---|
| | 14 | 15 | 16 | 17 | 18 | 19 | 20 | 21 | 22 | 23 | 24 | 25 |
| 3 | 0.1461 | 0.1566 | 0.1708 | 0.1796 | 0.1904 | 0.2049 | 0.2124 | 0.2249 | 0.2352 | 0.2438 | 0.2580 | 0.2700 |
| 4 | 0.1308 | 0.1396 | 0.1515 | 0.1618 | 0.1714 | 0.1818 | 0.1913 | 0.2046 | 0.2121 | 0.2222 | 0.2324 | 0.2424 |
| 5 | 0.1197 | 0.1285 | 0.1379 | 0.1466 | 0.1555 | 0.1632 | 0.1739 | 0.1837 | 0.1932 | 0.2041 | 0.2105 | 0.2199 |
| 6 | 0.1092 | 0.1176 | 0.1273 | 0.1345 | 0.1428 | 0.1510 | 0.1600 | 0.1698 | 0.1765 | 0.1846 | 0.1935 | 0.2037 |
| 7 | 0.1017 | 0.1085 | 0.1162 | 0.1229 | 0.1320 | 0.1396 | 0.1476 | 0.1551 | 0.1629 | 0.1703 | 0.1779 | 0.1861 |
| 8 | 0.0932 | 0.1015 | 0.1081 | 0.1148 | 0.1226 | 0.1295 | 0.1370 | 0.1450 | 0.1509 | 0.1587 | 0.1642 | 0.1729 |
| 9 | 0.0869 | 0.0941 | 0.1014 | 0.1076 | 0.1143 | 0.1208 | 0.1276 | 0.1342 | 0.1408 | 0.1477 | 0.1538 | 0.1609 |
| 10 | 0.0817 | 0.0879 | 0.0943 | 0.1012 | 0.1067 | 0.1131 | 0.1193 | 0.1265 | 0.1320 | 0.1383 | 0.1446 | 0.1509 |
| 11 | 0.0769 | 0.0824 | 0.0889 | 0.0947 | 0.1011 | 0.1066 | 0.1124 | 0.1183 | 0.1236 | 0.1300 | 0.1358 | 0.1412 |
| 12 | 0.0727 | 0.0782 | 0.0842 | 0.0895 | 0.0952 | 0.1010 | 0.1062 | 0.1122 | 0.1177 | 0.1231 | 0.1284 | 0.1340 |
| 13 | 0.0690 | 0.0741 | 0.0793 | 0.0845 | 0.0897 | 0.0952 | 0.1010 | 0.1058 | 0.1111 | 0.1165 | 0.1218 | 0.1269 |
| 14 | 0.0654 | 0.0703 | 0.0755 | 0.0803 | 0.0855 | 0.0901 | 0.0952 | 0.1009 | 0.1053 | 0.1101 | 0.1157 | 0.1205 |
| 15 | 0.0620 | 0.0672 | 0.0720 | 0.0763 | 0.0813 | 0.0860 | 0.0909 | 0.0956 | 0.1008 | 0.1053 | 0.1099 | 0.1149 |
| 16 | 0.0595 | 0.0640 | 0.0685 | 0.0730 | 0.0778 | 0.0822 | 0.0870 | 0.0916 | 0.0959 | 0.1008 | 0.1053 | 0.1096 |
| 17 | 0.0567 | 0.0611 | 0.0656 | 0.0699 | 0.0741 | 0.0785 | 0.0827 | 0.0873 | 0.0919 | 0.0960 | 0.1007 | 0.1049 |

TABLE 9-continued

Relative Sum Sampled Convolution Matrix: RelSumSampledConvolutionMatrix
Ratio of the sum of the convolution samples to that of the integral of the "true" convolution signal for given particle diameter as a function of the number of convolution samples showing the relationship between the sum and the "true convolution integral" varies as a function of particle size.

| 18 | 0.0544 | 0.0584 | 0.0629 | 0.0671 | 0.0709 | 0.0754 | 0.0795 | 0.0839 | 0.0880 | 0.0920 | 0.0963 | 0.1007 |
| 19 | 0.0521 | 0.0563 | 0.0602 | 0.0643 | 0.0683 | 0.0723 | 0.0762 | 0.0803 | 0.0844 | 0.0884 | 0.0922 | 0.0964 |
| 20 | 0.0503 | 0.0540 | 0.0580 | 0.0618 | 0.0656 | 0.0695 | 0.0734 | 0.0774 | 0.0811 | 0.0850 | 0.0889 | 0.0927 |

TABLE 10

Convolution Sum Matrix: ConvolutionSumMatrix
Sum of the estimated convolution as a function of particle size (PartSize) and number of samples in the estimate.
The UnSamp column is the sum of the "original reference" convolution.

| | | | | | | Number of Samples | | | | | | |
|---|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 25039 | 37134 | 28726 | 23583 | 24695 | 25084 | 24784 | 24668 | 25392 | 25368 | 24679 | 25023 |
| 4 | 44514 | 67511 | 49906 | 42651 | 43876 | 44005 | 43764 | 44376 | 44481 | 45062 | 44508 | 44511 |
| 5 | 69552 | 105439 | 76955 | 65358 | 68363 | 68079 | 69768 | 69561 | 68703 | 70289 | 70381 | 68745 |
| 6 | 100156 | 149469 | 115318 | 97300 | 98404 | 99925 | 99543 | 100928 | 99981 | 101135 | 99574 | 101171 |
| 7 | 136323 | 196664 | 156796 | 131140 | 134316 | 134533 | 134619 | 134725 | 136066 | 137398 | 136046 | 136239 |
| 8 | 178054 | 247448 | 205002 | 176795 | 176225 | 174119 | 178140 | 176965 | 176937 | 179206 | 178601 | 178165 |
| 9 | 225350 | 302509 | 266243 | 223167 | 224220 | 223236 | 223788 | 224588 | 225744 | 226643 | 226106 | 225126 |
| 10 | 278210 | 362040 | 327402 | 284263 | 277823 | 274206 | 274893 | 278383 | 277244 | 279368 | 276921 | 278251 |
| 11 | 336634 | 426134 | 394171 | 344123 | 337580 | 330711 | 331128 | 332840 | 336248 | 337576 | 335686 | 334635 |
| 12 | 400622 | 494839 | 473186 | 420541 | 403837 | 398548 | 398133 | 396967 | 400968 | 401356 | 400913 | 402279 |
| 13 | 470175 | 568186 | 549035 | 493613 | 476762 | 466576 | 465531 | 467289 | 467962 | 470732 | 469542 | 469563 |
| 14 | 545291 | 646197 | 629162 | 584135 | 556420 | 540245 | 538140 | 542884 | 540142 | 545681 | 541909 | 545231 |
| 15 | 625972 | 728884 | 720269 | 669534 | 642796 | 626775 | 623981 | 618829 | 620242 | 625801 | 624444 | 624113 |
| 16 | 712217 | 816258 | 809769 | 772625 | 735809 | 712965 | 707334 | 705389 | 707144 | 711350 | 712750 | 710858 |
| 17 | 804026 | 908325 | 904022 | 869356 | 835333 | 805271 | 801771 | 800798 | 796318 | 802470 | 802048 | 799972 |
| 18 | 901400 | 1005092 | 1009714 | 983576 | 941205 | 912197 | 896359 | 899088 | 898826 | 899226 | 897221 | 901981 |
| 19 | 1004337 | 1106562 | 1113738 | 1089758 | 1053247 | 1017348 | 1008328 | 997109 | 999814 | 1001659 | 1001638 | 1002191 |
| 20 | 1112839 | 1212738 | 1222584 | 1212036 | 1171277 | 1128657 | 1114704 | 1105743 | 1110055 | 1109800 | 1111013 | 1110996 |

| | | | | | Number of Samples | | | | | | | |
|---|---|---|---|---|---|---|---|---|---|---|---|---|
| PartSize (μm) | 14 | 15 | 16 | 17 | 18 | 19 | 20 | 21 | 22 | 23 | 24 | 25 |
| 3 | 25052 | 24924 | 25385 | 25038 | 24972 | 25376 | 24924 | 25053 | 24967 | 24694 | 25002 | 25074 |
| 4 | 44375 | 43943 | 44544 | 44584 | 44424 | 44518 | 44374 | 45076 | 44529 | 44513 | 44532 | 44513 |
| 5 | 69769 | 69567 | 69687 | 69453 | 69324 | 68746 | 69403 | 69608 | 69748 | 70353 | 69403 | 69491 |
| 6 | 100095 | 100173 | 101196 | 100181 | 100152 | 100058 | 100333 | 101182 | 100178 | 99972 | 100312 | 101183 |
| 7 | 137583 | 136347 | 136360 | 135091 | 136649 | 136396 | 136572 | 136345 | 136401 | 136166 | 136086 | 136318 |
| 8 | 177618 | 179446 | 178296 | 177704 | 178496 | 178080 | 178506 | 179422 | 177870 | 178470 | 176663 | 178277 |
| 9 | 224409 | 225870 | 226913 | 225747 | 225688 | 225335 | 225475 | 225092 | 225353 | 224545 | 225100 | 225100 |
| 10 | 278026 | 277563 | 278141 | 279887 | 277559 | 277975 | 277771 | 279849 | 278147 | 278199 | 278050 | 278230 |
| 11 | 336508 | 334868 | 337048 | 336899 | 338457 | 336925 | 336537 | 336442 | 334821 | 336125 | 335998 | 334835 |
| 12 | 400732 | 400403 | 402547 | 401330 | 401889 | 402549 | 400939 | 402510 | 401875 | 401135 | 400279 | 400402 |
| 13 | 471435 | 469976 | 470120 | 469372 | 468991 | 470170 | 472232 | 470173 | 470428 | 470528 | 469915 | |
| 14 | 545684 | 545055 | 545968 | 544722 | 545643 | 543111 | 543758 | 547445 | 543793 | 543156 | 546110 | 544817 |
| 15 | 623156 | 627941 | 627956 | 623596 | 625699 | 625508 | 625921 | 625403 | 628246 | 625960 | 625281 | 626499 |
| 16 | 713247 | 712526 | 712140 | 711387 | 713858 | 712386 | 714032 | 714484 | 712116 | 714584 | 713964 | 712297 |
| 17 | 802794 | 802545 | 804929 | 804406 | 801803 | 803495 | 801598 | 803211 | 805840 | 803641 | 806506 | 804699 |
| 18 | 899873 | 897851 | 903332 | 903652 | 898573 | 901744 | 901317 | 903943 | 902120 | 901066 | 901991 | 903969 |
| 19 | 1000134 | 1003690 | 1003910 | 1005004 | 1005084 | 1004174 | 1002846 | 1003340 | 1004640 | 1004998 | 1002845 | 1004214 |
| 20 | 1113547 | 1111234 | 1113162 | 1112652 | 1111605 | 1112863 | 1113821 | 1115384 | 1112640 | 1112915 | 1113797 | 1112764 |

TABLE 11

Maximum Sampled Convolution Matrix: MaxSampledConvolutionMatrix
Maximum of the estimated convolution as a function of particle size (PartSize) and number of samples in the estimate. The UnSamp column is the maximum of the "original reference" convolution.

| | | | | | | Number of Samples | | | | | | |
|---|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 626 | 626 | 430 | 626 | 551 | 626 | 581 | 626 | 604 | 626 | 604 | 626 |
| 4 | 1023 | 1023 | 672 | 1023 | 896 | 1023 | 942 | 1023 | 979 | 1023 | 993 | 1023 |

TABLE 11-continued

Maximum Sampled Convolution Matrix: MaxSampledConvolutionMatrix
Maximum of the estimated convolution as a function of particle size (PartSize) and number of
samples in the estimate. The UnSamp column is the maximum of the "original reference" convolution.

| | | | | | | | | | | | | |
|---|---|---|---|---|---|---|---|---|---|---|---|---|
| 5 | 1451 | 1451 | 941 | 1451 | 1267 | 1451 | 1357 | 1451 | 1381 | 1451 | 1418 | 1451 |
| 6 | 1884 | 1884 | 1292 | 1884 | 1652 | 1884 | 1751 | 1884 | 1803 | 1884 | 1824 | 1884 |
| 7 | 2287 | 2287 | 1621 | 2287 | 2047 | 2287 | 2146 | 2287 | 2199 | 2287 | 2241 | 2287 |
| 8 | 2670 | 2670 | 1966 | 2670 | 2444 | 2670 | 2565 | 2670 | 2606 | 2670 | 2623 | 2670 |
| 9 | 3045 | 3045 | 2382 | 3045 | 2837 | 3045 | 2940 | 3045 | 2977 | 3045 | 3006 | 3045 |
| 10 | 3415 | 3415 | 2745 | 3415 | 3214 | 3415 | 3307 | 3415 | 3357 | 3415 | 3370 | 3415 |
| 11 | 3782 | 3782 | 3110 | 3782 | 3581 | 3782 | 3669 | 3782 | 3717 | 3782 | 3742 | 3782 |
| 12 | 4146 | 4146 | 3525 | 4146 | 3944 | 4146 | 4045 | 4146 | 4088 | 4146 | 4100 | 4146 |
| 13 | 4509 | 4509 | 3873 | 4509 | 4304 | 4509 | 4402 | 4509 | 4445 | 4509 | 4467 | 4509 |
| 14 | 4871 | 4871 | 4215 | 4871 | 4662 | 4871 | 4756 | 4871 | 4799 | 4871 | 4822 | 4871 |
| 15 | 5231 | 5231 | 4595 | 5231 | 5018 | 5231 | 5126 | 5231 | 5165 | 5231 | 5186 | 5231 |
| 16 | 5591 | 5591 | 4930 | 5591 | 5372 | 5591 | 5478 | 5591 | 5518 | 5591 | 5549 | 5591 |
| 17 | 5949 | 5949 | 5263 | 5949 | 5726 | 5949 | 5830 | 5949 | 5881 | 5949 | 5902 | 5949 |
| 18 | 6308 | 6308 | 5633 | 6308 | 6079 | 6308 | 6182 | 6308 | 6233 | 6308 | 6263 | 6308 |
| 19 | 6666 | 6666 | 5964 | 6666 | 6431 | 6666 | 6547 | 6666 | 6595 | 6666 | 6615 | 6666 |
| 20 | 7023 | 7023 | 6294 | 7023 | 6782 | 7023 | 6898 | 7023 | 6946 | 7023 | 6975 | 7023 |

| | Number of Samples | | | | | | | | | | | |
|---|---|---|---|---|---|---|---|---|---|---|---|---|
| PartSize (μm) | 14 | 15 | 16 | 17 | 18 | 19 | 20 | 21 | 22 | 23 | 24 | 25 |
| 3 | 613 | 626 | 619 | 626 | 619 | 626 | 619 | 626 | 619 | 626 | 624 | 626 |
| 4 | 1005 | 1023 | 1005 | 1023 | 1014 | 1023 | 1014 | 1023 | 1014 | 1023 | 1014 | 1023 |
| 5 | 1418 | 1451 | 1431 | 1451 | 1431 | 1451 | 1441 | 1451 | 1441 | 1451 | 1441 | 1451 |
| 6 | 1843 | 1884 | 1858 | 1884 | 1858 | 1884 | 1858 | 1884 | 1870 | 1884 | 1870 | 1884 |
| 7 | 2257 | 2287 | 2257 | 2287 | 2269 | 2287 | 2269 | 2287 | 2269 | 2287 | 2278 | 2287 |
| 8 | 2636 | 2670 | 2648 | 2670 | 2648 | 2670 | 2657 | 2670 | 2657 | 2670 | 2657 | 2670 |
| 9 | 3017 | 3045 | 3027 | 3045 | 3027 | 3045 | 3034 | 3045 | 3034 | 3045 | 3034 | 3045 |
| 10 | 3381 | 3415 | 3391 | 3415 | 3399 | 3415 | 3399 | 3415 | 3406 | 3415 | 3406 | 3415 |
| 11 | 3752 | 3782 | 3761 | 3782 | 3768 | 3782 | 3768 | 3782 | 3768 | 3782 | 3774 | 3782 |
| 12 | 4119 | 4146 | 4127 | 4146 | 4127 | 4146 | 4134 | 4146 | 4134 | 4146 | 4139 | 4146 |
| 13 | 4476 | 4509 | 4485 | 4509 | 4492 | 4509 | 4498 | 4509 | 4498 | 4509 | 4498 | 4509 |
| 14 | 4840 | 4871 | 4848 | 4871 | 4854 | 4871 | 4854 | 4871 | 4860 | 4871 | 4860 | 4871 |
| 15 | 5195 | 5231 | 5210 | 5231 | 5210 | 5231 | 5216 | 5231 | 5221 | 5231 | 5221 | 5231 |
| 16 | 5557 | 5591 | 5565 | 5591 | 5571 | 5591 | 5577 | 5591 | 5577 | 5591 | 5581 | 5591 |
| 17 | 5918 | 5949 | 5925 | 5949 | 5931 | 5949 | 5931 | 5949 | 5936 | 5949 | 5941 | 5949 |
| 18 | 6271 | 6308 | 6285 | 6308 | 6285 | 6308 | 6291 | 6308 | 6296 | 6308 | 6296 | 6308 |
| 19 | 6631 | 6666 | 6638 | 6666 | 6644 | 6666 | 6650 | 6666 | 6654 | 6666 | 6654 | 6666 |
| 20 | 6990 | 7023 | 6997 | 7023 | 7003 | 7023 | 7008 | 7023 | 7008 | 7023 | 7012 | 7023 |

TABLE 12

Average Sampled Convolution Matrix: AvgSampledConvolutionMatrix
Average of the estimated convolution as a function of particle size (PartSize) and number
of samples in the estimate. The UnSamp column is the average of the "original reference" convolution.

| | | Number of Samples | | | | | | | | | |
|---|---|---|---|---|---|---|---|---|---|---|---|
| PartSize (μm) | UnSamp | 3 | 4 | 5 | 6 | 7 | 8 | 9 | 10 | 11 | 12 |
| 3 | 278.21 | 208.81 | 215.31 | 221.65 | 236.95 | 243.99 | 243.68 | 246.47 | 256.68 | 258.98 | 254.06 |
| 4 | 445.14 | 341.20 | 336.23 | 360.87 | 380.11 | 384.64 | 387.66 | 399.26 | 404.28 | 413.67 | 411.98 |
| 5 | 632.30 | 483.93 | 470.86 | 504.96 | 537.74 | 540.35 | 560.88 | 566.88 | 567.34 | 586.15 | 591.74 |
| 6 | 834.63 | 628.31 | 646.24 | 679.11 | 707.19 | 728.22 | 735.44 | 755.33 | 755.83 | 772.63 | 767.42 |
| 7 | 1048.64 | 762.57 | 810.54 | 838.76 | 887.12 | 905.28 | 920.40 | 930.77 | 951.32 | 968.54 | 965.98 |
| 8 | 1271.82 | 890.43 | 983.46 | 1030.32 | 1075.37 | 1088.26 | 1130.20 | 1137.29 | 1148.64 | 1172.75 | 1177.14 |
| 9 | 1502.33 | 1015.48 | 1191.49 | 1203.36 | 1270.13 | 1302.51 | 1328.02 | 1344.02 | 1365.00 | 1384.17 | 1390.40 |
| 10 | 1738.81 | 1138.85 | 1373.02 | 1414.41 | 1466.83 | 1498.18 | 1524.93 | 1564.74 | 1571.97 | 1599.53 | 1598.63 |
| 11 | 1980.20 | 1261.13 | 1555.19 | 1600.15 | 1667.74 | 1697.91 | 1731.43 | 1761.30 | 1797.87 | 1819.25 | 1823.64 |
| 12 | 2225.68 | 1382.62 | 1762.62 | 1824.51 | 1873.67 | 1927.92 | 1962.62 | 1987.11 | 2024.39 | 2043.13 | 2057.05 |
| 13 | 2474.60 | 1503.54 | 1936.93 | 2018.18 | 2084.50 | 2132.46 | 2175.34 | 2211.11 | 2238.84 | 2270.60 | 2279.81 |
| 14 | 2726.46 | 1624.03 | 2108.05 | 2248.52 | 2299.75 | 2338.97 | 2389.33 | 2442.92 | 2455.45 | 2501.01 | 2500.91 |
| 15 | 2980.82 | 1744.17 | 2297.82 | 2445.47 | 2518.77 | 2574.78 | 2631.05 | 2651.18 | 2684.99 | 2732.24 | 2745.05 |
| 16 | 3237.35 | 1864.04 | 2465.37 | 2676.05 | 2740.80 | 2787.48 | 2845.43 | 2885.99 | 2925.47 | 2965.11 | 2991.26 |
| 17 | 3495.77 | 1983.69 | 2632.12 | 2873.01 | 2965.10 | 3002.86 | 3072.63 | 3125.08 | 3150.59 | 3199.83 | 3221.13 |
| 18 | 3755.83 | 2103.17 | 2816.83 | 3100.30 | 3190.95 | 3248.31 | 3289.42 | 3362.52 | 3401.03 | 3436.29 | 3450.32 |
| 19 | 4017.35 | 2222.48 | 2982.23 | 3292.79 | 3417.69 | 3468.78 | 3540.48 | 3576.57 | 3630.43 | 3674.33 | 3698.32 |
| 20 | 4280.15 | 2341.68 | 3147.28 | 3510.44 | 3644.76 | 3691.17 | 3760.11 | 3811.96 | 3876.95 | 3913.76 | 3944.58 |

TABLE 12-continued

Average Sampled Convolution Matrix: AvgSampledConvolutionMatrix
Average of the estimated convolution as a function of particle size (PartSize) and number
of samples in the estimate. The UnSamp column is the average of the "original reference" convolution.

| | Number of Samples | | | | | | | | | | |
|---|---|---|---|---|---|---|---|---|---|---|---|
| PartSize (μm) | 14 | 15 | 16 | 17 | 18 | 19 | 20 | 21 | 22 | 23 | 24 |
| 3 | 261.24 | 261.44 | 267.34 | 264.56 | 264.87 | 270.08 | 265.94 | 268.16 | 267.70 | 265.37 | 269.18 |
| 4 | 415.77 | 414.17 | 421.49 | 423.64 | 423.85 | 425.95 | 425.67 | 433.59 | 429.21 | 430.04 | 431.11 |
| 5 | 594.64 | 595.80 | 599.50 | 599.79 | 600.82 | 597.43 | 604.68 | 608.31 | 610.65 | 617.33 | 610.06 |
| 6 | 781.01 | 785.50 | 797.10 | 792.55 | 794.75 | 796.21 | 801.07 | 809.70 | 803.37 | 803.69 | 807.68 |
| 7 | 990.18 | 985.93 | 990.36 | 985.47 | 999.95 | 1001.51 | 1005.85 | 1006.78 | 1009.29 | 1009.53 | 1010.72 |
| 8 | 1185.85 | 1204.74 | 1202.79 | 1202.75 | 1212.36 | 1213.31 | 1220.11 | 1229.23 | 1221.11 | 1228.20 | 1217.92 |
| 9 | 1399.24 | 1414.14 | 1427.55 | 1426.17 | 1430.73 | 1432.90 | 1437.35 | 1440.34 | 1441.91 | 1446.78 | 1444.40 |
| 10 | 1623.00 | 1629.82 | 1639.10 | 1656.57 | 1648.89 | 1656.21 | 1659.78 | 1676.10 | 1669.33 | 1673.26 | 1675.76 |
| 11 | 1849.16 | 1849.34 | 1870.26 | 1875.33 | 1891.27 | 1889.09 | 1891.64 | 1896.28 | 1890.99 | 1902.06 | 1905.41 |
| 12 | 2080.21 | 2088.68 | 2108.28 | 2109.45 | 2119.57 | 2130.34 | 2128.28 | 2141.41 | 2142.43 | 2143.51 | 2143.16 |
| 13 | 2315.91 | 2321.24 | 2331.04 | 2337.96 | 2343.40 | 2356.56 | 2373.47 | 2367.73 | 2374.44 | 2381.06 | 2385.39 |
| 14 | 2549.01 | 2556.20 | 2573.33 | 2577.26 | 2588.81 | 2585.41 | 2596.34 | 2619.81 | 2608.80 | 2610.59 | 2629.46 |
| 15 | 2770.72 | 2805.42 | 2817.38 | 2808.39 | 2828.25 | 2834.41 | 2844.95 | 2850.38 | 2869.15 | 2864.62 | 2866.96 |
| 16 | 3027.22 | 3037.08 | 3048.23 | 3056.74 | 3078.75 | 3081.41 | 3096.47 | 3106.98 | 3104.37 | 3120.90 | 3123.52 |
| 17 | 3257.49 | 3274.67 | 3297.95 | 3307.86 | 3308.19 | 3323.31 | 3325.36 | 3341.13 | 3358.85 | 3357.26 | 3374.94 |
| 18 | 3503.01 | 3509.34 | 3545.38 | 3559.73 | 3551.41 | 3575.60 | 3581.76 | 3602.04 | 3603.65 | 3605.93 | 3617.25 |
| 19 | 3735.83 | 3767.31 | 3780.85 | 3798.98 | 3812.08 | 3821.42 | 3826.27 | 3838.53 | 3851.10 | 3861.11 | 3860.06 |
| 20 | 3999.97 | 4009.52 | 4034.23 | 4044.38 | 4053.81 | 4072.54 | 4084.93 | 4101.60 | 4101.36 | 4110.70 | 4121.68 |

TABLE 13

Sum Sampled Convolution Matrix: SumSampledConvolutionMatrix
Sum of the samples from the estimated convolution as a function of particle size (PartSize) and number of
samples in the estimate. The UnSamp column is the sum of the "original reference" convolution.

| | | Number of Samples | | | | | | | | | |
|---|---|---|---|---|---|---|---|---|---|---|---|
| PartSize (μm) | UnSamp | 3 | 4 | 5 | 6 | 7 | 8 | 9 | 10 | 11 | 12 | 13 |
| 3 | 25039 | 626 | 861 | 1108 | 1422 | 1708 | 1949 | 2218 | 2567 | 2849 | 3049 | 3376 |
| 4 | 44514 | 1024 | 1345 | 1804 | 2281 | 2693 | 3101 | 3593 | 4043 | 4550 | 4944 | 5394 |
| 5 | 69552 | 1452 | 1883 | 2525 | 3226 | 3782 | 4487 | 5102 | 5673 | 6448 | 7101 | 7566 |
| 6 | 100156 | 1885 | 2585 | 3396 | 4243 | 5098 | 5884 | 6798 | 7558 | 8499 | 9209 | 10200 |
| 7 | 136323 | 2288 | 3242 | 4194 | 5323 | 6337 | 7363 | 8377 | 9513 | 10654 | 11592 | 12671 |
| 8 | 178054 | 2671 | 3934 | 5152 | 6452 | 7618 | 9042 | 10236 | 11486 | 12900 | 14126 | 15369 |
| 9 | 225350 | 3046 | 4766 | 6017 | 7621 | 9118 | 10624 | 12096 | 13650 | 15226 | 16685 | 18144 |
| 10 | 278210 | 3417 | 5492 | 7072 | 8801 | 10487 | 12199 | 14083 | 15720 | 17595 | 19184 | 21005 |
| 11 | 336634 | 3783 | 6221 | 8001 | 10006 | 11885 | 13851 | 15852 | 17979 | 20012 | 21884 | 23770 |
| 12 | 400622 | 4148 | 7050 | 9123 | 11242 | 13495 | 15701 | 17884 | 20244 | 22474 | 24685 | 26985 |
| 13 | 470175 | 4511 | 7748 | 10091 | 12507 | 14927 | 17403 | 19900 | 22388 | 24977 | 27358 | 29836 |
| 14 | 545291 | 4872 | 8432 | 11243 | 13799 | 16373 | 19115 | 21986 | 24554 | 27511 | 30011 | 32894 |
| 15 | 625972 | 5233 | 9191 | 12227 | 15113 | 18023 | 21048 | 23861 | 26850 | 30055 | 32941 | 35904 |
| 16 | 712217 | 5592 | 9861 | 13380 | 16445 | 19512 | 22763 | 25974 | 29255 | 32616 | 35896 | 39020 |
| 17 | 804026 | 5951 | 10528 | 14365 | 17791 | 21020 | 24581 | 28126 | 31506 | 35198 | 38654 | 42000 |
| 18 | 901400 | 6310 | 11267 | 15502 | 19146 | 22738 | 26315 | 30263 | 34010 | 37799 | 41404 | 45390 |
| 19 | 1004337 | 6667 | 11929 | 16464 | 20506 | 24281 | 28324 | 32189 | 36304 | 40418 | 44380 | 48412 |
| 20 | 1112839 | 7025 | 12589 | 17552 | 21869 | 25838 | 30081 | 34308 | 38769 | 43051 | 47335 | 51588 |

| | Number of Samples | | | | | | | | | | | |
|---|---|---|---|---|---|---|---|---|---|---|---|---|
| PartSize (μm) | 14 | 15 | 16 | 17 | 18 | 19 | 20 | 21 | 22 | 23 | 24 | 25 |
| 3 | 3657 | 3922 | 4277 | 4498 | 4768 | 5131 | 5319 | 5631 | 5889 | 6103 | 6460 | 6760 |
| 4 | 5821 | 6213 | 6744 | 7202 | 7629 | 8093 | 8513 | 9105 | 9443 | 9891 | 10347 | 10791 |
| 5 | 8325 | 8937 | 9592 | 10196 | 10815 | 11351 | 12094 | 12775 | 13434 | 14199 | 14641 | 15297 |
| 6 | 10934 | 11783 | 12754 | 13473 | 14306 | 15128 | 16021 | 17004 | 17674 | 18485 | 19384 | 20405 |
| 7 | 13863 | 14789 | 15846 | 16753 | 17999 | 19029 | 20117 | 21142 | 22204 | 23219 | 24257 | 25364 |
| 8 | 16602 | 18071 | 19245 | 20447 | 21822 | 23053 | 24402 | 25814 | 26864 | 28249 | 29230 | 30783 |
| 9 | 19589 | 21212 | 22841 | 24245 | 25753 | 27225 | 28747 | 30247 | 31722 | 33276 | 34666 | 36252 |
| 10 | 22722 | 24447 | 26226 | 28162 | 29680 | 31468 | 33196 | 35198 | 36725 | 38485 | 40218 | 41989 |
| 11 | 25888 | 27740 | 29924 | 31881 | 34043 | 35893 | 37833 | 39822 | 41602 | 43747 | 45730 | 47548 |
| 12 | 29123 | 31330 | 33732 | 35861 | 38152 | 40476 | 42566 | 44970 | 47133 | 49301 | 51436 | 53691 |
| 13 | 32423 | 34819 | 37297 | 39745 | 42181 | 44775 | 47470 | 49722 | 52238 | 54764 | 57249 | 59667 |
| 14 | 35686 | 38343 | 41173 | 43813 | 46599 | 49123 | 51927 | 55016 | 57394 | 60044 | 63107 | 65711 |
| 15 | 38790 | 42081 | 45078 | 47743 | 50909 | 53854 | 56899 | 59858 | 63121 | 65886 | 68807 | 71930 |
| 16 | 42381 | 45556 | 48772 | 51965 | 55417 | 58547 | 61929 | 65247 | 68296 | 71781 | 74965 | 78057 |
| 17 | 45605 | 49120 | 52767 | 56234 | 59547 | 63143 | 66507 | 70164 | 73895 | 77217 | 80999 | 84317 |
| 18 | 49042 | 52640 | 56726 | 60515 | 63925 | 67936 | 71635 | 75643 | 79280 | 82936 | 86814 | 90771 |

TABLE 13-continued

Sum Sampled Convolution Matrix: SumSampledConvolutionMatrix
Sum of the samples from the estimated convolution as a function of particle size (PartSize) and number of
samples in the estimate. The UnSamp column is the sum of the "original reference" convolution.

| 19 | 52302 | 56510 | 60494 | 64583 | 68617 | 72607 | 76525 | 80609 | 84724 | 88806 | 92642 | 96801 |
| 20 | 56000 | 60143 | 64548 | 68755 | 72969 | 77378 | 81699 | 86134 | 90230 | 94546 | 98920 | 103123 |

TABLE 14

Distance matrix for 3 samples for particle sizes between 3 and 20 microns.
The values in this table were used to generate the heat map in FIG. 26.

| NSamples | PartSize (μm) | 3 | 4 | 5 | 6 | 7 | 8 | 9 | 10 | 11 |
|---|---|---|---|---|---|---|---|---|---|---|
| 3 | 3 | 0.00000 | 0.00043 | 0.00064 | 0.00077 | 0.00084 | 0.00090 | 0.00093 | 0.00097 | 0.00099 |
| 3 | 4 | 0.00043 | 0.00000 | 0.00022 | 0.00034 | 0.00042 | 0.00047 | 0.00051 | 0.00054 | 0.00057 |
| 3 | 5 | 0.00064 | 0.00022 | 0.00000 | 0.00013 | 0.00020 | 0.00025 | 0.00029 | 0.00032 | 0.00035 |
| 3 | 6 | 0.00077 | 0.00034 | 0.00013 | 0.00000 | 0.00008 | 0.00013 | 0.00017 | 0.00020 | 0.00022 |
| 3 | 7 | 0.00084 | 0.00042 | 0.00020 | 0.00008 | 0.00000 | 0.00005 | 0.00009 | 0.00012 | 0.00015 |
| 3 | 8 | 0.00090 | 0.00047 | 0.00025 | 0.00013 | 0.00005 | 0.00000 | 0.00004 | 0.00007 | 0.00010 |
| 3 | 9 | 0.00093 | 0.00051 | 0.00029 | 0.00017 | 0.00009 | 0.00004 | 0.00000 | 0.00003 | 0.00006 |
| 3 | 10 | 0.00097 | 0.00054 | 0.00032 | 0.00020 | 0.00012 | 0.00007 | 0.00003 | 0.00000 | 0.00003 |
| 3 | 11 | 0.00099 | 0.00057 | 0.00035 | 0.00022 | 0.00015 | 0.00010 | 0.00006 | 0.00003 | 0.00000 |
| 3 | 12 | 0.00101 | 0.00059 | 0.00037 | 0.00024 | 0.00017 | 0.00012 | 0.00008 | 0.00005 | 0.00002 |
| 3 | 13 | 0.00103 | 0.00061 | 0.00039 | 0.00026 | 0.00019 | 0.00014 | 0.00010 | 0.00007 | 0.00004 |
| 3 | 14 | 0.00105 | 0.00062 | 0.00041 | 0.00028 | 0.00020 | 0.00015 | 0.00011 | 0.00008 | 0.00006 |
| 3 | 15 | 0.00106 | 0.00064 | 0.00042 | 0.00029 | 0.00022 | 0.00017 | 0.00013 | 0.00010 | 0.00007 |
| 3 | 16 | 0.00108 | 0.00065 | 0.00043 | 0.00031 | 0.00023 | 0.00018 | 0.00014 | 0.00011 | 0.00008 |
| 3 | 17 | 0.00109 | 0.00066 | 0.00045 | 0.00032 | 0.00024 | 0.00019 | 0.00015 | 0.00012 | 0.00010 |
| 3 | 18 | 0.00110 | 0.00067 | 0.00046 | 0.00033 | 0.00025 | 0.00020 | 0.00016 | 0.00013 | 0.00011 |
| 3 | 19 | 0.00111 | 0.00068 | 0.00047 | 0.00034 | 0.00026 | 0.00021 | 0.00017 | 0.00014 | 0.00012 |
| 3 | 20 | 0.00112 | 0.00069 | 0.00048 | 0.00035 | 0.00027 | 0.00022 | 0.00018 | 0.00015 | 0.00013 |

| NSamples | PartSize (μm) | 12 | 13 | 14 | 15 | 16 | 17 | 18 | 19 | 20 |
|---|---|---|---|---|---|---|---|---|---|---|
| 3 | 3 | 0.00101 | 0.00103 | 0.00105 | 0.00106 | 0.00108 | 0.00109 | 0.00110 | 0.00111 | 0.00112 |
| 3 | 4 | 0.00059 | 0.00061 | 0.00062 | 0.00064 | 0.00065 | 0.00066 | 0.00067 | 0.00068 | 0.00069 |
| 3 | 5 | 0.00037 | 0.00039 | 0.00041 | 0.00042 | 0.00043 | 0.00045 | 0.00046 | 0.00047 | 0.00048 |
| 3 | 6 | 0.00024 | 0.00026 | 0.00028 | 0.00029 | 0.00031 | 0.00032 | 0.00033 | 0.00034 | 0.00035 |
| 3 | 7 | 0.00017 | 0.00019 | 0.00020 | 0.00022 | 0.00023 | 0.00024 | 0.00025 | 0.00026 | 0.00027 |
| 3 | 8 | 0.00012 | 0.00014 | 0.00015 | 0.00017 | 0.00018 | 0.00019 | 0.00020 | 0.00021 | 0.00022 |
| 3 | 9 | 0.00008 | 0.00010 | 0.00011 | 0.00013 | 0.00014 | 0.00015 | 0.00016 | 0.00017 | 0.00018 |
| 3 | 10 | 0.00005 | 0.00007 | 0.00008 | 0.00010 | 0.00011 | 0.00012 | 0.00013 | 0.00014 | 0.00015 |
| 3 | 11 | 0.00002 | 0.00004 | 0.00006 | 0.00007 | 0.00008 | 0.00010 | 0.00011 | 0.00012 | 0.00013 |
| 3 | 12 | 0.00000 | 0.00002 | 0.00004 | 0.00005 | 0.00006 | 0.00007 | 0.00009 | 0.00010 | 0.00010 |
| 3 | 13 | 0.00002 | 0.00000 | 0.00002 | 0.00003 | 0.00004 | 0.00006 | 0.00007 | 0.00008 | 0.00009 |
| 3 | 14 | 0.00004 | 0.00002 | 0.00000 | 0.00001 | 0.00003 | 0.00004 | 0.00005 | 0.00006 | 0.00007 |
| 3 | 15 | 0.00005 | 0.00003 | 0.00001 | 0.00000 | 0.00001 | 0.00002 | 0.00004 | 0.00005 | 0.00005 |
| 3 | 16 | 0.00006 | 0.00004 | 0.00003 | 0.00001 | 0.00000 | 0.00001 | 0.00002 | 0.00003 | 0.00004 |
| 3 | 17 | 0.00007 | 0.00006 | 0.00004 | 0.00002 | 0.00001 | 0.00000 | 0.00001 | 0.00002 | 0.00003 |
| 3 | 18 | 0.00009 | 0.00007 | 0.00005 | 0.00004 | 0.00002 | 0.00001 | 0.00000 | 0.00001 | 0.00002 |
| 3 | 19 | 0.00010 | 0.00008 | 0.00006 | 0.00005 | 0.00003 | 0.00002 | 0.00001 | 0.00000 | 0.00001 |
| 3 | 20 | 0.00010 | 0.00009 | 0.00007 | 0.00005 | 0.00004 | 0.00003 | 0.00002 | 0.00001 | 0.00000 |

TABLE 15

Distance matrix for 6 samples for particle sizes between 3 and 20 microns.
The values in this table were used to generate the heat map in FIG. 27.

| NSamples | PartSize (μm) | 3 | 4 | 5 | 6 | 7 | 8 | 9 | 10 | 11 |
|---|---|---|---|---|---|---|---|---|---|---|
| 6 | 3 | 0.00000 | 0.09038 | 0.08210 | 0.02740 | 0.05406 | 0.15464 | 0.27029 | 0.40327 | 0.54468 |
| 6 | 4 | 0.09038 | 0.00000 | 0.00834 | 0.06311 | 0.14437 | 0.24499 | 0.36065 | 0.49364 | 0.63505 |
| 6 | 5 | 0.08210 | 0.00834 | 0.00000 | 0.05480 | 0.13606 | 0.23668 | 0.35235 | 0.48534 | 0.62675 |
| 6 | 6 | 0.02740 | 0.06311 | 0.05480 | 0.00000 | 0.08127 | 0.18189 | 0.29755 | 0.43054 | 0.57195 |
| 6 | 7 | 0.05406 | 0.14437 | 0.13606 | 0.08127 | 0.00000 | 0.10062 | 0.21629 | 0.34928 | 0.49069 |
| 6 | 8 | 0.15464 | 0.24499 | 0.23668 | 0.18189 | 0.10062 | 0.00000 | 0.11567 | 0.24865 | 0.39007 |
| 6 | 9 | 0.27029 | 0.36065 | 0.35235 | 0.29755 | 0.21629 | 0.11567 | 0.00000 | 0.13299 | 0.27440 |
| 6 | 10 | 0.40327 | 0.49364 | 0.48534 | 0.43054 | 0.34928 | 0.24865 | 0.13299 | 0.00000 | 0.14141 |
| 6 | 11 | 0.54468 | 0.63505 | 0.62675 | 0.57195 | 0.49069 | 0.39007 | 0.27440 | 0.14141 | 0.00000 |
| 6 | 12 | 0.68930 | 0.77967 | 0.77137 | 0.71658 | 0.63531 | 0.53469 | 0.41903 | 0.28604 | 0.14462 |
| 6 | 13 | 0.83386 | 0.92423 | 0.91594 | 0.86114 | 0.77988 | 0.67926 | 0.56359 | 0.43060 | 0.28919 |

TABLE 15-continued

Distance matrix for 6 samples for particle sizes between 3 and 20 microns.
The values in this table were used to generate the heat map in FIG. 27.

| | | | | | | | | | |
|---|---|---|---|---|---|---|---|---|---|
| 6 | 14 | 0.97585 | 1.06622 | 1.05792 | 1.00313 | 0.92186 | 0.82124 | 0.70558 | 0.57259 | 0.43118 |
| 6 | 15 | 1.11323 | 1.20360 | 1.19530 | 1.14051 | 1.05925 | 0.95863 | 0.84296 | 0.70997 | 0.56856 |
| 6 | 16 | 1.24441 | 1.33478 | 1.32648 | 1.27169 | 1.19042 | 1.08980 | 0.97414 | 0.84115 | 0.69974 |
| 6 | 17 | 1.36817 | 1.45854 | 1.45024 | 1.39545 | 1.31418 | 1.21356 | 1.09790 | 0.96491 | 0.82350 |
| 6 | 18 | 1.48368 | 1.57405 | 1.56575 | 1.51096 | 1.42970 | 1.32908 | 1.21341 | 1.08042 | 0.93901 |
| 6 | 19 | 1.59046 | 1.68083 | 1.67253 | 1.61774 | 1.53647 | 1.43585 | 1.32019 | 1.18720 | 1.04579 |
| 6 | 20 | 1.68833 | 1.77870 | 1.77040 | 1.71561 | 1.63434 | 1.53372 | 1.41806 | 1.28507 | 1.14366 |

| NSamples | PartSize (μm) | 12 | 13 | 14 | 15 | 16 | 17 | 18 | 19 | 20 |
|---|---|---|---|---|---|---|---|---|---|---|
| 6 | 3 | 0.68930 | 0.83386 | 0.97585 | 1.11323 | 1.24441 | 1.36817 | 1.48368 | 1.59046 | 1.68833 |
| 6 | 4 | 0.77967 | 0.92423 | 1.06622 | 1.20360 | 1.33478 | 1.45854 | 1.57405 | 1.68083 | 1.77870 |
| 6 | 5 | 0.77137 | 0.91594 | 1.05792 | 1.19530 | 1.32648 | 1.45024 | 1.56575 | 1.67253 | 1.77040 |
| 6 | 6 | 0.71658 | 0.86114 | 1.00313 | 1.14051 | 1.27169 | 1.39545 | 1.51096 | 1.61774 | 1.71561 |
| 6 | 7 | 0.63531 | 0.77988 | 0.92186 | 1.05925 | 1.19042 | 1.31418 | 1.42970 | 1.53647 | 1.63434 |
| 6 | 8 | 0.53469 | 0.67926 | 0.82124 | 0.95863 | 1.08980 | 1.21356 | 1.32908 | 1.43585 | 1.53372 |
| 6 | 9 | 0.41903 | 0.56359 | 0.70558 | 0.84296 | 0.97414 | 1.09790 | 1.21341 | 1.32019 | 1.41806 |
| 6 | 10 | 0.28604 | 0.43060 | 0.57259 | 0.70997 | 0.84115 | 0.96491 | 1.08042 | 1.18720 | 1.28507 |
| 6 | 11 | 0.14462 | 0.28919 | 0.43118 | 0.56856 | 0.69974 | 0.82350 | 0.93901 | 1.04579 | 1.14366 |
| 6 | 12 | 0.00000 | 0.14457 | 0.28655 | 0.42394 | 0.55511 | 0.67887 | 0.79439 | 0.90116 | 0.99903 |
| 6 | 13 | 0.14457 | 0.00000 | 0.14199 | 0.27937 | 0.41055 | 0.53431 | 0.64982 | 0.75660 | 0.85447 |
| 6 | 14 | 0.28655 | 0.14199 | 0.00000 | 0.13738 | 0.26856 | 0.39232 | 0.50783 | 0.61461 | 0.71248 |
| 6 | 15 | 0.42394 | 0.27937 | 0.13738 | 0.00000 | 0.13118 | 0.25494 | 0.37045 | 0.47723 | 0.57510 |
| 6 | 16 | 0.55511 | 0.41055 | 0.26856 | 0.13118 | 0.00000 | 0.12376 | 0.23927 | 0.34605 | 0.44392 |
| 6 | 17 | 0.67887 | 0.53431 | 0.39232 | 0.25494 | 0.12376 | 0.00000 | 0.11551 | 0.22229 | 0.32016 |
| 6 | 18 | 0.79439 | 0.64982 | 0.50783 | 0.37045 | 0.23927 | 0.11551 | 0.00000 | 0.10678 | 0.20465 |
| 6 | 19 | 0.90116 | 0.75660 | 0.61461 | 0.47723 | 0.34605 | 0.22229 | 0.10678 | 0.00000 | 0.09787 |
| 6 | 20 | 0.99903 | 0.85447 | 0.71248 | 0.57510 | 0.44392 | 0.32016 | 0.20465 | 0.09787 | 0.00000 |

TABLE 16

Distance matrix for 12 samples for particle sizes between 3 and 20 microns.
The values in this table were used to generate the heat map in FIG. 28.

| NSamples | PartSize (μm) | 3 | 4 | 5 | 6 | 7 | 8 | 9 | 10 | 11 |
|---|---|---|---|---|---|---|---|---|---|---|
| 12 | 3 | 0.00000 | 0.13887 | 0.13834 | 0.05572 | 0.20785 | 0.43409 | 0.67332 | 0.89901 | 1.10362 |
| 12 | 4 | 0.13887 | 0.00000 | 0.01970 | 0.14103 | 0.33330 | 0.56401 | 0.80533 | 1.03268 | 1.23855 |
| 12 | 5 | 0.13834 | 0.01970 | 0.00000 | 0.13698 | 0.33013 | 0.56115 | 0.80251 | 1.02984 | 1.23558 |
| 12 | 6 | 0.05572 | 0.14103 | 0.13698 | 0.00000 | 0.19328 | 0.42447 | 0.66612 | 0.89397 | 1.10046 |
| 12 | 7 | 0.20785 | 0.33330 | 0.33013 | 0.19328 | 0.00000 | 0.23128 | 0.47318 | 0.70157 | 0.90897 |
| 12 | 8 | 0.43409 | 0.56401 | 0.56115 | 0.42447 | 0.23128 | 0.00000 | 0.24211 | 0.47112 | 0.67964 |
| 12 | 9 | 0.67332 | 0.80533 | 0.80251 | 0.66612 | 0.47318 | 0.24211 | 0.00000 | 0.22951 | 0.43910 |
| 12 | 10 | 0.89901 | 1.03268 | 1.02984 | 0.89397 | 0.70157 | 0.47112 | 0.22951 | 0.00000 | 0.21022 |
| 12 | 11 | 1.10362 | 1.23855 | 1.23558 | 1.10046 | 0.90897 | 0.67964 | 0.43910 | 0.21022 | 0.00000 |
| 12 | 12 | 1.28152 | 1.41752 | 1.41435 | 1.28035 | 1.09030 | 0.86285 | 0.62429 | 0.39704 | 0.18789 |
| 12 | 13 | 1.44165 | 1.57835 | 1.57505 | 1.44225 | 1.25380 | 1.02836 | 0.79192 | 0.56637 | 0.35832 |
| 12 | 14 | 1.59165 | 1.72880 | 1.72547 | 1.59399 | 1.40730 | 1.18408 | 0.94992 | 0.72625 | 0.51950 |
| 12 | 15 | 1.72866 | 1.86607 | 1.86276 | 1.73262 | 1.54773 | 1.32670 | 1.09481 | 0.87301 | 0.66761 |
| 12 | 16 | 1.85504 | 1.99255 | 1.98932 | 1.86050 | 1.67738 | 1.45849 | 1.22881 | 1.00884 | 0.80482 |
| 12 | 17 | 1.96871 | 2.10621 | 2.10312 | 1.97564 | 1.79433 | 1.57764 | 1.35025 | 1.13224 | 0.92978 |
| 12 | 18 | 2.06767 | 2.20509 | 2.20217 | 2.07593 | 1.89627 | 1.68157 | 1.45625 | 1.24003 | 1.03906 |
| 12 | 19 | 2.16164 | 2.29890 | 2.29618 | 2.17121 | 1.99326 | 1.78063 | 1.55747 | 1.34316 | 1.14383 |
| 12 | 20 | 2.24941 | 2.38646 | 2.38394 | 2.26019 | 2.08390 | 1.87327 | 1.65219 | 1.43973 | 1.24198 |

| NSamples | PartSize (μm) | 12 | 13 | 14 | 15 | 16 | 17 | 18 | 19 | 20 |
|---|---|---|---|---|---|---|---|---|---|---|
| 12 | 3 | 1.28152 | 1.44165 | 1.59165 | 1.72866 | 1.85504 | 1.96871 | 2.06767 | 2.16164 | 2.24941 |
| 12 | 4 | 1.41752 | 1.57835 | 1.72880 | 1.86607 | 1.99255 | 2.10621 | 2.20509 | 2.29890 | 2.38646 |
| 12 | 5 | 1.41435 | 1.57505 | 1.72547 | 1.86276 | 1.98932 | 2.10312 | 2.20217 | 2.29618 | 2.38394 |
| 12 | 6 | 1.28035 | 1.44225 | 1.59399 | 1.73262 | 1.86050 | 1.97564 | 2.07593 | 2.17121 | 2.26019 |
| 12 | 7 | 1.09030 | 1.25380 | 1.40730 | 1.54773 | 1.67738 | 1.79433 | 1.89627 | 1.99326 | 2.08390 |
| 12 | 8 | 0.86285 | 1.02836 | 1.18408 | 1.32670 | 1.45849 | 1.57764 | 1.68157 | 1.78063 | 1.87327 |
| 12 | 9 | 0.62429 | 0.79192 | 0.94992 | 1.09481 | 1.22881 | 1.35025 | 1.45625 | 1.55747 | 1.65219 |
| 12 | 10 | 0.39704 | 0.56637 | 0.72625 | 0.87301 | 1.00884 | 1.13224 | 1.24003 | 1.34316 | 1.43973 |
| 12 | 11 | 0.18789 | 0.35832 | 0.51950 | 0.66761 | 0.80482 | 0.92978 | 1.03906 | 1.14383 | 1.24198 |
| 12 | 12 | 0.00000 | 0.17067 | 0.33239 | 0.48121 | 0.61925 | 0.74527 | 0.85567 | 0.96169 | 1.06108 |
| 12 | 13 | 0.17067 | 0.00000 | 0.16205 | 0.31138 | 0.45006 | 0.57696 | 0.68832 | 0.79544 | 0.89590 |
| 12 | 14 | 0.33239 | 0.16205 | 0.00000 | 0.14954 | 0.28858 | 0.41606 | 0.52816 | 0.63615 | 0.73747 |
| 12 | 15 | 0.48121 | 0.31138 | 0.14954 | 0.00000 | 0.13920 | 0.26709 | 0.37974 | 0.48842 | 0.59042 |
| 12 | 16 | 0.61925 | 0.45006 | 0.28858 | 0.13920 | 0.00000 | 0.12816 | 0.24122 | 0.35044 | 0.45297 |

TABLE 16-continued

Distance matrix for 12 samples for particle sizes between 3 and 20 microns.
The values in this table were used to generate the heat map in FIG. 28.

| 12 | 17 | 0.74527 | 0.57696 | 0.41606 | 0.26709 | 0.12816 | 0.00000 | 0.11331 | 0.22283 | 0.32568 |
| 12 | 18 | 0.85567 | 0.68832 | 0.52816 | 0.37974 | 0.24122 | 0.11331 | 0.00000 | 0.10964 | 0.21263 |
| 12 | 19 | 0.96169 | 0.79544 | 0.63615 | 0.48842 | 0.35044 | 0.22283 | 0.10964 | 0.00000 | 0.10305 |
| 12 | 20 | 1.06108 | 0.89590 | 0.73747 | 0.59042 | 0.45297 | 0.32568 | 0.21263 | 0.10305 | 0.00000 |

TABLE 17

Distance matrix for 18 samples for particle sizes between 3 and 20 microns.
The values in this table were used to generate the heat map in FIG. 29.

| NSamples | PartSize (μm) | 3 | 4 | 5 | 6 | 7 | 8 | 9 | 10 | 11 |
|---|---|---|---|---|---|---|---|---|---|---|
| 18 | 3 | 0.00000 | 0.16694 | 0.16027 | 0.06575 | 0.25789 | 0.55058 | 0.84325 | 1.10875 | 1.35328 |
| 18 | 4 | 0.16694 | 0.00000 | 0.02488 | 0.16398 | 0.40749 | 0.70461 | 0.99988 | 1.26789 | 1.51427 |
| 18 | 5 | 0.16027 | 0.02488 | 0.00000 | 0.15154 | 0.39737 | 0.69535 | 0.99080 | 1.25864 | 1.50492 |
| 18 | 6 | 0.06575 | 0.16398 | 0.15154 | 0.00000 | 0.24650 | 0.54490 | 0.84043 | 1.10837 | 1.35510 |
| 18 | 7 | 0.25789 | 0.40749 | 0.39737 | 0.24650 | 0.00000 | 0.29852 | 0.59438 | 0.86327 | 1.11147 |
| 18 | 8 | 0.55058 | 0.70461 | 0.69535 | 0.54490 | 0.29852 | 0.00000 | 0.29642 | 0.56702 | 0.81739 |
| 18 | 9 | 0.84325 | 0.99988 | 0.99080 | 0.84043 | 0.59438 | 0.29642 | 0.00000 | 0.27195 | 0.52403 |
| 18 | 10 | 1.10875 | 1.26789 | 1.25864 | 1.10837 | 0.86327 | 0.56702 | 0.27195 | 0.00000 | 0.25267 |
| 18 | 11 | 1.35328 | 1.51427 | 1.50492 | 1.35510 | 1.11147 | 0.81739 | 0.52403 | 0.25267 | 0.00000 |
| 18 | 12 | 1.57412 | 1.73651 | 1.72712 | 1.57813 | 1.33644 | 1.04502 | 0.75393 | 0.48388 | 0.23203 |
| 18 | 13 | 1.77586 | 1.93923 | 1.92988 | 1.78197 | 1.54247 | 1.25394 | 0.96539 | 0.69707 | 0.44642 |
| 18 | 14 | 1.96118 | 2.12519 | 2.11597 | 1.96926 | 1.73204 | 1.44641 | 1.16046 | 0.89401 | 0.64471 |
| 18 | 15 | 2.12866 | 2.29305 | 2.28404 | 2.13866 | 1.90379 | 1.62110 | 1.33785 | 1.07349 | 0.82580 |
| 18 | 16 | 2.27896 | 2.44353 | 2.43480 | 2.29082 | 2.05834 | 1.77863 | 1.49819 | 1.23610 | 0.99026 |
| 18 | 17 | 2.41700 | 2.58160 | 2.57319 | 2.43061 | 2.20049 | 1.92370 | 1.64603 | 1.38624 | 1.14232 |
| 18 | 18 | 2.54435 | 2.70886 | 2.70077 | 2.55959 | 2.33176 | 2.05779 | 1.78284 | 1.52533 | 1.28336 |
| 18 | 19 | 2.66278 | 2.82713 | 2.81936 | 2.67953 | 2.45390 | 2.18263 | 1.91027 | 1.65498 | 1.41490 |
| 18 | 20 | 2.77070 | 2.93486 | 2.92742 | 2.78890 | 2.56535 | 2.29663 | 2.02675 | 1.77360 | 1.53540 |

| NSamples | PartSize (μm) | 12 | 13 | 14 | 15 | 16 | 17 | 18 | 19 | 20 |
|---|---|---|---|---|---|---|---|---|---|---|
| 18 | 3 | 1.57412 | 1.77586 | 1.96118 | 2.12866 | 2.27896 | 2.41700 | 2.54435 | 2.66278 | 2.77070 |
| 18 | 4 | 1.73651 | 1.93923 | 2.12519 | 2.29305 | 2.44353 | 2.58160 | 2.70886 | 2.82713 | 2.93486 |
| 18 | 5 | 1.72712 | 1.92988 | 2.11597 | 2.28404 | 2.43480 | 2.57319 | 2.70077 | 2.81936 | 2.92742 |
| 18 | 6 | 1.57813 | 1.78197 | 1.96926 | 2.13866 | 2.29082 | 2.43061 | 2.55959 | 2.67953 | 2.78890 |
| 18 | 7 | 1.33644 | 1.54247 | 1.73204 | 1.90379 | 2.05834 | 2.20049 | 2.33176 | 2.45390 | 2.56535 |
| 18 | 8 | 1.04502 | 1.25394 | 1.44641 | 1.62110 | 1.77863 | 1.92370 | 2.05779 | 2.18263 | 2.29663 |
| 18 | 9 | 0.75393 | 0.96539 | 1.16046 | 1.33785 | 1.49819 | 1.64603 | 1.78284 | 1.91027 | 2.02675 |
| 18 | 10 | 0.48388 | 0.69707 | 0.89401 | 1.07349 | 1.23610 | 1.38624 | 1.52533 | 1.65498 | 1.77360 |
| 18 | 11 | 0.23203 | 0.44642 | 0.64471 | 0.82580 | 0.99026 | 1.14232 | 1.28336 | 1.41490 | 1.53540 |
| 18 | 12 | 0.00000 | 0.21484 | 0.41383 | 0.59595 | 0.76177 | 0.91531 | 1.05790 | 1.19098 | 1.31304 |
| 18 | 13 | 0.21484 | 0.00000 | 0.19928 | 0.38206 | 0.54890 | 0.70361 | 0.84745 | 0.98179 | 1.10517 |
| 18 | 14 | 0.41383 | 0.19928 | 0.00000 | 0.18318 | 0.35077 | 0.50639 | 0.65122 | 0.78655 | 0.91102 |
| 18 | 15 | 0.59595 | 0.38206 | 0.18318 | 0.00000 | 0.16797 | 0.32412 | 0.46960 | 0.60562 | 0.73090 |
| 18 | 16 | 0.76177 | 0.54890 | 0.35077 | 0.16797 | 0.00000 | 0.15636 | 0.30216 | 0.43859 | 0.56443 |
| 18 | 17 | 0.91531 | 0.70361 | 0.50639 | 0.32412 | 0.15636 | 0.00000 | 0.14594 | 0.28261 | 0.40883 |
| 18 | 18 | 1.05790 | 0.84745 | 0.65122 | 0.46960 | 0.30216 | 0.14594 | 0.00000 | 0.13676 | 0.26325 |
| 18 | 19 | 1.19098 | 0.98179 | 0.78655 | 0.60562 | 0.43859 | 0.28261 | 0.13676 | 0.00000 | 0.12669 |
| 18 | 20 | 1.31304 | 1.10517 | 0.91102 | 0.73090 | 0.56443 | 0.40883 | 0.26325 | 0.12669 | 0.00000 |

TABLE 18

Distance matrix for 24 samples for particle sizes between 3 and 20 microns.
The values in this table were used to generate the heat map in FIG. 30.

| NSamples | PartSize (μm) | 3 | 4 | 5 | 6 | 7 | 8 | 9 | 10 | 11 |
|---|---|---|---|---|---|---|---|---|---|---|
| 24 | 3 | 0.00000 | 0.19419 | 0.18222 | 0.07542 | 0.30007 | 0.64220 | 0.97240 | 1.28012 | 1.56344 |
| 24 | 4 | 0.19419 | 0.00000 | 0.03141 | 0.18554 | 0.47353 | 0.82049 | 1.15414 | 1.46466 | 1.75023 |
| 24 | 5 | 0.18222 | 0.03141 | 0.00000 | 0.16650 | 0.45733 | 0.80523 | 1.13905 | 1.44953 | 1.73500 |
| 24 | 6 | 0.07542 | 0.18554 | 0.16650 | 0.00000 | 0.29293 | 0.64165 | 0.97505 | 1.28538 | 1.57113 |
| 24 | 7 | 0.30007 | 0.47353 | 0.45733 | 0.29293 | 0.00000 | 0.34888 | 0.68286 | 0.99454 | 1.28223 |
| 24 | 8 | 0.64220 | 0.82049 | 0.80523 | 0.64165 | 0.34888 | 0.00000 | 0.33535 | 0.64911 | 0.93949 |
| 24 | 9 | 0.97240 | 1.15414 | 1.13905 | 0.97505 | 0.68286 | 0.33535 | 0.00000 | 0.31470 | 0.60683 |
| 24 | 10 | 1.28012 | 1.46466 | 1.44953 | 1.28538 | 0.99454 | 0.64911 | 0.31470 | 0.00000 | 0.29296 |
| 24 | 11 | 1.56344 | 1.75023 | 1.73500 | 1.57113 | 1.28223 | 0.93949 | 0.60683 | 0.29296 | 0.00000 |
| 24 | 12 | 1.82019 | 2.00863 | 1.99342 | 1.83025 | 1.54376 | 1.20413 | 0.87379 | 0.56142 | 0.26923 |
| 24 | 13 | 2.05347 | 2.24307 | 2.22797 | 2.06582 | 1.78203 | 1.44581 | 1.11820 | 0.80781 | 0.51697 |

TABLE 18-continued

Distance matrix for 24 samples for particle sizes between 3 and 20 microns.
The values in this table were used to generate the heat map in FIG. 30.

| 24 | 14 | 2.26581 | 2.45615 | 2.44128 | 2.28034 | 1.99938 | 1.66664 | 1.34192 | 1.03378 | 0.74457 |
|----|----|---------|---------|---------|---------|---------|---------|---------|---------|---------|
| 24 | 15 | 2.45763 | 2.64839 | 2.63385 | 2.47429 | 2.19624 | 1.86705 | 1.54539 | 1.23976 | 0.95252 |
| 24 | 16 | 2.63318 | 2.82413 | 2.80996 | 2.65186 | 2.37670 | 2.05101 | 1.73244 | 1.42941 | 1.14428 |
| 24 | 17 | 2.79519 | 2.98617 | 2.97239 | 2.81576 | 2.54342 | 2.22112 | 1.90560 | 1.60516 | 1.32219 |
| 24 | 18 | 2.94164 | 3.13254 | 3.11920 | 2.96404 | 2.69443 | 2.37541 | 2.06288 | 1.76506 | 1.48432 |
| 24 | 19 | 3.07550 | 3.26623 | 3.25332 | 3.09962 | 2.83264 | 2.51678 | 2.20717 | 1.91195 | 1.63349 |
| 24 | 20 | 3.19964 | 3.39013 | 3.37766 | 3.22537 | 2.96092 | 2.64808 | 2.34129 | 2.04862 | 1.77240 |

| NSamples | PartSize (µm) | 12 | 13 | 14 | 15 | 16 | 17 | 18 | 19 | 20 |
|----------|---------------|---------|---------|---------|---------|---------|---------|---------|---------|---------|
| 24 | 3  | 1.82019 | 2.05347 | 2.26581 | 2.45763 | 2.63318 | 2.79519 | 2.94164 | 3.07550 | 3.19964 |
| 24 | 4  | 2.00863 | 2.24307 | 2.45615 | 2.64839 | 2.82413 | 2.98617 | 3.13254 | 3.26623 | 3.39013 |
| 24 | 5  | 1.99342 | 2.22797 | 2.44128 | 2.63385 | 2.80996 | 2.97239 | 3.11920 | 3.25332 | 3.37766 |
| 24 | 6  | 1.83025 | 2.06582 | 2.28034 | 2.47429 | 2.65186 | 2.81576 | 2.96404 | 3.09962 | 3.22537 |
| 24 | 7  | 1.54376 | 1.78203 | 1.99938 | 2.19624 | 2.37670 | 2.54342 | 2.69443 | 2.83264 | 2.96092 |
| 24 | 8  | 1.20413 | 1.44581 | 1.66664 | 1.86705 | 2.05101 | 2.22112 | 2.37541 | 2.51678 | 2.64808 |
| 24 | 9  | 0.87379 | 1.11820 | 1.34192 | 1.54539 | 1.73244 | 1.90560 | 2.06288 | 2.20717 | 2.34129 |
| 24 | 10 | 0.56142 | 0.80781 | 1.03378 | 1.23976 | 1.42941 | 1.60516 | 1.76506 | 1.91195 | 2.04862 |
| 24 | 11 | 0.26923 | 0.51697 | 0.74457 | 0.95252 | 1.14428 | 1.32219 | 1.48432 | 1.63349 | 1.77240 |
| 24 | 12 | 0.00000 | 0.24833 | 0.47688 | 0.68618 | 0.87951 | 1.05907 | 1.22301 | 1.37406 | 1.51487 |
| 24 | 13 | 0.24833 | 0.00000 | 0.22898 | 0.43917 | 0.63363 | 0.81442 | 0.97980 | 1.13241 | 1.27481 |
| 24 | 14 | 0.47688 | 0.22898 | 0.00000 | 0.21067 | 0.40583 | 0.58748 | 0.75394 | 0.90778 | 1.05147 |
| 24 | 15 | 0.68618 | 0.43917 | 0.21067 | 0.00000 | 0.19544 | 0.37754 | 0.54473 | 0.69948 | 0.84417 |
| 24 | 16 | 0.87951 | 0.63363 | 0.40583 | 0.19544 | 0.00000 | 0.18229 | 0.34996 | 0.50539 | 0.65085 |
| 24 | 17 | 1.05907 | 0.81442 | 0.58748 | 0.37754 | 0.18229 | 0.00000 | 0.16798 | 0.32392 | 0.46997 |
| 24 | 18 | 1.22301 | 0.97980 | 0.75394 | 0.54473 | 0.34996 | 0.16798 | 0.00000 | 0.15614 | 0.30251 |
| 24 | 19 | 1.37406 | 1.13241 | 0.90778 | 0.69948 | 0.50539 | 0.32392 | 0.15614 | 0.00000 | 0.14650 |
| 24 | 20 | 1.51487 | 1.27481 | 1.05147 | 0.84417 | 0.65085 | 0.46997 | 0.30251 | 0.14650 | 0.00000 |

The invention claimed is:

1. A system for measuring a total particle emission of a flow cytometer particle according to a plurality of digital samples, wherein the measurement is independent of how many are in the plurality of digital samples, the system comprising:
   a. an apparatus including a laser for providing a laser excitation energy, wherein said apparatus is adapted to pass said laser excitation energy from said laser into a generally perpendicular flow cytometer channel element through which a particle passes, said particle being adapted to be irradiated by said apparatus and to emit at least one fluorescent emission responsive to said laser excitation energy, wherein said at least one fluorescent emission results from a geometrical convolution of a geometrical form of both:
      i. said laser excitation energy; and
      ii. a geometric characteristic of at least one fluorescent emission of said particle;
   b. an analog emission detector adapted to detect at least some of said at least one fluorescent emission and to output an analog electrical emission;
   c. a digital sampler adapted to provide a plurality of digital time samples of said analog electrical emission;
   d. a processor, adapted to:
      i. process said plurality of digital time samples;
      ii. calculate a total fluorescent emission of said particle, by determining the extent of said geometric convolution and fitting said plurality of digital time samples to a function of a same extent, wherein said fitting comprises fitting a spline;
      iii. perform a sum of the fitted function, to determine said total fluorescent emission; and
      iv. output the sum of the fitting as the measurement of the total particle emission;
   wherein said flow cytometer channel element is adapted to pass a plurality of particles through said channel element in single file; and
   wherein said plurality of digital time samples is a function of a velocity of said particle, and the measurement of the total particle emission is independent of the velocity.

2. A system according to claim 1, wherein said digital sampler is adapted to sample said analog electrical emission from said plurality of said particles.

3. A system according to claim 2, wherein said flow cytometer channel element is adapted to pass said plurality of particles without a sheath fluid.

4. A system according to claim 3, wherein said deconvolution is a ratio of an integral of said geometric convolution with respect to an integral of said laser excitation energy.

5. A system according to claim 1, wherein said spline is a normalized spline.

6. A system according to claim 1, wherein said spline has a length determined according to at least one of a group consisting of:
   a length of a particle; and
   a length of an excitation in a convolution signal model.

7. A system according to claim 1, wherein said plurality of digital time samples is a function of a size of said particle, and the measurement of the total particle emission is independent of the size.

8. A system according to claim 1, wherein said apparatus is adapted to pass said laser excitation energy through an excitation window that is smaller than said particle.

9. A method for measuring a total particle emission of a flow cytometer particle according to a plurality of digital samples, wherein the measurement is independent of how many are in the plurality of digital samples, the method comprising:
   a. impinging a laser excitation energy onto a particle moving generally perpendicularly thereto, to induce said particle to emit at least one fluorescent emission responsive to said laser excitation energy, wherein said at least one fluorescent emission results from a geometrical convolution of a geometrical form of both:
   i. said laser excitation energy; and
   ii. a geometric characteristic of at least one fluorescent emission of said particle;
b. detecting at least some of said at least one fluorescent emission thereby outputting an analog electrical emission;
c. providing a plurality of digital time samples of said analog electrical emission;
d. processing said plurality of digital time samples to calculate a total fluorescent emission of said particle, by determining the extent of said geometric convolution and fitting said time samples to a function of a same extent, wherein said fitting comprises fitting a spline;
e. performing a sum of the fitted function, to determine total fluorescent emission; and
f. outputting the sum of the fitting as the measurement of the total particle emission;
wherein said impinging step further comprises passing a plurality of particles moving generally perpendicularly thereto in a single file; and
wherein a location of said plurality of digital time samples of said analog electrical emission is a function of a velocity of said particle, and the measurement of the total particle emission is independent of the velocity.

10. A method according to claim 9, wherein said provision step comprises sampling said analog electrical emission at fixed time intervals.

11. A method according to claim 10, wherein said plurality of particles comprise particles of different sizes and shapes.

12. A method according to claim 11, wherein said provision step further comprises providing a plurality of digital time samples of said analog electrical emission from said plurality of said particles.

13. A method according to claim 12, wherein said passing said plurality of said particles comprises passing said plurality of said particles without a sheath fluid.

14. A method according to claim 13, wherein a result of said convolution associated with each individual particle of said plurality of said particles is a function of a size of each said particle, and the measurement of the total particle emission is independent of the size.

15. A method according to claim 13, wherein a result of said convolution associated with each individual particle of said plurality of said particles is a function of a velocity of each said particle, and the measurement of the total particle emission is independent of the velocity.

16. A method according to claim 15, wherein said total fluorescent emission of said particle is obtained from a deconvolution.

17. A method according to claim 16, said deconvolution is a ratio of an integral of said geometric convolution with respect to an integral of said laser excitation energy.

18. A method according to claim 17, wherein said total fluorescent emission of said particle is determined at least in part according to at least one of the group consisting of a ratio of an average of convolution to an integral of convolution for a known particle size, a maximum of samples to an integral of convolution for a known particle size and a sample sum to an integral of convolution of a known particle size.

19. A method according to claim 18, wherein said processing step further comprises generating models of said geometric convolution as a function of how many are in said plurality of digital time samples.

20. A method according to claim 19, wherein said processing step further comprises comparing said geometric convolution to a normalized model.

21. A method according to claim 19, wherein said processing step further comprises determining the extent of said geometric convolution from a measurement of at least one of a size of said particle and a velocity of said particle.

22. A method according to claim 9, wherein said spline is a normalized spline.

23. A method according to claim 9, wherein said spline has a length determined according to at least one of a group consisting of:
   a length of a particle; and
   a length of an excitation in a convolution signal model.

24. A method according to claim 9, wherein said impinging said laser excitation energy onto said particle comprises passing said laser excitation energy through an excitation window that is smaller than said particle.

* * * * *